(12) United States Patent
Torii et al.

(10) Patent No.: US 10,406,256 B2
(45) Date of Patent: *Sep. 10, 2019

(54) GEL PULVERIZATION DEVICE, METHOD FOR MANUFACTURING POLYACRYLIC ACID (POLYACRYLATE) SUPERABSORBENT POLYMER POWDER, AND SUPERABSORBENT POLYMER POWDER

(71) Applicant: Nippon Shokubai Co., Ltd., Osaka (JP)

(72) Inventors: Kazushi Torii, Hyogo (JP); Kohei Omori, Hyogo (JP); Nobuya Tanaka, Hyogo (JP); Shigeru Sakamoto, Hyogo (JP); Kenji Tada, Hyogo (JP); Hironori Sato, Hyogo (JP)

(73) Assignee: NIPPON SHOKUBAI CO., LTD., Osaka-Shi, Osaka (JP)

( * ) Notice: Subject to any disclaimer, the term of this patent is extended or adjusted under 35 U.S.C. 154(b) by 259 days.

This patent is subject to a terminal disclaimer.

(21) Appl. No.: 14/914,150

(22) PCT Filed: Aug. 28, 2014

(86) PCT No.: PCT/JP2014/072621
§ 371 (c)(1),
(2) Date: Feb. 24, 2016

(87) PCT Pub. No.: WO2015/030130
PCT Pub. Date: Mar. 5, 2015

(65) Prior Publication Data
US 2016/0199529 A1    Jul. 14, 2016

(30) Foreign Application Priority Data

Aug. 28, 2013 (JP) .................................. 2013-177301
Mar. 27, 2014 (JP) .................................. 2014-067062

(51) Int. Cl.
*C08J 3/12* (2006.01)
*A61L 15/24* (2006.01)
(Continued)

(52) U.S. Cl.
CPC .............. *A61L 15/24* (2013.01); *B01J 20/261* (2013.01); *B02C 19/0056* (2013.01);
(Continued)

(58) Field of Classification Search
CPC . B01J 20/3021; C08J 3/075; C08J 3/12; C08J 2333/02; B29C 48/681; B29C 48/687
See application file for complete search history.

(56) References Cited

U.S. PATENT DOCUMENTS

| 4,538,917 A | 9/1985 | Harms |
| 4,640,672 A | 2/1987 | Ellwood |

(Continued)

FOREIGN PATENT DOCUMENTS

| EP | 2565219 A1 | 3/2013 |
| EP | 3040362 A1 | 7/2016 |

(Continued)

OTHER PUBLICATIONS

European Search Report dated Jun. 14, 2017 issued in 14839332.5.
(Continued)

*Primary Examiner* — Hoa (Holly) Le
(74) *Attorney, Agent, or Firm* — Harness, Dickey & Pierce, P.L.C.

(57) ABSTRACT

Provided is a water absorbent resin that is useful to sanitary materials such as a disposable diaper, a sanitary napkin, and a blood absorbent for medical use each having a higher liquid permeability and a higher water absorbing speed. Further provided is a water absorbent resin powder that is useful to sanitary materials such as a disposable diaper, a sanitary napkin, and a blood absorbent for medical use each (Continued)

having increased in absorbency of a liquid and in heat retaining property. A gel grinding device to be used to produce a water absorbent resin, includes: a screw; a feed opening; an extrusion opening; a porous plate; and a barrel, the barrel including a return preventing member provided on an inner surface thereof, and the return preventing member satisfying at least one of specific parameters.

4 Claims, 5 Drawing Sheets

(51) Int. Cl.
```
B02C 19/00      (2006.01)
B02C 19/22      (2006.01)
B29B 15/00      (2006.01)
B29B 9/06       (2006.01)
B29B 9/12       (2006.01)
C08J 3/075      (2006.01)
B01J 20/26      (2006.01)
C08F 2/10       (2006.01)
C08F 220/06     (2006.01)
C08F 6/00       (2006.01)
B29K 33/00      (2006.01)
B29K 105/00     (2006.01)
B29B 9/16       (2006.01)
B29C 48/68      (2019.01)
B29C 48/685     (2019.01)
```
(52) U.S. Cl.
CPC ............... *B02C 19/22* (2013.01); *B29B 9/06* (2013.01); *B29B 9/12* (2013.01); *B29B 15/00* (2013.01); *C08F 2/10* (2013.01); *C08F 6/008* (2013.01); *C08F 220/06* (2013.01); *C08J 3/075* (2013.01); *C08J 3/12* (2013.01); *B01J 2220/68* (2013.01); *B29B 9/16* (2013.01); *B29B 2009/125* (2013.01); *B29C 48/681* (2019.02); *B29C 48/687* (2019.02); *B29K 2033/00* (2013.01); *B29K 2105/251* (2013.01); *B29K 2995/0092* (2013.01); *C08J 2333/02* (2013.01)

(56) References Cited

U.S. PATENT DOCUMENTS

| | | | |
|---|---|---|---|
| 9,533,433 B2* | 1/2017 | Torii | B29B 9/06 |
| 2009/0305884 A1 | 12/2009 | Sakamoto et al. | |
| 2011/0313113 A1 | 12/2011 | Sakamoto et al. | |
| 2012/0184670 A1 | 7/2012 | Kobayashi et al. | |
| 2012/0258851 A1 | 10/2012 | Nakatsuru et al. | |
| 2013/0026412 A1 | 1/2013 | Machida et al. | |
| 2013/0101851 A1 | 4/2013 | Takaai et al. | |
| 2014/0296465 A1 | 10/2014 | Sakamoto et al. | |
| 2015/0129799 A1 | 5/2015 | Kobayashi et al. | |
| 2015/0259494 A1 | 9/2015 | Takaai et al. | |
| 2016/0207226 A1 | 7/2016 | Torii et al. | |

FOREIGN PATENT DOCUMENTS

| | | |
|---|---|---|
| JP | 11-209652 | 8/1999 |
| JP | 2000/63527 | 2/2000 |
| JP | 2012/12482 | 1/2012 |
| JP | 5989913 B2 | 8/2016 |
| WO | WO2011/040472 A1 | 4/2011 |
| WO | WO-2011126079 A1 | 10/2011 |
| WO | WO-2012/128056 A1 | 9/2012 |

OTHER PUBLICATIONS

International Preliminary Report on Patentability for PCT/JP2014/072621, dated Mar. 10, 2016.
Office Action dated Sep. 6, 2016 Issued in Japanese Patent Application No. JP 2015-534292.
International Search Report for International Application No. PCT/JP2014/072621 dated Nov. 25, 2014.
Partial Supplementary European Search Report dated Mar. 17, 2017 issued in EP 14839332.5.

* cited by examiner

US 10,406,256 B2

GEL PULVERIZATION DEVICE, METHOD FOR MANUFACTURING POLYACRYLIC ACID (POLYACRYLATE) SUPERABSORBENT POLYMER POWDER, AND SUPERABSORBENT POLYMER POWDER

TECHNICAL FIELD

The present invention relates to a gel grinding device, a method for producing a polyacrylic acid (salt)-based water absorbent resin powder, and a water absorbent resin powder.

BACKGROUND ART

A water absorbent resin (SAP/Super Absorbent Polymer) is a water-swelling and water-insoluble gelatinized polymer and is heavily used mainly for disposable purposes, i.e., for absorbent articles such as a disposable diaper and a sanitary napkin and for an agriculture/horticulture water retention agent, an industrial waterproofing material, and the like. As a raw material for such a hydrophilic polymer or water absorbent resin, there have been proposed many kinds of monomers. Of these raw materials, a polyacrylic acid (salt)-based water absorbent resin in which acrylic acid and a salt thereof are used as monomers or a combination of a polyacrylic acid-based water absorbent resin and a polyacrylic acid salt-based water absorbent resin is particularly industrially most widely used from the viewpoint of its high water absorption performance.

According to advancement of a disposable diaper which is the main purpose of use of the water absorbent resin, the water absorbent resin is required to have various functions (physical properties). Specific examples of the physical properties of the water absorbent resin include not only merely a high water absorption capacity but also a gel strength, a water soluble component, a water absorbing speed, a water absorption capacity under load, a liquid permeability, a particle size distribution, a urine resistance, an antibacterial property, an impact resistance (damage resistance), a powder fluidity, a deodorizing property, a coloration resistance (whiteness), a dust suppression property, and the like.

Of the physical properties described above, the liquid permeability is considered to be a more important physical property according to an increase in used amount (e.g., 50 wt % or more) of a water absorbent resin in a disposable diaper. Further, in addition to the liquid permeability, the water absorbing speed is considered to be fundamental physical properties of a water absorbent resin. Under the circumstances, there have been studied techniques for improving the liquid permeability of, preferably both the liquid permeability and the water absorbing speed of a water absorbent resin.

In addition, other than the physical properties described above, a heat retaining property of a water absorbent resin has gained attention according to an increase in used amount of a water absorbent resin in a disposable diaper (e.g., 40 mass % or more in which a water absorbent resin powder is contained based on a total mass of the water absorbent resin powder and a fibrous material), or according to use of disposable diapers in regions in various climates.

Patent Literature 1 studies a method for producing a polyacrylic acid (salt)-based water absorbent resin powder having both a higher liquid permeability and a higher water absorbing speed. Specifically, Patent Literature 1 studies control of a gel grinding step, a drying step, and a surface treatment step that are included in a process for producing a polyacrylic acid (salt)-based water absorbent resin powder.

CITATION LIST

Patent Literature

[Patent Literature 1]
International Publication No. WO2011-126079 (Publication date: Oct. 13, 2011)

SUMMARY OF INVENTION

Technical Problem

However, a water absorbent resin is required to further improve in physical property. In particular, a water absorbent resin is required to improve in liquid permeability, preferably in liquid permeability and water absorbing speed, which are conflicting physical properties. The improvement in these two physical properties makes it possible to provide a water absorbent resin that is excellent in absorbency of a liquid and useful to sanitary materials such as a disposable diaper, a sanitary napkin, and a blood absorbent for medical use.

Meanwhile, hardly any improvement has been carried out with respect to a water absorbent resin from the viewpoint of obtaining a water absorbent resin that is excellent in heat retaining property. An improvement in heat retaining property of a water absorbent resin makes it possible to provide sanitary materials such as a disposable diaper that is highly comfortable to wear in all environments.

Solution to Problem

In order to solve the problems, inventors of the present invention found out, as a result of their diligent study, that closer control of a shape of water absorbent resin particles dramatically improves physical properties of a water absorbent resin. Then, the inventors proceeded with further study and found out a shape of a production apparatus that is capable of controlling a water absorbent resin so that the water absorbent resin can have an optimum shape. Finally, the inventors accomplished the present invention. That is, the present invention encompasses the following inventions:

[1] A gel grinding device to be used to produce a water absorbent resin, including: a screw; a feed opening; an extrusion opening; a porous plate; and a barrel, the barrel including at least one return preventing member provided on an inner surface thereof, and the barrel satisfying at least one of the following (1) and (2): (1) $0.05 \leq YH/N \leq 0.25$; and (2) $0.05 \leq YF/N \leq 0.25$ where YH is a height of the at least one return preventing member which height is obtained by cutting the barrel in a direction vertical to a direction in which a gel of the water absorbent resin is extruded; YF is a width of a top surface of the at least one return preventing member, the width being along a direction vertical to a direction in which the at least one return preventing member extends; and N is a diameter of an inner part of the barrel which diameter does not include the at least one return preventing member.

[2] The gel grinding device as set forth in [1], wherein the at least one return preventing member is helically provided on the inner surface of the barrel.

[3] The gel grinding device as set forth in [1], wherein the at least one return preventing member is provided on the inner surface of the barrel so as to be parallel to the screw.

[4] The gel grinding device as set forth in any one of [1] through [3], wherein the at least one return preventing member includes return preventing members which are wound from the feed opening to the extrusion opening of the gel grinding device and whose number ranges from one to seven.

[5] The gel grinding device as set forth in any one of [1] through [4], wherein the barrel and the porous plate are made of respective different materials.

[6] The gel grinding device as set forth in any one of [1] through [5], wherein the barrel is made of austenitic stainless steel.

[7] The gel grinding device as set forth in any one of [1] through [6], wherein the water absorbent resin is a polyacrylic acid (salt)-based water absorbent resin.

[8] A method for producing a polyacrylic acid (salt)-based water absorbent resin powder, including: a polymerization step of polymerizing an acrylic acid (salt)-based monomer aqueous solution; a gel grinding step, carried out during or after the polymerization, of carrying out gel grinding with respect to a hydrogel-like crosslinked polymer; and a drying step carried out after the gel grinding, in the gel grinding step, the hydrogel-like crosslinked polymer being ground by use of a gel grinding device recited in any one of [1] through [7], the hydrogel-like crosslinked polymer having a resin solid content of 10 wt % to 80 wt %.

[9] The method as set forth in [8], wherein $T/N^3$ ranges from 0.05 to 2.0 where T is an amount [g/hr] in which the gel grinding device treats a hydrogel per hour and $T/N^3$ is a treatment amount-to-inner diameter ratio [g/hr/mm$^3$] that is a treatment amount per unit time of the gel grinding device.

[10] The method as set forth in [8] or [9], wherein the hydrogel-like crosslinked polymer which is obtained in the gel grinding step and is particulate is dried under a condition where a through-flow belt-type dryer is used, a drying temperature is 150° C. to 250° C., and hot air blows in a vertical direction (an up-and-down direction) at an air velocity of 0.8 [m/s] to 2.5 [m/s].

[11] The method as set forth in any one of [8] through [10], wherein the barrel of the gel grinding device has a temperature of 40° C. to 120° C. while the gel grinding step is being carried out.

In order to solve the problems, the inventors of the present invention found out, as a result of their diligent study, that an absorbent body that is smaller in heat loss amount and excellent in heat retaining property can be obtained by causing a water absorbent resin powder to have a thermal conductivity equal to or smaller than a specific value. That is, the present invention encompasses the following inventions:

[1-1] A water absorbent resin powder containing a polyacrylic acid (salt)-based water absorbent resin as a main component, the water absorbent resin powder satisfying the following (A) to (C): (A) the water absorbent resin powder containing particles smaller than 150 μm in a ratio of 0 mass % to 4.5 mass % before an impact resistance test, and the water absorbent resin powder containing, in a ratio of 0 mass % to 4.5 mass %, particles smaller than 150 μm and increased by the impact resistance test; (B) the water absorbent resin powder having a saline flow conductivity (SFC) of not less than 10; and (C) the water absorbent resin powder having a thermal conductivity of not more than 125 [mW/(m·K)].

[1-2] The water absorbent resin powder as set forth in [1-1], wherein the water absorbent resin powder has an absorption capacity under load (AAP) of not less than 20 [g/g].

[1-3] The water absorbent resin powder as set forth in either one of [1-1] and [1-2], wherein the water absorbent resin powder has an internal gas bubbles ratio of 0% to 3.7%, the internal gas bubbles ratio being specified by the following equation:

(internal gas bubbles ratio) [%]={(true density)− (apparent density)}/(true density)×100

[1-4] The water absorbent resin powder as set forth in any one of [1-1] through [1-3], wherein the water absorbent resin powder contains at least one of a multivalent metal salt and inorganic microparticles.

[1-5] The water absorbent resin powder as set forth in any one of [1-1] through [1-4], wherein the water absorbent resin powder has a mass average particle diameter D50 of 350 μm to 460 μm, or the water absorbent resin powder has a particle size distribution having a logarithmic standard deviation of 0.25 to 0.45.

[1-6] The water absorbent resin powder as set forth in any one of [1-1] through [1-5], wherein the water absorbent resin powder contains, in a ratio of not more than 36 mass %, particles that pass through a sieve having a mesh size of 710 μm and do not pass through a sieve having a mesh size of 500 μm.

[1-7] The water absorbent resin powder as set forth in any one of [1-1] through [1-6], wherein the water absorbent resin powder has a surface tension of not less than 69.0 [mN/m].

Advantageous Effects of Invention

A gel grinding device in accordance with the present invention, which gel grinding device makes it possible to produce a water absorbent resin having a higher liquid permeability, or a higher liquid permeability and a higher water absorbing speed, yields an effect of providing sanitary materials such as a disposable diaper, a sanitary napkin, and a blood absorbent for medical use each having a more excellent physical property.

Further, a water absorbent resin powder in accordance with the present invention yields an effect of providing (i) an absorbent body that is excellent in absorbency of a liquid, realizes a high degree of wear comfort in all environments, and is excellent in heat retaining property and (ii) an absorbent article in which the absorbent body is used.

DESCRIPTION OF EMBODIMENTS

Figure 1:
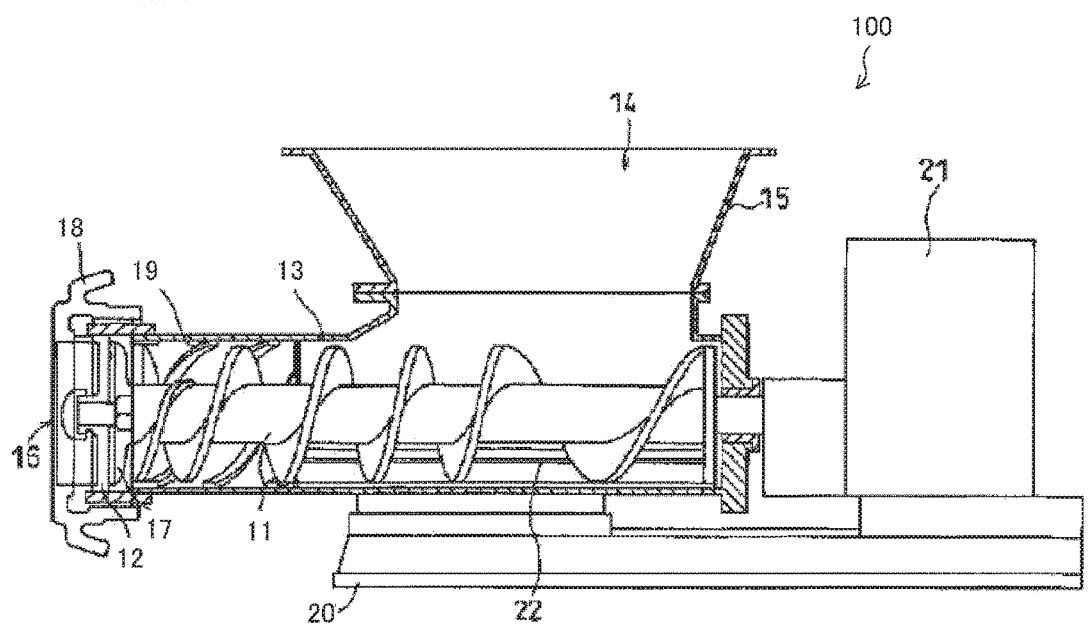
FIG. 1 is a cross-sectional view schematically illustrating an overall arrangement of a gel grinding device in accordance with the present invention.

Hereinafter, a gel grinding device for producing a water absorbent resin in accordance with the present invention, a method for producing a water absorbent resin by use of the gel grinding device, and a water absorbent resin to be obtained by the method will be described in detail. It should be noted that the scope of the present invention is not limited to the description and can be embodied with modifications other than the following exemplary embodiments but not departing from the gist of the present invention. More specifically, the present invention shall not be construed as being limited to the following embodiments, may be modified in many ways within the scope of the following claims. The technical scope of the present invention can encompass any modifications obtainable by appropriately combining technical means disclosed in different embodiments.

Note that in the present invention, "weight" is synonymous with "mass".

[1] Definitions of Terms (1-1) "Water Absorbent Resin"

The term "water absorbent resin" as used in the present invention means a water-swelling and water-insoluble gelatinized polymer. Note that "water-swelling" indicates that CRC (water absorption capacity without load) defined in ERT442.2-02 is 5 [g/g] or higher, and "water-insoluble" indicates that Ext (water soluble component) defined in ERT470.2-02 is 0 wt % to 50 wt %.

The water absorbent resin can be designed as appropriate according to its purpose of use, and is not limited to a particular one. The water absorbent resin is preferably a hydrophilic crosslinked polymer which has been obtained by crosslinking and polymerizing unsaturated monomers each of which has a carboxyl group. Moreover, the water absorbent resin is not limited to a form in which the water absorbent resin is wholly (i.e., 100 wt %) a polymer, and can be a water absorbent resin that is surface-crosslinked or a water absorbent resin composition that contains an additive and the like within a range in which the above described performance is maintained.

The "water absorbent resin" of the present invention is a resin that has been obtained by pulverizing the hydrophilic crosslinked polymer and is in the form of powder. For convenience, a water absorbent resin that has not been surface-treated or surface-crosslinked is herein referred to as "water absorbent resin particles", and a water absorbent resin that has been surface-treated or surface-crosslinked is herein referred to as a "water absorbent resin powder". Further, either a water absorbent resin that varies in form obtained in each step (examples of the form of the water absorbent resin include a sheet form, a fiber form, a film form, a gel form, and the like) or a water absorbent resin composition that contains an additive and the like is herein collectively referred to as the "water absorbent resin".

(1-2) "Polyacrylic Acid (Salt)"

The term "polyacrylic acid (salt)" as used in the present invention means a polymer that has a graft component as appropriate and contains, as main components, recurring units constituted by an acrylic acid, a salt thereof (the acrylic acid and the salt thereof are herein collectively referred to as acrylic acid (salt)), or a combination thereof. More specifically, the "polyacrylic acid (salt)" as used in the present invention is a polymer in which acrylic acid (salt) essentially accounts for 50 mol % to 100 mol % in the total monomer content (except an internal crosslinking agent) to be polymerized, preferably a polymer in which acrylic acid (salt) accounts for 70 mol % to 100 mol % in the total monomer content, still more preferably a polymer in which acrylic acid (salt) accounts for 90 mol % to 100 mol % in the total monomer content, and particularly preferably a polymer in which acrylic acid (salt) accounts for substantially 100 mol % in the total monomer content. Further, the polyacrylic acid (salt) which is used as a polymer essentially contains a water-soluble salt, and the water-soluble salt (neutralized salt) contains, as a main component, preferably a monovalent salt, more preferably an alkali metal salt or ammonium salt, still more preferably an alkali metal salt, and particularly preferably a sodium salt.

(1-3) "EDANA" and "ERT"

The term "EDANA" is an abbreviation for European Disposables and Nonwovens Associations. The term "ERT" is an abbreviation for EDANA Recommended Test Methods, which is the European-standard (actually the global-standard) method of measuring water absorbent resins. The ERT is a method of measuring the physical properties of water absorbent resins, and unless otherwise specified, the measurement is carried out in the present invention in conformity with a master copy of the ERT (Known Literature: 2002 revised version).

(a) "CRC" (ERT441.2-02)

"CRC" is an abbreviation for Centrifuge Retention Capacity, and means water absorption capacity (herein referred to as "water absorption capacity") without load. Specifically, "CRC" is water absorption capacity (unit; [g/g]) measured when 0.200 g of a water absorbent resin in a nonwoven fabric bag is allowed to freely swell in a large excess of a 0.9 wt % sodium chloride aqueous solution for 30 minutes and then drained by a centrifugal separator.

Note that CRC of a hydrogel-like crosslinked polymer (herein referred to as "gel CRC") is measured under a condition where a weight of a sample and a free swelling time are changed to 0.4 g and 24 hours, respectively. Note also that in the measurement, a weight of a water absorbent resin is calculated by use of a value which is 0.01 times a value obtained by multiplying the weight of the sample and a resin solid content (wt %) of the hydrogel-like crosslinked polymer.

(b) "AAP" (ERT442.2-02)

"AAP" is an abbreviation for Absorbency Against Pressure, and means water absorption capacity under load. Specifically, "AAP" is water absorption capacity (unit; [g/g]) measured when 0.900 g of a water absorbent resin has swollen a 0.9 wt % sodium chloride aqueous solution for 1 hour under a load of 2.06 kPa (0.3 psi, 21 [g/cm$^2$]). Note that Absorption Under Pressure in ERT442.2-02 is substantially identical with AAP. Moreover, measurement described herein is carried out under conditions where the load is changed to 4.83 kPa (0.7 psi, 49 [g/cm$^2$]).

(c) "Ext" (ERT470.2-02)

"Ext" is an abbreviation for Extractables, and means a water soluble component (water soluble component amount). Specifically, "Ext" is a dissolved polymer amount (unit; wt %) measured when (i) 1.000 g of a water absorbent resin is added to 200 mL of a 0.9 wt % sodium chloride aqueous solution and (ii) stirring is carried out for 16 hours. Note that the dissolved polymer amount is measured by pH titration.

Note that a water soluble component of a hydrogel-like crosslinked polymer (herein referred to as "gel Ext") is measured under a condition where a weight of a sample and a stirring time are changed to 5.0 g and 24 hours, respectively. Note also that in the measurement, a weight of a water absorbent resin is calculated by use of a value which is 0.01 times a value obtained by multiplying the weight of the sample and a resin solid content (wt %) of the hydrogel-like crosslinked polymer.

(d) "PSD" (ERT420.2-02)

"PSD" is an abbreviation for Particle Size Distribution, and means a particle size distribution measured by sieve classification. Moreover, a weight average particle diameter (D50) and a particle diameter distribution width are measured according to a method similar to a method disclosed in the specification of European Patent No. 0349240, page 7, lines 25 through 43, "(1) Average Particle Diameter and Distribution of Particle Diameter". Note that a method for measuring PSD of a hydrogel-like crosslinked polymer is described later. Furthermore, a standard sieve (mesh size) for use in measurement of a particle size can be added as appropriate according to a particle size of an object. For example, a standard sieve having a mesh size of, for example, 710 μm or 610 μm only needs to be added. Moreover, for, for example, a measurement condition that is not disclosed in the specification of European Patent No. 0349240, European Patent No. 1594556 can be referred to as appropriate.

(e) "Residual Monomers" (ERT410.2-02)

"Residual monomers" mean amounts of monomers left in a water absorbent resin (herein referred to as "residual monomers"). Specifically, "Residual Monomers" are a dissolved monomer amount (unit; ppm) measured after adding 1.0 g of a water absorbent resin to 200 mL of a 0.9 wt % sodium chloride aqueous solution, and carrying out stirring by use of a stirrer chip of 35 mm at 500 rpm for 1 hour. The dissolved monomer amount is measured by use of HPLC (high performance liquid chromatography). Note that a residual monomer of a hydrogel-like crosslinked polymer is measured under a condition where a weight of a sample and a stirring time are changed to 2 g and three hours, respectively, and an obtained measured value is converted to a value (unit; ppm) expressed in terms of a weight per resin solid content of the hydrogel-like crosslinked polymer.

(f) "Moisture Content" (ERT430.2-02)

"Moisture Content" means moisture content of a water absorbent resin. Specifically, "Moisture Content" is a value (unit; wt %) calculated from drying loss caused by drying 1 g of a water absorbent resin at 105° C. for 3 hours. Note that, in the present invention, a drying temperature is changed to 180° C., one sample is measured five times, and an average of the five measurements is employed. Further, a moisture content of a hydrogel-like crosslinked polymer is measured under a condition where a weight of a sample, a drying temperature, and a drying time are changed to 2 g, 180° C., and 16 hours, respectively. Furthermore, a value calculated by {100−moisture content (wt %)} is "resin solid content" in the present invention, and the value is applicable to both a water absorbent resin and a hydrogel-like crosslinked polymer.

(g) "Density" (ERT460.2-02)

"Density" means bulk specific gravity of a water absorbent resin. Specifically, "Density" is weight (unit; [g/mL]) of a water absorbent resin measured by introducing 100 g of the water absorbent resin into a device defined by EDANA, and causing the water absorbent resin to freely fall into a 100 mL container to fill the container.

(h) "Flow Rate" (ERT450.2-02)

"Flow Rate" means flow speed of a water absorbent resin. Specifically, "Flow Rate" is a time (unit; sec) required for discharge of 100 g of a water absorbent resin introduced into a device defined by EDANA from an outlet of a lowest part of the device.

(1-4) "Liquid Permeability"

The term "liquid permeability" as used in the present invention means the degree of flowing of a liquid passing through a space between particles of swollen gel under load or without load. The "liquid permeability" is measured typically as SFC (Saline Flow Conductivity) or GBP (Gel Bed Permeability).

"SFC (Saline Flow Conductivity)" herein means a liquid permeability of a 0.69 wt % sodium chloride aqueous solution relative to a water absorbent resin under a load of 2.07 kPa, and is measured according to the SFC test method disclosed in U.S. Pat. No. 5,669,894. Moreover, "GBP" herein means a liquid permeability of a 0.69 wt % sodium chloride aqueous solution relative to a water absorbent resin which is under load or is allowed to freely swell, and is measured according to the GBP test method disclosed in the International Publication No. WO 2005/016393.

(1-5) "FSR"

The term "FSR" as used in the present invention is an abbreviation for Free Swell Rate, and means a water absorbing speed (free swell rate). Specifically, "FSR" is speed (unit; [g/(g·s)]) at which 1 g of a water absorbent resin absorbs 20 g of a 0.9 wt % sodium chloride aqueous solution.

(1-6) "Gel Grinding"

The term "gel grinding" as used in the present invention means an operation in which a hydrogel-like crosslinked polymer obtained in a polymerization step (preferably aqueous solution polymerization, unstirred aqueous solution polymerization (standing aqueous solution polymerization), and particularly preferably belt polymerization) is made smaller in size by use of a gel grinding device of the present invention so as to be prepared in a desired shape. Specifically, "gel grinding" means a technique in which a hydrogel-like crosslinked polymer obtained in a polymerization step is subjected to gel grinding by use of a gel grinding device of the present invention so as to have a weight average particle diameter (D50) of 300 μm to 3,000 μm and more preferably a weight average particle diameter (D50) of 350 μm to 2,000 μm, and a particle size distribution having a logarithmic standard deviation (σζ) preferably of 0.2 to 1.0.

Note that a shape of a hydrogel-like crosslinked polymer to be obtained may vary depending on a type of a polymerization device. For example, polymerization and gel grinding are continuously carried out in a single device in the case of kneader polymerization as opposed to the case of unstirred aqueous solution polymerization (standing aqueous solution polymerization, especially belt polymerization) in which gel grinding is carried out after polymerization. Note, however, that gel grinding only needs to be carried out in a gel grinding device of the present invention after polymerization regardless of a polymerization method.

(1-7) "Weight Average Molecular Weight of Water Soluble Component"

The term "weight average molecular weight of a water soluble component" as used in the present invention means a value (unit; daltons/hereinafter abbreviated as [Da]) measured by use of GPC (gel permeation chromatography) for a weight average molecular weight of a component that is dissolved when a water absorbent resin is added to a water solvent (a water soluble component). That is, "weight average molecular weight of a water soluble component" is a result of measurement by use of GPC of a solution obtained by the measurement method described in the above (1-3) (c) "Ext". Note that a weight average molecular weight of a water soluble component of a hydrogel-like crosslinked polymer is measured under a condition where a weight of a sample that has been grain-refined so as to have a particle diameter of not more than 5 mm, and further grain-refined so as to have a particle diameter of 1 mm to 3 mm is changed to 5.0 g, and a stirring time is changed to 24 hours.

(1-8) "Gel Grinding Energy" (GGE and GGE (2))

The term "gel grinding energy" as used in the present invention means mechanical energy per unit weight (unit weight of a hydrogel-like crosslinked polymer), which mechanical energy is necessary for a gel grinding device to gel grind a hydrogel-like crosslinked polymer. The gel grinding energy does not include energy with which to heat or cool a jacket, or energy of water and steam to be introduced. Note that "Gel Grinding Energy" is abbreviated as "GGE". In a case where the gel grinding device is driven by a three-phase alternating current power supply, the GGE is calculated based on the following Equation (1):

$$GEE[J/g] = \{\sqrt{3} \times voltage \times current \times power\ factor \times motor\ efficiency\} / \{weight\ of\ hydrogel\text{-}like\ crosslinked\ polymer\ to\ be\ introduced\ into\ gel\ grinding\ device\ per\ second\} \quad \text{Equation (1)}$$

The "power factor" and the "motor efficiency" are each a value which is unique to the gel grinding device and changes depending on, for example, an operation condition of the gel grinding device and which ranges from 0 to 1. In a case where the gel grinding device is driven by a single-phase alternating current power supply, the GGE can be calculated by replacing "$\sqrt{3}$" with "1" in the above Equation (1). Note that a unit of a voltage is [V], a unit of a current is [A], and a unit of weight of a hydrogel-like crosslinked polymer is [g/s]. Note also that it is also possible to carry out gel grinding with respect to a hydrogel-like crosslinked polymer by use of a plurality of gel grinding devices. In this case, it is only necessary to calculate GGE for each of the plurality of gel grinding devices.

Since the mechanical energy to be applied to the hydrogel-like crosslinked polymer is one of the important factors, the gel grinding energy is preferably calculated by subtracting a current value of the gel grinding device during idling from a current value of the gel grinding device during gel grinding. In particular, gel grinding that is carried out by use of a plurality of gel grinding devices increases a sum of current values of the plurality of gel grinding devices during idling. Thus, it is suitable to calculate the gel grinding energy by subtracting the current values of the plurality of gel grinding devices during idling from current values of the plurality of gel grinding devices during gel grinding. In this case, the gel grinding energy is calculated based on the following Equation (2):

$$GGE(2)[J/g] = \{\sqrt{3} \times voltage \times (current\ during\ gel\ grinding - current\ during\ idling) \times power\ factor \times motor\ efficiency\} / \{weight\ of\ hydrogel\text{-}like\ crosslinked\ polymer\ to\ be\ introduced\ into\ gel\ grinding\ device\ per\ second\} \quad \text{Equation (2)}$$

Note that GGE calculated based on Equation (2) is denoted as GGE (2) so as to be distinguished from the GGE calculated based on Equation (1).

As the "power factor" and the "motor efficiency" in Equation (2), values thereof during gel grinding are employed. Note that, since a current value during idling is small, the power factor and the motor efficiency during idling are approximately defined as in Equation (2). For example, in a case where an amount of the hydrogel-like crosslinked polymer to be continuously fed by a quantitative feeder is [t/hr], the "weight of hydrogel-like crosslinked polymer to be introduced into gel grinding device per second [g/s]" in each of Equations (1) and (2) refers to a value obtained by converting [t/hr] into [g/s].

(1-9) Others

In this specification, a range "X to Y" means "not less than X and not more than Y". "t (ton)", which is a unit of weight, means "metric ton". Moreover, unless otherwise specified, "ppm" means "ppm by weight". "weight" is synonymous with "mass", "wt %" is synonymous with "mass %", and "parts by weight" is synonymous with "parts by mass". Further, " . . . acid (salt)" means " . . . acid and/or salt thereof", and "(meth)acrylic" means "acrylic and/or methacrylic". In addition, "main component" means accounting for not less than 51% of the whole.

[2] Gel Grinding Device

A gel grinding device in accordance with the present invention is a device to be used to obtain a hydrogel-like crosslinked polymer in a desired shape (herein referred to as a "particulate hydrogel") by grain-refining a hydrogel-like crosslinked polymer that is being polymerized or has been polymerized.

Conventional gel grinding is an operation which is carried out so as to facilitate drying and in which a surface area is increased by reducing a size by addition of a shearing force and a compressive force, and it has been considered preferable that grinding means allows a hydrogel to be cut or cracked so that the hydrogel is not kneaded (see Prior Art Documents mentioned in Patent Literature 1 (e.g., U.S. Pat. Nos. 7,694,900, 6,565,768, 6,140,395, etc.)). Patent Literature 1 succeeds in increasing liquid permeability and water absorbing speed by causing gel grinding energy or a weight average molecular weight of a water soluble component to meet a specific gel grinding condition and a specific drying condition, or drying, under a specific drying condition, a gel having a specific weight average particle diameter and a specific particle size distribution.

The inventors of the present invention found, as a result of their diligent study, that a liquid permeability of, preferably both the liquid permeability and a water absorbing speed of a water absorbent resin to be obtained is improved in a case where a gel grinding device having a specific shape is further used in a gel grinding step, which is a step of a process for producing a water absorbent resin, to grind a hydrogel so that the hydrogel is kneaded. Further, the inventors of the present invention found that the water absorbent resin to be obtained can also have high physical properties concerning liquid permeability and water absorbing speed. The following description specifically discusses the gel grinding device in accordance with the present invention.

(Arrangement of Gel Grinding Device)

FIG. 1 is a cross-sectional view schematically illustrating an overall arrangement of a gel grinding device 100 in accordance with the present invention. The gel grinding device 100 is used to obtain a particulate hydrogel in a desired shape. The gel grinding device 100 is used particularly in a gel grinding step, which is carried out between a polymerization step and a drying step, during production of a water absorbent resin.

As illustrated in FIG. 1, the gel grinding device 100 includes a screw 11, a porous plate 12, a barrel 13, a feed opening 14, a hopper 15, an extrusion opening 16, a rotary blade 17, a ring 18, at least one return preventing member 19, a base 20, a motor and speed reducer 21, and others.

According to the gel grinding device 100, the screw 11 is provided inside of the barrel 13, which has a cylindrical shape. The barrel 13 has one end at which (i) the extrusion opening 16 via which to extrude a hydrogel and subject the hydrogel to gel grinding is provided and (ii) the porous plate 12 is provided short of the extrusion opening 16 in a direction in which the hydrogel is extruded. The barrel 13 has the other end at which the motor and speed reducer 21 which rotates the screw 11, a driving system, etc. are provided. The base 20, which lies under the barrel 13, makes it possible to stably provide a screw extruder. Meanwhile, above the barrel 13, the feed opening 14 via which to feed a hydrogel is provided, and the hopper 15 is provided so as to facilitate the feed of the hydrogel.

The gel grinding device 100 preferably maintains its durability even in a case where it is used for not less than 8000 hours per year. Thus, the gel grinding device 100 is preferably arranged such that connecting parts of members of the gel grinding device 100 are not easily disconnected from each other even under a motive power.

(Screw 11 and Barrel 13)

Figure 2:
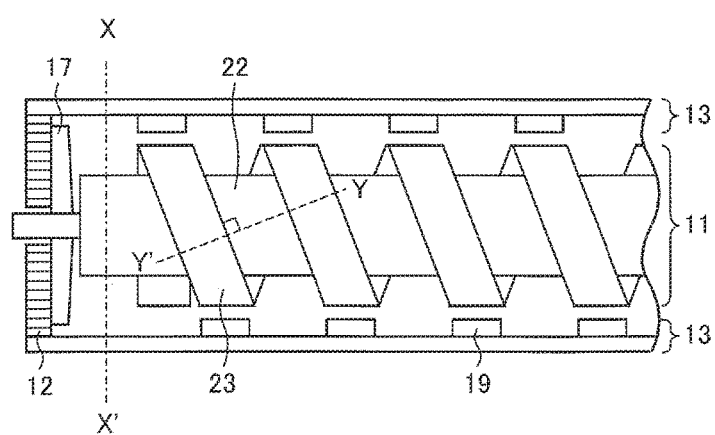
FIG. 2 is a cross-sectional view schematically illustrating a vicinity of an extrusion opening of the gel grinding device in accordance with the present invention.

FIG. 2 is a cross-sectional view schematically illustrating a vicinity of the extrusion opening 16 of the gel grinding device 100. The screw 11 mainly includes a rotating shaft 22 and a flight section 23. The flight section 23 is helically provided while centering on the rotating shaft 22. The number of windings of the flight section 23 on the rotating shaft 22 refers to the number of times the flight section 23 is wound on the rotating shaft 22 from one end to the other end of the rotating shaft 22. The number of windings of the flight section, which number is not particularly limited, is preferably not less than three and particularly preferably not less than four. Further, the flight section 23 can have a helix that is a single helix, a double helix, or a triple helix, and the number of flight sections 23 provided on the rotating shaft 22 is not particularly limited.

The flight section 23 is wound on the rotating shaft 22 in a direction opposite from a direction in which the rotating shaft 22 rotates. That is, in FIG. 1, in a case where the gel grinding device in accordance with the present invention is seen in a direction from the motor and speed reducer 21 toward the extrusion opening 16 and the rotating shaft 22 rotates clockwise, the flight section 23 is wound counterclockwise on the rotating shaft 22.

The barrel 13 is not particularly limited in shape or size provided that the barrel 13 has a cylindrical inner surface that corresponds to a shape of the screw 11. The barrel 13 is provided with the at least one return preventing member 19. The at least one return preventing member 19 is not particularly limited provided that the return preventing member 19 has a structure that can prevent return of a hydrogel. The at least one return preventing member 19 can be a helical or concentric belt-like protrusion that is provided on an inner wall of the barrel 13, or can be striped, granular, spherical, or angular protrusions that are provided on the inner wall of the barrel 13 so as to be parallel to the screw 11. The at least one return preventing member 19 which is provided on the inner wall of the barrel 13 yields an effect of preventing return of a hydrogel. Note that "the at least one return preventing member 19 is parallel to the screw 11" herein only needs to mean that the at least one return preventing member 19 is substantially parallel to the screw 11. That is, from an inlet toward an outlet of the gel grinding device, the screw 11 side surface of the at least one return preventing member 19 and the barrel 13 side surface of the flight section 23 of the screw 11 form an angle falling within a range preferably of 0° to 10°, preferably of 0° to 5°, and most preferably of 0°.

In a case where the at least one return preventing member 19 is helically provided inside of the barrel 13, the at least one return preventing member 19 is provided in the barrel 13 in a direction identical to a direction in which the rotating shaft 22 rotates. That is, in FIG. 1, in a case where the gel grinding device in accordance with the present invention is seen in a direction from the motor and speed reducer 21 toward the extrusion opening 16 and the rotating shaft 22 rotates clockwise, the at least one return preventing member 19 is formed clockwise in the barrel.

In a case where the at least one return preventing member 19 is helically provided inside of the barrel 13, the number of windings of the at least one return preventing member 19 from the feed opening 14 to the extrusion opening 16 is herein referred to as a "barrel thread number". The barrel thread number of the present invention preferably ranges from 1 to 16, more preferably from 1 to 8, still more preferably from 1 to 7, and most preferably from 1 to 4. In a case where the barrel thread number of the present invention is more than 16, a gel with which a gap between respective return preventing members of the at least one return preventing member is clogged and which resides in the gap may deteriorate.

Further, the "protrusion", which is the shape of the at least one return preventing member 19, is not limited to a protruding shape, and means also encompassing a recessed shape (surrounding protruding shape members that form the recessed shape) obtained in a case where a groove is formed in the barrel 13 as a matter of convenience of production of the device.

Figure 3:
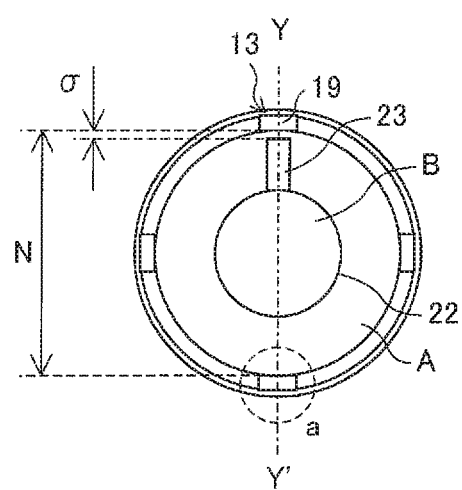
FIG. 3, which is obtained by cutting a screw and a barrel along X-X' in FIG. 2, is a cross-sectional view of a screw and a barrel which have been cut in a direction vertical to a direction in which a hydrogel is extruded.

FIG. 3, which is obtained by cutting a screw along X-X' in FIG. 2, is a cross-sectional view of the screw 11 and the barrel 13 which have been cut in a direction vertical to a direction in which a hydrogel is extruded. In FIG. 3, a maximum inner diameter which prevents a contact between the at least one return preventing member 19 and the screw 11 which is provided inside of the barrel 13, is N (herein also referred to as an "inner diameter N"), an area of a surface whose inner diameter is N is A (herein also referred to as a "cross-sectional area A"), and an area of a surface constituted by the rotating shaft 22 and the flight section 23 is B (herein also referred to as a "cross-sectional area B"). The rotating shaft 22 has a diameter falling within a range preferably of 25 [mm] to 400 [mm] and more preferably of 40 [mm] to 300 [mm]. Further, a "screw cross-sectional area ratio", which herein refers to a ratio of the cross-sectional area B to the cross-sectional area A, is expressed as "B/A".

Assume that a gap between the at least one return preventing member 19 which is provided inside of the barrel 13 and the flight section 23 is σ (herein also referred to as a "clearance σ"). The clearance σ is preferably 0.5 [mm] to 7 [mm], more preferably 1 [mm] to 5 [mm], and most preferably 1 [mm] to 3 [mm]. In a case where the clearance σ is smaller than 0.5 [mm], the screw and the barrel may contact each other during the gel grinding. In a case where the clearance σ is greater than 7 [mm], a gel is insufficiently sheared, so that no water absorbent resin that has intended performance may be obtained.

Figure 4:
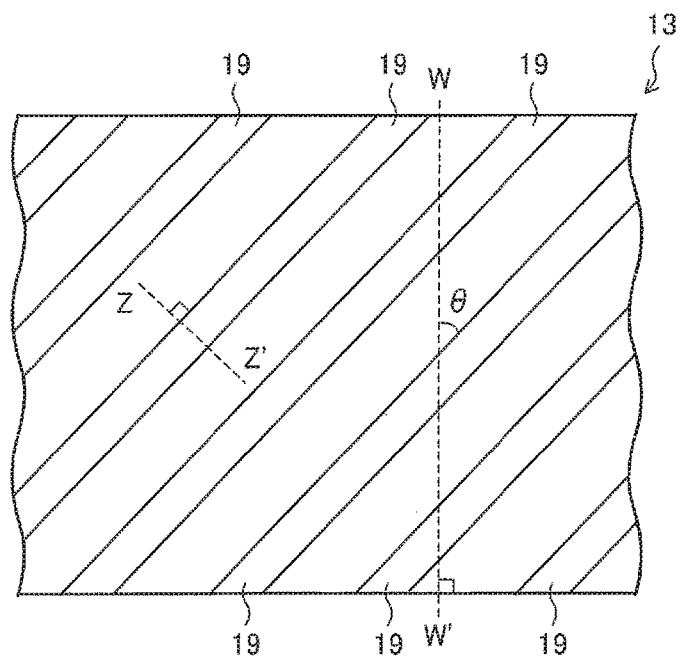
FIG. 4 is a view of development of the barrel that is cut along plane Y-Y' in FIG. 3.
Figure 5:
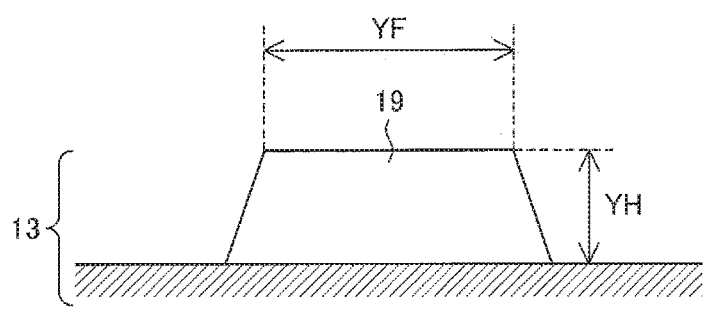
FIG. 5, which is a view in which the barrel is cut along plane Z-Z' in FIG. 4, is a cross-sectional view schematically illustrating a return preventing member.

Next, an arrangement of the barrel 13 of the present invention is further described with reference to FIGS. 4 through 6. FIG. 4 is a view of planar development of the barrel in which the screw is cut along plane Y-Y' in FIG. 3. Plane W-W' in FIG. 4 is vertical to plane Y-Y' in FIG. 3. In a case where the at least one return preventing member 19 is helically provided inside of the barrel 13, the at least one return preventing member 19 is preferably provided so as to be at an angle of θ with respect to the plane W-W' (see FIG. 4). The angle θ is herein referred to as a "barrel set angle." The barrel set angle θ of the present invention ranges preferably from 10° to 90°, more preferably from 20° to 60°, and still more preferably from 30° to 45°. In a case where θ is smaller than 10°, an effect of preventing return of a gel is too strong, so that an insufficient shearing force may be applied to the gel. In a case where θ is greater than 90°, no effect of preventing return of a gel may be exhibited. FIG. 5, which is a view in which the barrel is cut along plane Z-Z' in FIG. 4 and one of the at least one return preventing member 19 is enlarged, is a cross-sectional view schematically illustrating two flight sections 23. A "barrel ridge height (YH)" herein refers to a distance from the inner surface of the barrel 13 to an upper surface of the at least one protruding return preventing member 19. The barrel ridge height YH, whose optimum value varies depending on the inner diameter N, ranges preferably from 4 [mm] to 40 [mm] and more preferably from 7 [mm] to 30 [mm]. The barrel ridge height YH with respect to the inner diameter N (YH/N) has a value ranging from 0.05 to 0.25 and more preferably from 0.05 to 0.2. In a case where the YH/N is greater than 0.25, a water absorbent resin is insufficiently kneaded, so that no intended physical properties of the water absorbent resin may be obtained. The YH/N which ranges from 0.05 to 0.25 yields an effect of improving a liquid permeability of, preferably both the liquid permeability and a water absorbing speed of a water absorbent resin to be obtained. The YH/N which ranges from 0.05 to 0.25 also yields an effect of allowing a water absorbent resin to be obtained to have a smaller thermal conductivity.

A "barrel ridge width YF" herein refers to a width of a surface of the at least one return preventing member 19 which surface is the closest to the screw 11, the width being along a direction vertical to a direction in which the at least one return preventing member 19 extends. The barrel ridge width YF, whose optimum value varies depending on the inner diameter N, ranges preferably from 4 [mm] to 40 [mm] and more preferably from 8 [mm] to 30 [mm]. The barrel ridge width YF with respect to the inner diameter N (YF/N) has a value ranging from 0.05 to 0.25 and more preferably from 0.05 to 0.2. In a case where the YF/N is greater than 0.25, a water absorbent resin is excessively kneaded, so that no intended physical properties of the water absorbent resin may be obtained. The YF/N which ranges from 0.05 to 0.25 yields an effect of improving a liquid permeability of, preferably both the liquid permeability and a water absorbing speed of a water absorbent resin to be obtained. The YF/N which ranges from 0.05 to 0.25 also yields an effect of allowing a water absorbent resin to be obtained to have a smaller thermal conductivity.

Next, a width of a top surface of the flight section 23 which top surface does not contact the rotating shaft 22, the width being along a direction vertical to a direction in which the flight section 23 extends, is F (herein also referred to as the "flight width F"). The flight width with respect to the inner diameter N (F/N) has a value preferably of 0.03 to 0.20, more preferably of 0.05 to 0.15, and most preferably of 0.07 to 0.13.

Figure 6:
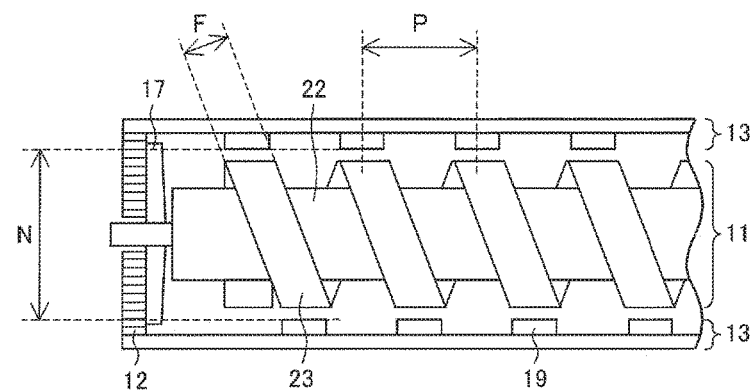
FIG. 6 is a cross-sectional view schematically describing an inner diameter N of the barrel, a flight width F of the screw, and a pitch length P.

Further, in FIG. 6, a distance between respective centers of any adjacent flight widths F is P (herein also referred to as the "pitch length P"). The pitch length P, which is equivalent to one winding from an end of the screw on the gel grinding device outlet side, with respect to the inner diameter N (P/N) has a value preferably of 0.15 to 0.68, more preferably of 0.20 to 0.50, and most preferably of 0.25 to 0.40. Further, in a case where a single screw has a plurality of pitch lengths, any one of the plurality of pitch lengths preferably falls within the above range, a pitch length of either one of the first winding and the second winding more preferably falls within the above range, and a pitch length of the first winding most preferably falls within the above range.

In order that a water absorbent resin to be obtained by use of the gel grinding device in accordance with the present invention improves in physical property, it is only necessary that the YH/N satisfy 0.05≤YH≤0.25 and/or the YF/N satisfy 0.05≤YF≤0.25, and it is more preferable that the YH/N satisfy 0.05≤YH≤0.25 and the YF/N satisfy 0.05≤YF≤0.25. According to the gel grinding device in accordance with the present invention, at least one of the YH/N which satisfies 0.05≤YH≤0.25 and the YF/N which satisfies 0.05≤YF≤0.25 yields an effect of producing a water absorbent resin having a higher liquid permeability, preferably both a higher liquid permeability and a higher water absorbing speed. Further, at least one of the YH/N which satisfies 0.05≤YH≤0.25 and the YF/N which satisfies 0.05≤YF≤0.25 yields an effect of producing a water absorbent resin having a smaller thermal conductivity.

A material of which the screw 11 and the barrel 13 of the present invention are made is not particularly limited, and the material is preferably stainless steel and still more preferably austenitic stainless steel from the viewpoint of corrosion resistance. Specifically, the screw 11 and the barrel 13 are made preferably of SUS304.

Figure 7:
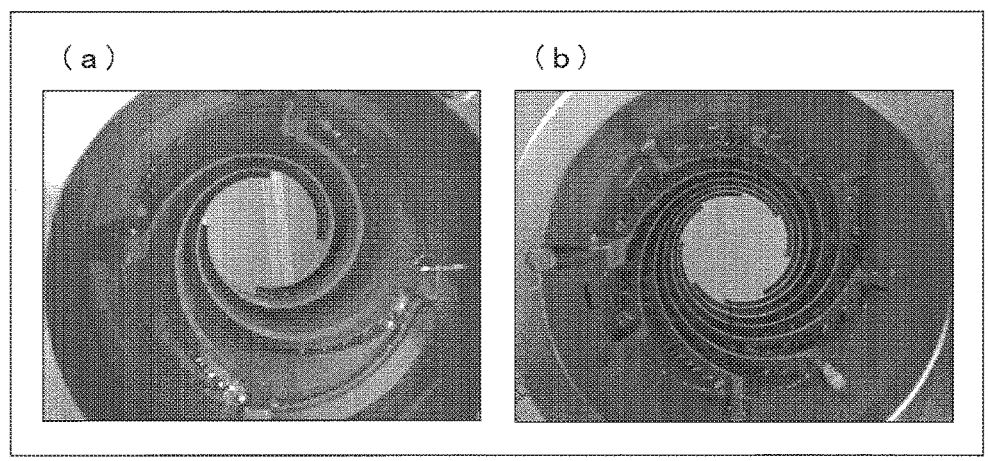
FIG. 7 shows an example of a barrel that can be used in the gel grinding device in accordance with the present invention.

FIG. 7 shows an example of a barrel that can be used in the gel grinding device in accordance with the present invention. FIG. 7 is a view in which the barrel is seen in a direction from the extrusion opening 16 (shown in FIG. 1) toward the motor and speed reducer 21 (shown in FIG. 1). (a) of FIG. 7 is a view of barrel no. B88-478 used in Examples of the present invention, and (b) of FIG. 7 is a view of barrel no. B88-874 used in Examples of the present invention.

(Porous Plate 12)

The porous plate 12 of the present invention is a member that is provided in an exit part of the gel grinding device in accordance with the present invention via which exit part to extrude a hydrogel in the barrel 13. A thickness and a pore diameter or an aperture ratio of the porous plate 12 can be appropriately selected according to, for example, a treatment amount per unit time of the gel grinding device or a shape of a hydrogel, and is not particularly limited. The porous plate has a thickness (herein also referred to as a "die thickness") preferably of 3.5 mm to 40 mm, more preferably of 8 mm to 30 mm, and most preferably of 10 mm to 25 mm. Further, the porous plate has a pore diameter (herein also referred to as a "die pore diameter") preferably of 3.2 mm to 30 mm and more preferably of 7.5 mm to 25 mm. In addition, the porous plate has an aperture ratio (herein also referred to as a "die aperture ratio") preferably of 20% to 80% and more preferably of 30% to 55%. In a case where a plurality of porous plates that differ in die pore diameter (mm) are used, a simple average value of pore diameters of the plurality of porous plates is set as a pore diameter of the porous plate of the gel grinding device. Note that a pore of the porous plate, which pore preferably has a circular shape, is not particularly limited. In a case where the pore has a shape different from the circular shape (e.g., a quadrangular shape, an elliptical shape, a slit shape, or the like), the pore diameter (mm) is obtained by converting an aperture area of the pore having the shape different from the circular shape into an aperture area of the pore having the circular shape.

In a case where the porous plate falls under at least one of the following cases: (i) a case where "the porous plate has a thickness smaller than 3.5 mm", (ii) a case where "the porous plate has a die pore diameter greater than 30 mm"; and (iii) a case where "the porous plate has a die aperture ratio greater than 80%, it may be impossible to apply a sufficient shearing force and a sufficient compressive force to a hydrogel. Contrary to this, in a case where the porous plate falls under at least one of the following cases: (i) a case where "the porous plate has a thickness greater than 40 mm", (ii) a case where "the porous plate has a die pore diameter smaller than 3.2 mm"; and (iii) a case where "the porous plate has a die aperture ratio smaller than 20%, an excessive shearing force and an excessive sufficient compressive force may be applied to a hydrogel, so that a water absorbent resin may deteriorate in physical property. Thus, it is not preferable that the porous plate fall under at least one of the above cases.

The porous plate 12 of the present invention is preferably made of a material (metal) that is different from a material (metal) of which the screw 11 and the barrel 13 are made. In a case where (i) the porous plate 12 and (ii) the screw 11 and the barrel 13 are made of a single material, the device may break due to, for example, seizing. More specifically, the porous plate 12 is preferably made of a metal that allows the porous plate 12 to have a higher hardness by quenching (a heat treatment). Note that the barrel 13 is preferably made of austenitic stainless steel.

(Materials for Rotating Shaft 22 and Bearing Section)

The gel grinding device in accordance with the present invention can include a bearing section. The "bearing section" herein refers to a member that is provided in a space between a plate of a die and the rotating shaft. (i) A part which the rotating shaft 22 of and the bearing section of the present invention each contact and (ii) the rotating shaft and the bearing section are made preferably of respective different materials and more preferably of respective metals that differ in material. In a case where (i) the part which the rotating shaft 22 and the bearing section each contact and (ii) the rotating shaft 22 and the bearing section are made of a single material, the device may break due to, for example, seizing, and/or metal powder may contaminate a product.

(Rotation Rate of Rotating Shaft 22 and Peripheral Rotation Speed of Flight Section 23)

A rotation rate of the rotating shaft 22 of the present invention cannot be generally defined. This is because a peripheral rotation speed of a rotational blade varies depending on the inner diameter of the barrel 13. Note, however, that the rotating shaft 22 has a rotation rate preferably of 60 rpm to 500 rpm, more preferably of 80 rpm to 400 rpm, and still more preferably of 100 rpm to 200 rpm. The rotating shaft 22 which has a rotation rate of less than 60 rpm may fail to apply a shearing force and a compressive force each required for gel grinding. Meanwhile, the rotating shaft 22 which has a rotation rate of more than 500 rpm applies an excessive shearing force and an excessive compressive force to a hydrogel. This may cause a deterioration in physical property of a water absorbent resin to be obtained, and/or increase a load on the gel grinding device in accordance with the present invention and consequently damage the gel grinding device.

(Operating Temperature of Gel Grinding Device)

The gel grinding device 100 of the present invention operates at a temperature preferably of 40° C. to 120° C. and more preferably of 60° C. to 100° C. so as to prevent, for example, adhesion thereto of a hydrogel. Further, the gel grinding device of the present invention preferably includes, for example, a heater and/or a thermoregulator.

(Temperature of Hydrogel to be Subjected to Gel Grinding by Gel Grinding Device)

A hydrogel that has not been subjected to gel grinding and is to be fed to the gel grinding device in accordance with the present invention has a temperature (herein also referred to as a "gel temperature") preferably of 40° C. to 120° C., more preferably of 60° C. to 120° C., still more preferably of 60° C. to 110° C., and particularly preferably of 65° C. to 110° C., from the viewpoint of particle size control and physical properties. The hydrogel which has a gel temperature lower than 40° C. causes an increase in hardness and elasticity of the resultant hydrogel due to a characteristic of the hydrogel. This may make it difficult to control a particle shape and a particle size distribution during the gel grinding. Meanwhile, the hydrogel which has a gel temperature higher than 120° C. causes an increase in softness of the resultant hydrogel. This may make it difficult to control the particle shape and the particle size distribution. The gel temperature can be appropriately controlled by, for example, a temperature during polymerization, or heating, heat retention, or cooling after the polymerization.

(Hydrogel Treatment Amount)

A treatment amount per unit time of the gel grinding device in accordance with the present invention is a value depending on the inner diameter N and changes in preferable range. The treatment amount per unit time of the gel grinding device in accordance with the present invention can be expressed as a treatment amount-to-inner diameter ratio $T/N^3$ [g/hr/mm$^3$] where an amount in which the gel grinding device in accordance with the present invention treats a hydrogel per hour is T [g/hr] and a value obtained by cubing the inner diameter N is $N^3$ [mm$^3$]. The treatment amount-to-inner diameter ratio $T/N^3$ [g/hr/mm$^3$] has an upper limit preferably of not more than 2.0, more preferably of not more than 1.5, and most preferably of not more than 1.0. In a case where the treatment amount-to-inner diameter ratio $T/N^3$ [g/hr/mm$^3$] has an upper limit of more than 2.0, a hydrogel is insufficiently sheared, so that no intended performance of a water absorbent resin may be obtained. Meanwhile, the treatment amount-to-inner diameter ratio $T/N^3$ [g/hr/mm$^3$] has a lower limit preferably of not less than 0.05, more preferably of not less than 0.10, and most preferably of not less than 0.15. In a case where the treatment amount-to-inner diameter ratio $T/N^3$ [g/hr/mm$^3$] has a lower limit smaller than 0.05, the treatment amount is too small, so that a hydrogel resides in the gel grinding device. This may cause the hydrogel to be excessively sheared and/or cause a deterioration in gel.

(Use of Water)

The gel grinding device 100 in accordance with the present invention can carry out gel grinding with respect to a hydrogel to which water has been added. Note that the "water" to be added in the present invention can be in any form of a solid, a liquid, or a gas. From the viewpoint of handleability, the "water" is preferably in a form of a liquid or a gas, or in a form of a mixture of a liquid and a gas.

How and when to add water is not particularly limited provided that the water is fed to the gel grinding device 100 in which a hydrogel resides. Alternatively, a hydrogel to which water has already been added can be introduced into the gel grinding device 100. Further, it is possible not only to add the "water" alone but also to add, in combination, the "water" and another additive (such as a surfactant, a base for neutralization, a crosslinking agent, or inorganic salt) or a solvent different from water. Note that, in a case where the "water" and another additive or a solvent different from water are added in combination, a resultant solution has a water content preferably of 90 wt % to 100 wt %, more preferably of 99 wt % to 100 wt %, and still more preferably of substantially 100 wt %.

During the addition of the water, the water is fed in an amount preferably of 0 part by weight to 4 parts by weight and more preferably of 0 part by weight by weight to parts by weight based on 100 parts by weight of a hydrogel. In a case where the water is fed in an amount exceeding 4 parts by weight, a problem such as production of an undried hydrogel during drying may occur.

The water which is fed in the form of a liquid has a temperature preferably of 10° C. to 100° C. and more preferably of 40° C. to 100° C. Meanwhile, the water which is fed in the form of a gas has a temperature preferably of 100° C. to 220° C., more preferably of 100° C. to 160° C., and still more preferably of 100° C. to 130° C. Note that a method for preparing the water which is fed in the form of a gas is exemplified by, but not particularly limited to, for example, a method in which water vapor generated by heating a boiler is used and a method in which gaseous water generated from a surface of water by vibrating the water by ultrasonic waves is used. Further, in accordance with the present invention, the water which is fed in the form of a gas is preferably water vapor having a pressure higher than atmospheric pressure, and more preferably water vapor generated by a boiler.

(Use of Additive)

As described earlier, it is preferable to carry out gel grinding with respect to a hydrogel to which water has been added. Further, it is also possible to carry out gel grinding with respect to a hydrogel to/with which not only water but also an additive, a neutralizing agent, or the like is added/mixed. A water absorbent resin to be obtained can be modified. Specifically, an aqueous solution containing a basic substance (e.g., a 10 wt % to 50 wt % aqueous sodium hydroxide) can be added so as to neutralize the hydrogel during the gel grinding. Alternatively, a water absorbent resin fine powder (0.1 wt % to 30 wt % of a water absorbent resin fine powder based on resin solid content) can be added so that fine powder recycling is carried out. Further, 0.001 wt % to 3 wt % of a polymerization initiator, a reducing agent, or a chelating agent (based on resin solid content) can be added to and mixed with the hydrogel during the gel grinding so as to reduce residual monomers, improve coloring, and achieve durability.

(Gel Grinding Energy (GGE)/Gel Grinding Energy (2) (GGE2))

According to a method for producing a water absorbent resin powder in accordance with the present invention, gel grinding energy (GGE) is preferably controlled so as to fall within a predetermined range.

In accordance with the present invention, gel grinding energy (GGE) with which to carry out gel grinding with respect to a hydrogel has an upper limit value preferably of not more than 100 [J/g], more preferably of not more than 60 [J/g], and still more preferably of not more than 50 [J/g]. Meanwhile, the grinding energy (GGE) has a lower limit value preferably of not less than 15 [J/g], more preferably of not less than 18 [J/g], and still more preferably of not less than 20 [J/g]. For example, in accordance with the present invention, the gel grinding energy (GGE) with which to carry out the gel grinding with respect to the hydrogel is in a range preferably of 15 [J/g] to 100 [J/g], more preferably of 18 [J/g] to 60 [J/g], and still more preferably of 20 [J/g] to 50 [J/g]. In a case where the GGE is controlled so as to fall within the above range, it is possible to carry out the gel grinding with respect to the hydrogel while applying a moderate shearing force and a moderate compressive force to the hydrogel. Note that the gel grinding energy (GGE) is defined while including energy during idling of the gel grinding device.

According to the gel grinding device 100 in accordance with the present invention, gel grinding energy 2 (GGE2) is preferably controlled so as to fall within a predetermined range. In accordance with the present invention, gel grinding energy (2) (GGE (2)) with which to carry out gel grinding with respect to a hydrogel has an upper limit value preferably of not more than 40 [J/g], more preferably of not more than 32 [J/g], and still more preferably of not more than 25 [J/g]. Meanwhile, the grinding energy (2) (GGE (2)) has a lower limit value preferably of not less than 7 [J/g], more preferably of not less than 8 [J/g], still more preferably of not less than 10 [J/g], and most preferably of not less than 12 [J/g]. For example, in accordance with the present invention, the gel grinding energy (2) (GGE (2)) with which to carry out the gel grinding with respect to the hydrogel is in a range of 7 [J/g] to 40 [J/g], preferably of 8 [J/g] to 32 [J/g], and more preferably of 10 [J/g] to 25 [J/g]. In a case where the GGE (2) is controlled so as to fall within the above range, it is possible to carry out the gel grinding with respect to the hydrogel while applying a moderate shearing force and a moderate compressive force to the hydrogel. This allows a maximum effect to be exhibited by the shape of the gel grinding device of the present invention.

Note that, in a case where gel grinding is carried out by use of a plurality of devices, e.g., in a case where the gel grinding device 100 in accordance with the present invention is used after kneader polymerization, or in a case where a plurality of gel grinding devices are used, a sum of amounts of energy consumed in the respective devices is set as the gel grinding energy (2) (GGE (2)).

(Effect Yielded by Gel Grinding Device in Accordance with Present Invention)

The gel grinding device in accordance with the present invention which gel grinding device has the arrangement described earlier yields an effect of producing a water absorbent resin powder having a higher liquid permeability, preferably both a higher liquid permeability and a higher water absorbing speed. Further, the gel grinding device yields an effect of producing a water absorbent resin having a smaller thermal conductivity.

[3] A Method for Producing Polyacrylic Acid (Salt)-Based Water Absorbent Resin Powder (3-1) Polymerization Step The polymerization step is a step of polymerizing an aqueous solution whose main component is acrylic acid (salt) to obtain a hydrogel-like crosslinked polymer (herein also referred to as a "hydrogel").

(Monomer)

A water absorbent resin powder in accordance with the present invention is produced from a monomer(s) (a material) whose main component is an acrylic acid (salt). The water absorbent resin powder is usually polymerized in a form of an aqueous solution. An aqueous solution of a monomer(s) whose main component is an acrylic acid (salt) is herein also referred to as "acrylic acid (salt)-based monomer aqueous solution." Monomer concentration in a monomer aqueous solution preferably ranges from 10 wt % to 80 wt %, more preferably from 20 wt % to 80 wt %, still more preferably from 30 wt % to 70 wt %, and particularly preferably from 40 wt % to 60 wt %.

It is preferable, from the viewpoint of water absorption performance and residual monomers, that the hydrogel obtained by the polymerization of the monomer aqueous solution have a polymer having acid groups at least some of which are neutralized. A salt resulting from neutralization is not limited to a specific one, but is, from the view point of water absorption performance, preferably monovalent salt selected from a group consisting of alkali metal salt, ammonium salt, and amine salt, more preferably alkali metal salt, still more preferably alkali metal salt selected from a group consisting of sodium salt, lithium salt, and potassium salt, and particularly preferably sodium salt. Therefore, a basic substance to be used for such neutralization is not limited to a specific one, but is preferably a monovalent basic substance such as (i) a hydroxide of alkali metal including sodium hydroxide, potassium hydroxide, lithium hydroxide, and the like or (ii) a carbonate (hydrogencarbonate) including sodium carbonate (sodium hydrogencarbonate), potassium carbonate (potassium hydrogencarbonate), and the like, and particularly preferably sodium hydroxide.

The neutralization can be carried out in various ways and under various conditions before, during, and after the polymerization. For example, hydrogel obtained by polymerizing an acrylic acid in which acid groups are unneutralized or neutralized at a low neutralization ratio (for example, 0 mol % to 30 mol % of the acid groups are neutralized) can be neutralized, particularly neutralized while being subjected to gel grinding. It is, however, preferable, from the viewpoint of improvement in, for example, productivity or physical properties, that unpolymerized acrylic acid be neutralized. That is, it is preferable that partially neutralized acrylic acid be used as a monomer.

A neutralization ratio of the neutralization is not limited to a specific one, but ranges, with respect to a final product of a water absorbent resin, preferably from 10 mol % to 100 mol %, more preferably from 30 mol % to 95 mol %, still more preferably from 45 mol % to 90 mol %, and particularly preferably from 60 mol % to 80 mol %. A temperature of the neutralization is not limited to a specific one, but ranges preferably from 10° C. to 100° C., and more preferably from 30° C. to 90° C. As to other neutralization process conditions, the condition disclosed in European Patent No. 574260 is preferably applied to the present invention. Note that it is preferable that the hydrogel whose neutralization ratio falls within the above ranges be subjected to gel grinding through the use of a gel grinding device in accordance with the present invention in a gel grinding step.

In order to improve physical properties of the water absorbent resin powder obtainable by the present invention, any component such as (i) water soluble resin or water absorbent resin including starch, cellulose, polyvinyl alcohol (PVA), polyacrylic acid (salt), polyethyleneimine, and the like, (ii) a foaming agent including a carbonate, an azo compound, an air bubble generating agent, and the like, (iii) a surfactant, or (iv) an additive, can be added to the monomer aqueous solution, the hydrogel, a dried polymer, the water absorbent resin, or the like in any step of a production process of the present invention. In a case where the water soluble resin or the water absorbent resin is to be added, an amount of the water soluble resin or the water absorbent resin to be added preferably ranges from 0 wt % to 50 wt % based on the monomer, more preferably from 0 wt % to 20 wt %, still more preferably from 0 wt % to 10 wt %, and particularly preferably from 0 wt % to 3 wt %. In a case where the foaming agent, the surfactant, or the additive is to be added, an amount of the foaming agent, the surfactant, or the additive to be added preferably ranges from 0 wt % to 5 wt %, and more preferably from 0 wt % to 1 wt %. Note that a graft polymer or a water absorbent resin composition can be obtained through addition of the water soluble resin or the water absorbent resin. A polymer produced from starch and an acrylic acid, a polymer produced from PVA and an acrylic acid, and the like polymer are also regarded as a polyacrylic acid (salt)-based water absorbent resin in the present invention.

Further, a chelating agent, an $\alpha$-hydroxycarboxylic acid compound, or an inorganic reducing agent can be used in order to improve (i) color tone stability of the water absorbent resin powder obtainable by the present invention (color tone stability of the water absorbent resin powder which has undergone long-term storage under high temperature and high humidity) or (ii) urine resistance (prevention of gel deterioration) of the water absorbent resin powder. Among these, the chelating agent is particularly preferably used. A used amount of the chelating agent, the $\alpha$-hydroxycarboxylic acid compound, or the inorganic reducing agent preferably ranges from 10 ppm to 5000 ppm based on the water absorbent resin, more preferably from 10 ppm to 1000 ppm, still more preferably from 50 ppm through 1000 ppm, and particularly preferably from 100 ppm to 1000 ppm. Note that one of the compound disclosed in U.S. Pat. No. 6,599,989 and the compound disclosed in International Publication No. 2008/090961 is employed as the chelating agent in the present invention. Among these compounds, an aminocarboxylic acid-based metal chelating agent or a polyvalent phosphoric acid-based compound is preferably used as the chelating agent.

In a case where an acrylic acid (salt) is used as a main component in the present invention, a hydrophilic or hydrophobic unsaturated monomer(s) (herein referred to as "other monomer(s)") other than the acrylic acid (salt) can be used in combination with the acrylic acid (salt). Such other monomer(s) is not limited to a specific one. Examples of the other monomer(s) encompass methacrylic acid, (anhydrous) maleic acid, 2-(meth) acrylamide-2-methylpropanesulfonic acid, (meth)acryloxyalkanesulfonic acid, N-vinyl-2-pyrolidone, N-vinylacetamide, (meth) acrylamide, N-isopropyl (meth) acrylamide, N,N-dimethyl (meth) acrylamide, 2-hydroxyethyl (meth) acrylate, methoxypolyethyleneglycol (meth) acrylate, polyethyleneglycol (meth) acrylate, stearylacrylate, salts thereof, and the like. In a case where the other monomer(s) is to be used, a used amount of the other monomer(s) is determined as appropriate so as not to impair water absorption performance of a water absorbent resin powder to be obtained and is not limited to a specific one, but ranges preferably from 0 mol % to 50 mol % based on the total amount of monomers, more preferably from 0 mol % to 30 mol %, and still more preferably from 0 mol % to 10 mol %.

(Internal Crosslinking Agent)

In the present invention, it is preferable, from the viewpoint of water absorption performance of a water absorbent resin powder to be obtained, that a crosslinking agent (herein referred to as an "internal crosslinking agent") be used. The internal crosslinking agent is not limited to a specific one. Examples of the internal crosslinking agent encompass a polymerizable crosslinking agent which is polymerizable with an acrylic acid, a reactive crosslinking agent which is reactive with a carboxyl group, a crosslinking agent which is polymerizable with an acrylic acid and reactive with a carboxyl group, and the like.

Examples of the polymerizable crosslinking agent encompass compounds each having at least two polymerizable double bonds in a molecule, such as N,N'-methylene bisacrylamide, (poly)ethylene glycol di(meth) acrylate, (polyoxyethylene)trimethylolpropane tri(meth)acrylate, and poly(meth)allyloxy alkane. Examples of the reactive crosslinking agent encompass: covalent bonding crosslinking agents such as polyglycidyl ether (e.g., ethyleneglycoldiglycidyl ether) and polyvalent alcohol (e.g., propanediol, glycerine, and sorbitol); and an ionic bonding crosslinking agent such as a polyvalent metal compound (e.g., aluminum salt). Among these, from the viewpoint of water absorption performance, the internal crosslinking agent is more preferably the polymerizable crosslinking agent which is polymerizable with an acrylic acid, and particularly preferably an acrylate-based, allyl-based or acrylamide-based polymerizable crosslinking agent. These internal crosslinking agents can be used singly or in combination. Note that in a case where the polymerizable crosslinking agent and the reactive crosslinking agent are used in combination, a mixture ratio of the polymerizable crosslinking agent and the covalent bonding crosslinking agent is preferably 10:1 to 1:10.

From the viewpoint of the physical properties, a used amount of the internal crosslinking agent preferably ranges from 0.001 mol % to 5 mol % based on the total amount of monomers excluding a crosslinking agent, more preferably from 0.002 mol % to 2 mol %, still more preferably from 0.04 mol % to 1 mol %, particularly preferably from 0.06 mol % to 0.5 mol %, and most preferably from 0.07 mol % to 0.2 mol %. Moreover, in a particularly preferable embodiment of the present invention, the polymerizable crosslinking agent is used in an amount preferably ranging from 0.01 mol % to 1 mol %, more preferably from 0.04 mol % to 0.5 mol %, and still more preferably from 0.06 mol % to 0.1 mol %.

(Polymerization Initiator)

A polymerization initiator used in the present invention is selected appropriately depending on how the polymerization is carried out, and is not limited to a specific one. Examples of the polymerization initiator encompass photolytic-type polymerization initiators, pyrolysis-type polymerization initiators, redox-type polymerization initiators, and the like.

Examples of the photolytic-type polymerization initiators encompass benzoin derivatives, benzyl derivatives, acetophenone derivatives, benzophenone derivatives, azo compounds, and the like. Examples of the pyrolysis-type polymerization initiators encompass: persulfates such as sodium persulfate, potassium persulfate, and ammonium persulfate; peroxides such as hydrogen peroxide, t-butyl peroxide, and methyl-ethyl-ketone peroxide; azo compounds such as 2,2'-azobis (2-amidinopropane) dihydrochloride, and 2,2'-azobis [2-(2-imidazoline 2-yl) propane] dihydrochloride; and the like. Examples of the redox-type polymerization initiators encompass systems each of which is a combination of (i) a reducing compound such as L-ascorbic acid or sodium hydrogen sulfite and (ii) any of the persulfates and peroxides. Further, it is also a preferable embodiment to use any of the photolytic-type polymerization initiators and any of the pyrolysis-type polymerization initiators in combination.

A used amount of the polymerization initiator preferably ranges from 0.0001 mol % to 1 mol %, and more preferably from 0.0005 mol % to 0.5 mol %, based on the total amount of the monomers. The polymerization initiator used in an amount exceeding 1 mol % may cause a deterioration in color tone of a water absorbent resin. Moreover, the polymerization initiator used in an amount of less than 0.0001 mol % is not preferable because it may increase residual monomers.

(Polymerization Method)

In the method for producing a water absorbent resin powder in accordance with the present invention, a polymerization method to obtain a particulate hydrogel can be spraying droplet polymerization or reverse phase suspension polymerization. However, aqueous solution polymerization is employed from the viewpoint of liquid permeability (SFC) and water absorbing speed (FSR) of a water absorbent resin powder to be obtained, polymerization controllability, and others. The aqueous solution polymerization can be tank-type (silo-type) unstirring polymerization. However, the aqueous solution polymerization is preferably kneader polymerization or belt polymerization, more preferably continuous aqueous solution polymerization, still more preferably high-concentration continuous aqueous solution polymerization, and particularly preferably high-concentration high-temperature starting continuous aqueous solution polymerization. Note that stirring polymerization means polymerizing a hydrogel while stirring a hydrogel, particularly polymerizing the hydrogel while stirring and grain-refining the hydrogel (wherein the hydrogel is particularly a hydrogel having a polymerization ratio of not less than 10 mol %, further particularly a hydrogel having a polymerization ratio of not less than 50 mol %). A monomer aqueous solution (having a polymerization ratio of 0 mol % to less than 10 mol %) can be stirred as appropriate before and/or after the unstirring polymerization is carried out.

Examples of the continuous aqueous solution polymerization encompass continuous kneader polymerization (disclosed in U.S. Pat. Nos. 6,987,171 and 6,710,141, and others), and continuous belt polymerization (disclosed in U.S. Pat. Nos. 4,893,999 and 6,241,928, U.S. Patent Application Publication No. 2005/215734, and others). These aqueous solution polymerizations can produce a water absorbent resin powder with high productivity.

In the high-concentration continuous aqueous solution polymerization, monomer concentration (solid content) is preferably not less than 35 wt %, more preferably not less than 40 wt %, and still more preferably not less than 45 wt % (but not more than saturated concentration). In high-temperature starting continuous aqueous solution polymerization, a polymerization starting temperature is preferably not lower than 30° C., more preferably not lower than 35° C., still more preferably not lower than 40° C., and particularly preferably not lower than 50° C. (but not lower than boiling temperature). The high-concentration high-temperature starting continuous aqueous solution polymerization is a combination of the high-concentration continuous aqueous solution polymerization and the high-temperature starting continuous aqueous solution polymerization.

The high-concentration high-temperature starting continuous aqueous solution polymerization is disclosed in U.S. Pat. Nos. 6,906,159 and 7,091,253, and others. The high-concentration high-temperature starting continuous aqueous solution polymerization is preferable because it can produce a water absorbent resin powder with a high degree of whiteness and can be easily applied to industrial-scale production.

Therefore, the polymerization method in the production method in accordance with the present invention is suitably applied to a large-scale production apparatus having a great production volume per production line. Note that the production volume is preferably not less than 0.5 [t/hr], more preferably not less than 1 [t/hr], still more preferably 5 [t/hr], and particularly preferably 10 [t/hr].

The polymerization can be carried out under air atmosphere. It is, however, preferable from the viewpoint of coloring prevention that the polymerization be carried out under inert gas atmosphere such as water vapor, nitrogen, or argon (with, for example, an oxygen concentration of not more than 1% by volume). It is further preferable that the polymerization be carried out after oxygen dissolved in a monomer(s) or in a solution containing a monomer(s) is substituted for (deaerated with) inert gas (by, for example, less than 1 [mg/L] of oxygen). Such deaeration allows for a monomer(s) having an excellent stability, without causing gelling before polymerization. This makes it possible to provide a water absorbent resin powder with higher physical properties and a high degree of whiteness.

An amount of inert gas to be used is preferably 0.005 wt % to 0.2 wt % based on the total amount of a monomer(s), more preferably 0.01 wt % to 0.1 wt %, and most preferably 0.015 wt % to 0.5 wt %. Further, nitrogen is preferably used as the inert gas.

(Surfactant, Dispersant)

In the polymerization step of the present invention, a surfactant and/or a dispersant can be used if necessary. The use of the surfactant and/or the dispersing agent allows gas bubbles to be stably suspended in a water absorbent resin during the polymerization. Further, by adjusting the type(s) or amount(s) of the surfactant and/or the dispersant as appropriate, it is possible to obtain a water absorbent resin powder having intended physical properties. It is preferable that the surfactant be a non-polymeric surfactant, while the dispersant is a polymeric dispersant. Further, it is preferable that the surfactant and/or the dispersant be added before the monomer aqueous solution before or during polymerization reaches a temperature of 50° C. or higher.

A used amount of the surfactant and/or the dispersant can be determined as appropriate according to the type(s) of the surfactant and/or the dispersant. The use of the surfactant and/or the dispersant changes a surface tension of a water absorbent resin powder to be obtained. Thus, the used amount of the surfactant and/or the dispersant is determined so that the surface tension of the water absorbent resin powder to be obtained is preferably not less than 60 [mN/m], more preferably not less than 65 [mN/m], still more preferably not less than 67 [mN/m], further still more preferably not less than 69 [mN/m], and most preferably not less than 70 [mN/m]. In a case where the surface tension of the water absorbent resin powder to be obtained is less than 60 [mN/m], the amount of return of a liquid from a disposable diaper in use may increase. In order to prevent a decrease in surface tension of a water absorbent resin powder to be obtained, it is preferable to use a surfactant having polymerizability or reactivity with a water absorbent resin powder or its monomer (e.g. a surfactant having a polymerizable unsaturated group (in particular, an α,β-unsaturated double bond) and a reactive group (a hydroxyl group or an amino group)) or a hydrophilic surfactant having a high water solubility (for example, HLB of 1 to 18, particularly preferably 8 to 15). As specific surfactants, surfactants shown as examples in International Publication No. 2011/078298 are suitably used. Among them, a nonionic surfactant is preferable, a nonionic surfactant having a polyoxyethylene chain in a molecule is further preferable, and polyoxyethylene sorbitan fatty acid ester is most preferable.

A used amount of any of these surfactants depends on the type of the surfactant to be used or intended physical properties (in particular, water absorbing speed and surface tension). However, the used amount is typically more than 0 wt % and not more than 2 wt %, preferably more than 0 wt % and not more than 0.03 wt %, more preferably more than 0 wt % and not more than 0.015 wt %, still more preferably more than 0 wt % and not more than 0.01 wt %, and most preferably more than 0 wt % and not more than 0.008 wt %, based on the amount of a monomer(s) to be used. The used amount of the surfactant is applicable to a water absorbent resin powder after polymerization, and is further applicable, if necessary, to a water absorbent resin powder as an end product obtained after coating of a surfactant described later in "(3-5) Surface treatment step."

(Physical Properties of Hydrogel which has not been Subjected to Gel Grinding)

(a) Resin Solid Content

A resin solid content of a hydrogel which has not been subjected to gel grinding ranges from 10 wt % to 80 wt % from the viewpoint of physical properties, preferably from 30 wt % to 80 wt %, more preferably from 40 wt % to 80 wt %, still more preferably from 45 wt % to 60 wt %, and particularly preferably from 50 wt % to 60 wt %. A resin solid content of less than 10 wt % results in greater softness of the hydrogel to be obtained, thus making it difficult to control the particle shape and the particle size distribution. A resin solid content of more than 80 wt % results in greater hardness of the hydrogel to be obtained, thus making it difficult to control the particle shape and the particle size distribution. The resin solid content of the hydrogel can be appropriately controlled by polymerization concentration, moisture vaporization during polymerization, addition of a water absorbent resin fine powder (fine powder recycle step) in a polymerization step, or if necessary, moisturization or partial drying after polymerization.

Note that the resin solid content of the hydrogel which has not been subjected to gel grinding is calculated from the drying loss described in (f) of (1-3) above.

(b) Gel CRC

CRC of a hydrogel which has not been subjected to gel grinding (herein referred to as "gel CRC") preferably ranges from 10 [g/g] to 35 [g/g], more preferably from 10 [g/g] to 32 [g/g], still more preferably from 10 [g/g] to 30 [g/g], and particularly preferably from 15 [g/g] to 30 [g/g]. A gel CRC of less than 10 [g/g] or more than 35 [g/g] may make it difficult to control the particle shape and the particle size distribution during the gel grinding. The gel CRC of the hydrogel which has not been subjected to gel grinding can be appropriately controlled by an added amount of cross-linking agent during polymerization, polymerization concentration, or the like. Note that it is a well-known fact that a water absorbent resin preferably has a high gel CRC. It was, however, found in the present invention that a gel CRC of more than 35 [g/g] makes it difficult to control the particle shape and the particle size distribution.

Note that the gel CRC of the hydrogel which has not been subjected to gel grinding is calculated by a measurement method that will be described in (a) of [Examples] below.

(c) Gel Ext

A water soluble component of a hydrogel which has not been subjected to gel grinding (gel Ext) preferably ranges from 0.1 wt % to 10 wt %, more preferably from 0.5 wt % to 8 wt %, and still more preferably from 1 wt % to 5 wt %. A gel Ext of more than 10 wt % results in excessive increase in weight average molecular weight of a water soluble component due to a shearing force during the gel grinding. This may cause a failure to attain an intended liquid permeability. The gel Ext of the hydrogel which has not been subjected to gel grinding is preferably small. However, a lower limit of the gel Ext is in the above range from the viewpoint of, for example, balance with the above (c) Gel CRC, a manufacturing cost necessary for reduction in the gel Ext, or decrease in productivity.

Note that the gel Ext of the hydrogel which has not been subjected to gel grinding is calculated by a measurement method that will be described in (b) of [Examples] below.

(d) Weight Average Molecular Weight of Water Soluble Component

Weight average molecular weight of a water soluble component of a hydrogel which has not been subjected to gel grinding preferably ranges from 50,000 [Da] to 450,000 [Da], more preferably from 100,000 [Da] to 430,000 [Da], and still more preferably from 150,000 [Da] to 400,000 [Da].

Weight average molecular weight of a water soluble component of less than 50,000 [Da] results in decrease in particle diameter of particulate hydrogel obtained after the gel grinding. This may cause a failure to obtain a water absorbent resin powder having intended physical properties. Moreover, weight average molecular weight of a water soluble component of more than 450,000 [Da] results in fewer crosslinking points, thus causing a greater influence of a shearing force than necessary. This may cause a decrease in performance such as an increase in amount of water soluble component after the gel grinding. The weight average molecular weight of the water soluble component can be appropriately controlled by, for example, an added amount of crosslinking agent during polymerization, polymerization concentration, or if necessary, a chain transfer agent.

Note that the weight average molecular weight of the water soluble component of the hydrogel which has not been subjected to gel grinding is calculated by a measurement method that will be described in (c) of [Examples] below.

(3-2) Gel Grinding Step

The gel grinding step is a step carried out by use of a gel grinding device in accordance with the present invention and is also a step of grain-refining the aforementioned hydrogel-like crosslinked polymer during or after polymerization to obtain a particulate hydrogel-like crosslinked polymer. Note that an operation carried out in this step is called "gel grinding" as distinguished from "pulverization" in "(3-4) Pulverization step and classification step".

The gel grinding device used in the gel grinding step of the present invention is a gel grinding device in accordance with the present invention. Configuration, temperatures, and operation conditions of the gel grinding device are as described in [2] above.

(Hydrogel Subjected to Gel Grinding Step)

The gel grinding in the present invention is carried out with respect to a hydrogel which has been polymerized. The gel grinding can also be carried out with respect to a gel dispersed in an aqueous solution and being in a "sufficiently gelling" state.

The "sufficiently gelling state" is a state in which the hydrogel can be grain-refined by application of a shearing force at a time when or after a polymerization temperature reaches a maximum temperature (herein also referred to as a "polymerization peak temperature"). Alternatively, the "sufficiently gelling state" is a state in which the hydrogel can be grain-refined by application of a shearing force at a time when or after a polymerization ratio of monomers in the monomer aqueous solution (the polymerization ratio is also known as "conversion ratio" and is calculated from (i) polymer quantity calculated by pH titration of the hydrogel and (ii) residual monomer quantity) is preferably not less than 90 mol %, more preferably not less than 93 mol %, still more preferably not less than 95 mol %, and particularly preferably not less than 97 mol %. That is, the hydrogel having the polymerization ratio of the monomers in the above range is subjected to gel grinding in the gel grinding step of the present invention. Note that in a case of polymerization reaction that does not have the polymerization peak temperature (e.g. a case where polymerization proceeds at a constant temperature at all times, a case where polymerization temperature keeps rising, or the like case), whether or not the monomer aqueous solution is being in the "sufficiently gelling state" is determined on the basis of the polymerization ratio of the monomers.

In a case where belt polymerization is carried out in the polymerization step, a hydrogel during or after the belt polymerization, preferably after the belt polymerization, can be cut or cracked to have a size of several tens of centimeters before the gel grinding. Such an operation allows the hydrogel to easily fill the gel grinding device. This makes it possible to smoothly carry out the gel grinding step. Note that cutting or cracking means is preferably the one being capable of cutting or cracking the hydrogel, and the cutting or cracking means is, for example, a guillotine cutter or the like. Size and shape of the cut or cracked hydrogel are not limited to specific ones and can be any size and shape provided that the hydrogel can fill the gel grinding device. Further, in a case where weight of a piece of the cracked hydrogel is one tenth or less of "weight of a hydrogel-like crosslinked polymer to be introduced into the gel grinding device per second", energy during the cracking is included in the GGE during the gel grinding.

(Physical Properties of Particulate Hydrogel after Gel Grinding)

(a) Particle Size

The hydrogel-like crosslinked polymer (hydrogel) obtained in the polymerization step is ground into particles by the aforementioned gel grinding device of the present invention. Note that a gel particle diameter can be controlled by classification, blending, or the like. It is, however, preferable that the gel particle diameter be controlled by the gel grinding device in accordance with the present invention.

The weight average particle diameter (D50) (specified by sieve classification) of the particulate hydrogel after gel grinding ranges from 350 μm to 2000 μm, more preferably from 400 μm to 1500 μm, and still more preferably from 500 μm to 1000 μm. A logarithmic standard deviation ($\sigma\zeta$) of the particle size distribution preferably ranges from 0.2 to 1.5, more preferably from 0.2 to 1.2, and still more preferably from 0.2 to 1.0.

In a case where the weight average particle diameter is more than 2000 μm, an uneven or insufficient shearing force and an uneven or insufficient compressive force may be applied to the hydrogel. Further, in that case, an inner part of the hydrogel is different from a surface of the hydrogel in degree of drying. This may cause particles with inhomogeneous physical properties to be generated through pulverization carried out after the hydrogel is dried, thus deteriorating the physical properties as a whole. Moreover, in a case where the weight average particle diameter is less than 350 μm, the hydrogel has an increased surface area, and is therefore susceptible to extreme drying. This makes it insufficient to reduce residual monomers in the drying step and thus increases the residual monomers. Further, generation of a large amount of fine powder during the pulverization after the drying not only makes it difficult to control the particle size but also deteriorates the physical properties of a water absorbent resin such as liquid permeability (SFC). Note that an ordinary gel grinding operation alone makes it difficult to obtain the hydrogel having weight average particle diameter of less than 350 μm, and it is necessary to separately carry out a special operation such as (i) classification of gel after the gel grinding (e.g. Japanese Patent Application Publication, Tokukaihei No. 6-107800) or (ii) particle size control during the polymerization before the gel grinding (e.g. European Patent No. 0349240 disclosing a method for producing gel particles having a sharp particle size distribution during reverse-phase suspension polymerization). The special operation thus carried out in addition to the gel grinding newly causes problems that (i) a large amount of surfactant or organic solvent is required for the polymerization or the classification and (ii) productivity is decreased (rise in cost) or the physical properties of the water absorbent resin are deteriorated (increase of residual monomers or increase of fine powder), and like problems. It is therefore not only difficult but also unpreferable that the particulate hydrogel has the weight average particle diameter of less than 350 μm.

It is preferable from the viewpoint of achieving uniform drying that the logarithmic standard deviation ($\sigma\zeta$) be as small as possible. However, for a logarithmic standard deviation ($\sigma\zeta$) of less than 0.2, it is necessary to carry out the special operation such as the classification of the gel after the gel grinding or the particle size control during the polymerization before the gel grinding, as with the weight average particle diameter. It is therefore neither preferable nor attainable in consideration of productivity and cost that the particulate hydrogel has the logarithmic standard deviation ($\sigma\zeta$) of less than 0.2. The particle size can be controlled by gel grinding of the present invention. The hydrogel is subjected to gel grinding by particularly the gel grinding device in accordance with the present invention under such a condition that the above particle size can be obtained.

(b) Gel CRC after Gel Grinding

In the present invention, gel CRC of the particulate hydrogel after gel grinding preferably ranges from 10 [g/g] to 35 [g/g], more preferably from 10 [g/g] to 32 [g/g], and still more preferably from 15 [g/g] to 30 [g/g]. Further, the gel CRC after the gel grinding is increased by preferably −1 [g/g] to +3 [g/g] than gel CRC before the gel grinding, more preferably +0.1 [g/g] to +2 [g/g], and still more preferably +0.3 [g/g] to +1.5 [g/g]. Note that the gel CRC after the gel grinding can be decreased during the gel grinding by use of a crosslinking agent, or the like. It is, however, preferable that the gel CRC after the gel grinding be increased in the above range.

(c) Gel Ext after Gel Grinding

In the present invention, gel Ext of the particulate hydrogel after gel grinding preferably ranges from 0.1 wt % to 20 wt %, more preferably from 0.1 wt % to 10 wt %, still more preferably from 0.1 wt % to 8 wt %, and particularly preferably from 0.1 wt % to 5 wt %. Further, how much the gel Ext of the particulate hydrogel is increased by gel grinding (i.e. an amount of increase in gel Ext with respect to gel Ext before the gel grinding) is preferably not more than 5 wt %, more preferably not more than 4 wt %, still more preferably not more than 3 wt %, particularly preferably not more than 2 wt %, and most preferably not more than 1 wt %. The amount of increase in gel Ext of the particulate hydrogel by gel grinding can also have a minus lower limit (for example, −3.0 wt %, further −1.0 wt %). However, the amount of increase in gel Ext of the particulate hydrogel by gel grinding is generally not less than 0 wt %, preferably not less than 0.1 wt %, more preferably not less than 0.2 wt %, and still more preferably not less than 0.3 wt %. Specifically, the hydrogel only needs to be subjected to gel grinding so that the gel Ext is increased to fall within any of the above ranges of the upper limits and the lower limits (e.g., preferably from 0 wt % to 5.0 wt % and more preferably from 0.1 wt % to 3.0 wt %). Note that the gel Ext can be decreased during the gel grinding by use of a crosslinking agent, or the like. It is, however, preferable that the gel Ext be increased in the above range. Note here that an effective digit of the amount of increase in gel Ext is the first decimal place, and for example, 5 wt % and 5.0 wt % are regarded as being the same as each other.

(d) Weight Average Molecular Weight of Water Soluble Component after Gel Grinding In the present invention, an amount of increase in weight average molecular weight of a water soluble component of the hydrogel by gel grinding has (i) a lower limit of preferably not less than 10,000 [Da], more preferably not less than 20,000 [Da], and still more preferably not less than 30,000 [Da], and (ii) an upper limit of preferably not more than 500,000 [Da], more preferably not more than 400,000 [Da], still more preferably not more than 250,000 [Da], and particularly preferably not more than 100,000 [Da]. For example, in the present invention, the amount of increase in weight average molecular weight of a water soluble component of the particulate hydrogel after gel grinding with respect to the hydrogel which has not been subjected to gel grinding ranges from 10,000 [Da] to 500,000 [Da], preferably from 20,000 [Da] to 400,000 [Da], more preferably from 30,000 [Da] to 250,000 [Da], and still more preferably from 30,000 [Da] to 100,000 [Da].

In the conventional gel grinding as a known technique, an increase in weight average molecular weight of a water soluble component is often less than 10,000 [Da]. On the contrary, in the present invention, it is preferable that the weight average molecular weight of the water soluble component be increased by cutting a main chain part of a polymer of the hydrogel by application of a greater gel grinding energy (GGE), that is, a greater shearing force and a greater compressive force. Note, however, that in a case where the amount of weight average molecular weight of the water soluble component to be increased by gel grinding is greater than 500,000 [Da], a crosslinked polymer chain of the hydrogel is cut by excessive mechanical external force so that the water soluble component is excessively increased. This may deteriorate the physical properties of the water absorbent resin.

(e) Resin Solid Content after Gel Grinding

In the present invention, a resin solid content of the particulate hydrogel after gel grinding, from the viewpoint of physical properties, preferably ranges from 10 wt % to 80 wt %, more preferably from 30 wt % to 80 wt %, still more preferably from 50 wt % to 80 wt %, 45 wt % to 85 wt %, or 45 wt % to 70 wt %, and particularly preferably from 50 wt % to 60 wt % or 45 wt % to 60 wt %. It is preferable that the resin solid content of the particulate hydrogel after gel grinding fall within the above range. This is because, in that case, an increase in the CRC due to drying is easily controllable, and an influence caused by drying (for example, increase of the water soluble component) is decreased. Note that the resin solid content after the gel grinding can be appropriately controlled by, for example, a resin solid content before the gel grinding, if necessary, water to be added, or water vaporization by heating during the gel grinding.

(Pieces to be Measured)

In order to estimate the physical properties of the hydrogel which has not been subjected to gel grinding or the physical properties of the particulate hydrogel after gel grinding, it is necessary to sample and measure, at a required frequency, a required amount of the hydrogel or the particulate hydrogel which is in a production apparatus. A value obtained by measuring the sampled hydrogel should be a numeric value that is sufficiently averaged. In order to obtain such a numeric value, for example, the following sampling and measurement is carried out. In a case where the water absorbent resin powder is produced by 1 [t/hr] to 20 [t/hr], or 1 [t/hr] to 10 [t/hr] by continuous gel grinding by use of, for example, a continuous kneader or a meat chopper, it is only necessary to sample and measure two or more pieces per 100 kg of the hydrogel, at least ten or more pieces in total, and to estimate the physical properties of the particulate hydrogel on the basis of the sampling and the measurement.

(3-3) Drying Step

The drying step is a step of drying the particulate hydrogel obtained in the gel grinding step to obtain a dried polymer. The following will describe a drying method suitably applicable to the present invention.

Examples of the drying method in the drying step of the present invention encompass thermal drying, hot air drying, drying under reduced pressure, infrared drying, microwave drying, drying by use of a drum drier, drying by azeotropic dehydration with a hydrophobic organic solvent, and high humidity drying by use of high temperature water vapor. Among the drying methods, the hot air drying is preferable. Particularly, hot air drying with a dew point of 40° C. to 100° C., more preferably a dew point of 50° C. to 90° C., is suitably adopted.

As a method of drying the particulate hydrogel in the present invention, a through-flow drier is preferably used, and a through-flow belt hot air drier is further preferably used. In a case where the through-flow belt hot air drier is used, the through-flow belt hot air drier should send hot air to a hydrogel layer provided on a through-flow belt and allowed to stand still from a direction vertical to the hydrogel layer (for example, from both above and below the hydrogel layer, from below the hydrogel layer, or from above the hydrogel layer). In a case where the through-flow belt hot air drier is not used or in a case where hot air is not sent from the direction vertical to the hydrogel layer, it is impossible to uniformly dry the hydrogel layer. This may deteriorate physical properties (e.g. liquid permeability) of a water absorbent resin powder to be obtained. Note that the "direction vertical to the hydrogel layer" is a state in which hot air flows through a gel layer (a layer of particulate hydrogel having a thickness in a range of 10 mm to 300 mm and laminated on a punching metal or a woven metallic wire) in a vertical direction to the gel layer (from above the gel layer to below the gel layer, or from below the gel layer to above the gel layer). The direction vertical to the gel layer is not limited to a completely vertical direction as long as hot air flows through the gel layer in an up-and-down direction. Therefore, hot air can be sent from an oblique direction, for example, hot air is sent from a direction within 30 degrees from the vertical direction, preferably within 20 degrees, more preferably within 10 degrees, still more preferably within 5 degrees, and particularly preferably from the completely vertical direction.

The following will describe drying conditions and others of the drying step of the present invention. The hydrogel ground by the gel grinding device of the present invention is dried preferably under the drying conditions. This makes it possible to improve liquid permeability, preferably both the liquid permeability and water absorbing speed of a water absorbent resin powder obtained by subjecting, to surface treatment, a dried polymer attained by drying the hydrogel under the drying conditions.

(Drying Temperature)

Drying temperature in the drying step (preferably in the through-flow belt-type dryer) of the present invention ranges from 100° C. to 300° C., preferably from 150° C. to 250° C., more preferably from 160° C. to 220° C., and still more preferably from 170° C. to 200° C. A drying temperature ranging from 100° C. to 300° C. makes it possible to reduce a drying time and coloring of a dried polymer to be obtained. Further, such a drying temperature tends to improve liquid permeability, preferably both the liquid permeability and water absorbing speed of a water absorbent resin powder to be obtained. Meanwhile, a drying temperature of higher than 300° C. affects a polymer chain, thus deteriorating the physical properties of a water absorbent resin powder to be obtained. Moreover, a drying temperature of lower than 100° C. (i) generates undried particulate hydrogel and (ii) causes clogging during a subsequent pulverization step, without changing the water absorbing speed.

(Drying Time)

A drying time in the drying step (preferably by use of the through-flow belt-type dryer) of the present invention depends on a surface area of the particulate hydrogel, types of a drier, and the like, and only needs to be appropriately determined so that an objective moisture content is attained. However, the drying time preferably ranges from 1 minute to 10 hours, more preferably from 5 minutes to 2 hours, still more preferably from 10 minutes to 1 hour, and particularly preferably from 15 minutes to 45 minutes.

A period of time that elapses before the particulate hydrogel discharged from the gel grinding step of (3-2) above proceeds to the drying step, that is, a period of time of moving of the particulate hydrogel from an outlet of the gel grinding device to an inlet of the drier is preferably shorter from the viewpoint of coloring of a water absorbent resin powder. Specifically, the period of time is preferably within 2 hours, more preferably within 1 hour, still more preferably within 30 minutes, particularly preferably within 10 minutes, and most preferably within 2 minutes.

(Air Velocity)

In the drying step of the present invention, in order to further attain the object of the present invention, the through-flow drier, especially the belt-type drier, sends hot air in the vertical direction (an up-and-down direction) at an air velocity of 0.8 [m/s] to 2.5 [m/s], preferably 1.0 [m/s] to 2.0 [m/s]. The air velocity in the above range makes it possible not only to control moisture content of the dried polymer to be obtained to be in an intended range but also to improve the water absorbing speed. An air velocity of less than 0.8 [m/s] results in elongation of the drying time. This may deteriorate liquid permeability and water absorbing speed of a water absorbent resin powder to be obtained. An air velocity of more than 2.5 [m/s] causes the particulate hydrogel to be blown up during drying. This may make it difficult to stably dry the particulate hydrogel.

Note that the air velocity only needs to be controlled so as not to impair the effect of the present invention, and therefore the air velocity only needs to be controlled as above, for example, during 70% or more of the drying time, preferably 90% or more, and still more preferably 95% or more. Note also that in a case of the through-flow belt-type drier, the air velocity is represented by an average flow rate of hot air passing in a direction vertical to a surface of the through-flow belt that horizontally moves. Therefore, the average flow rate of hot air is calculated by dividing, by an area of the through-flow belt, quantity of hot air sent to the through-flow belt drier.

(Dew Point of Hot Air)

The hot air used by the through-flow belt-type drier in the drying step of the present invention contains at least water vapor, and has a dew point of preferably 30° C. to 100° C., and more preferably 30° C. to 80° C. Controlling the dew point of hot air in the above range or further preferably the gel particle diameter in the above range makes it possible to reduce residual monomers, and further prevent reduction in bulk specific gravity of the dried polymer. Note that the dew point is a value as of a point in time when the particulate hydrogel has a moisture content of at least 10 wt % or more, preferably 20 wt % or more.

Further, in the drying step of the present invention, it is preferable that a dew point in the vicinity of the inlet of the drier (or in the early period of drying, for example, at or before a timing of 50% of the drying time) be higher than a dew point in the vicinity of an outlet of the drier (or in the last period of the drying, for example, at or after a timing of 50% of the drying time) from the viewpoint of, for example, residual monomers, water absorption performance, and coloring. Specifically, it is preferable to expose the particulate hydrogel to hot air having a dew point higher by preferably 10° C. to 50° C., more preferably 15° C. to 40° C., in the vicinity of the inlet of the drier than in the vicinity of the outlet of the drier. Controlling the dew point in the above range makes it possible to prevent the reduction in the bulk specific gravity of the dried polymer.

(Resin Solid Content)

The particulate hydrogel obtained in the gel grinding step is dried in the drying step to be the dried polymer. Resin solid content calculated from drying loss of the dried polymer (heating 1 g of powder or particles at 180° C. for three hours) is preferably more than 80 wt %, more preferably in a range of 85 wt % to 99 wt %, still more preferably in a range of 90 wt % to 98 wt %, and particularly preferably in a range of 92 wt % to 97 wt %.

(Surface Temperature of Particulate Hydrogel)

The particulate hydrogel obtained in the gel grinding step has a surface temperature preferably in a range of 40° C. to 110° C., more preferably in a range of 60° C. to 110° C., still more preferably in a range of 60° C. to 100° C., and particularly preferably in a range of 70° C. to 100° C., immediately before being introduced into the drier. A surface temperature of lower than 40° C. generates a balloon-like dried substance during drying and generates plenty of fine powder during pulverization. This may deteriorate the physical properties of the water absorbent resin. Moreover, a surface temperature of higher than 110° C. of the particulate hydrogel before drying causes deterioration (such as, for example, an increase of a water soluble component) or coloring of the water absorbent resin after drying.

(3-4) Pulverization Step and Classification Step

These steps are steps of pulverizing and classifying the dried polymer obtained in the drying step to obtain water absorbent resin particles. Note that the pulverization step is different from (3-2) Gel grinding step in resin solid content during pulverization, especially in that a target to be pulverized in the pulverization step has been dried in the drying step (preferably the resin solid content also has been dried). The water absorbent resin particles obtained after the pulverization step may be referred to as a "pulverized substance."

The dried polymer obtained in the drying step can be used as it is as a water absorbent resin powder. It is, however, preferable to control the dried polymer to have a specific particle size in order to improve the physical properties in a surface treatment step, especially in a surface crosslinking step (later described). The particle size of the dried polymer can be appropriately controlled not only in the pulverization step or the classification step but also in the polymerization step, a fine powder recycling step, a granulation step, or the like step. The particle size is defined by a standard sieve (JIS Z8801-1 (2000)).

A pulverizer that can be used in the pulverization step is not limited to a specific one. Examples of the pulverizer encompass a vibration mill, a roll granulator, a knuckle-type pulverizer, a roll mill, a high-speed pulverizer (such as a pin mill, a hammer mill, and a screw mill), a cylindrical mixer, and the like. Among these pulverizers, it is preferable to use a multiple-stage roll mill or roll granulator from the viewpoint of particle size control.

The classification step is carried out so that the water absorbent resin particles have the following particle size. In a case where surface crosslinking is carried out, it is preferable to carry out the classification step before the surface crosslinking step (first classification step). The classification step can be further carried out after the surface crosslinking step (second classification step). Note that how to carry out the classification step is not particularly limited. For example, the classification step is carried out by use of a sieve as below. In a case where a particle size distribution of the water absorbent resin particles is set to 150 μm to 850 μm, first, the pulverized substance is sieved by use of a sieve having a mesh size of 850 μm, and then a pulverized substance that has passed through the sieve is further sieved by use of a sieve having a mesh size of 150 μm or a sieve having a mesh size of more than 150 μm (for example, 200 μm). A pulverized substance left on the sieve having the mesh size of, for example, 150 μm is the water absorbent resin particles having an intended particle size distribution. The classification step can be carried out not only by sieve classification but also by classification by air by use of various classifiers.

The water absorbent resin particles have, after the classification step, a weight average particle diameter (D50) of preferably 250 μm to 500 μm, more preferably 300 μm to 500 μm, and still more preferably 350 μm to 450 μm, from the viewpoint of improvement in physical properties of the water absorbent resin powder obtainable by the present invention. Further, it is preferable that an amount of fine particles passing through a sieve having a mesh size of 150 μm (JIS standard sieve) be smaller. Specifically, the amount of such fine particles generally ranges preferably from 0 wt % to 5 wt %, more preferably from 0 wt % to 3 wt %, and still more preferably from 0 wt % to 1 wt %, based on the whole water absorbent resin particles. It is also preferable that a smaller amount of large particles does not pass through a sieve having a mesh size of not less than 850 μm (or not less than 710 μm) (JIS standard sieve). Specifically, the amount of such large particles generally ranges preferably from 0 wt % to 5 wt %, more preferably from 0 wt % to 3 wt %, and still more preferably from 0 wt % to 1 wt %, based on the whole water absorbent resin particles. In the present invention, a ratio of particles whose particle diameter is not less than 150 μm and less than 850 μm to the whole water absorbent resin particles, and further a ratio of particles whose particle diameter is not less than 150 μm and less than 710 μm to the whole water absorbent resin particles, are adjusted to preferably 95 wt % or more, and more preferably 98 wt % or more (an upper limit is 100 wt %). A logarithmic standard deviation ($\sigma\zeta$) of the particle size distribution preferably ranges from 0.20 to 0.50, more preferably from 0.25 to 0.50, still more preferably from 0.25 to 0.45, and particularly preferably from 0.30 to 0.40.

The particle size and the logarithmic standard deviation (σζ) of the particle size distribution are measured by the method described in the specification of European Patent No. 1594556. An additional standard sieve (mesh size) can be appropriately used for particle size measurement, depending on a particle size of a target to be measured. For example, the additional standard sieve only needs to be a standard sieve having a mesh size of 710 μm, 600 μm, or the like. The particle size before the surface crosslinking is applied preferably to the water absorbent resin powder which has been surface-crosslinked, and further to an end product.

(Internal Gas Bubbles Ratio)

The water absorbent resin powder obtainable by gel grinding of the present invention, and further preferably by drying at a specific temperature and at a specific air velocity can have a specific internal gas bubbles ratio. This is also applied to the water absorbent resin particles obtained in the pulverization step and the classification step. That is, the water absorbent resin particles which have not been surface-crosslinked preferably have (i) not less than 95 wt % of particles whose particle diameter is not less than 150 μm and less than 850 μm, (ii) the logarithmic standard deviation (σζ) of the particle size distribution in the range of 0.25 to 0.50, and (iii) the internal gas bubbles ratio of preferably 0% to 3.7%, more preferably 0.6% to 3.5%, still more preferably 1.0% to 3.3%, and particularly preferably 1.4% to 3.1%, the internal gas bubbles ratio being specified by the following equation:

(internal gas bubbles ratio)[%]={(true density)−(apparent density)}/(true density)×100

Note that a water absorbent resin which has not been surface-crosslinked is not limited to the water absorbent resin having the above internal gas bubbles ratio and the above particle size distribution. The following will describe the surface crosslinking of the present invention.

(3-5) Surface Treatment Step

The method for producing a polyacrylic acid (salt)-based water absorbent resin powder in accordance with the present invention preferably further includes a surface treatment step in order to improve water absorption performance (absorbency against pressure, liquid permeability, water absorbing speed, etc.). The surface treatment step includes a surface crosslinking step carried out by use of a known surface crosslinking agent by a known surface crosslinking method, and if necessary, further includes an addition step.

(Covalent Bonding Surface Crosslinking Agent)

The surface crosslinking agent for use in the present invention can be exemplified by various organic or inorganic crosslinking agents, but it is preferable that the surface crosslinking agent be an organic surface crosslinking agent. In terms of the physical properties, it is preferable to use, as the surface crosslinking agent, a dehydrative crosslinking agent such as (i) a polyvalent alcohol compound, (ii) an epoxy compound, (iii) a polyvalent amine compound or a condensed product with a halo epoxy compound of the polyvalent amine compound, (iv) an oxazoline compound, (v) a (mono, di, or poly)oxazolidinone compound, or (vi) an alkylene carbonate compound. In particular, it is possible to use a dehydrative crosslinking agent such as a polyvalent alcohol compound, an alkylene carbonate compound, or an oxazolidinone compound, which needs to react at a high temperature. In a case where a dehydrative crosslinking agent is not used, the surface crosslinking agent is more specifically exemplified by the compounds described in U.S. Pat. Nos. 6,228,930, 6,071,976, 6,254,990, and others. For example, the surface crosslinking agent is exemplified by polyvalent alcohol compounds, such as mono-, di-, tri-, tetra-propylene glycol, 1,3-propanediol, glycerin, 1,4-butanediol, 1,3-butanediol, 1,5-pentanediol, 1,6-hexanediol, and sorbitol; epoxy compounds, such as ethylene glycol diglycidyl ether, and glycidol; alkylene carbonate compounds, such as ethylene carbonate; oxetane compounds; cyclic urea compounds, such as 2-imidazolidinone; and others.

(Solvent and Others)

A used amount of the surface crosslinking agent is determined as appropriate, preferably in a range of 0.001 parts by weight to 10 parts by weight, and more preferably in a range of 0.01 parts by weight to 5 parts by weight, based on 100 parts by weight of the water absorbent resin particles. In addition to the surface crosslinking agent, water is preferably used in combination. An amount of the water as used preferably ranges from 0.5 parts by weight to 20 parts by weight, and more preferably from 0.5 parts by weight to 10 parts by weight, based on 100 parts by weight of the water absorbent resin particles. In case where an inorganic surface crosslinking agent and an organic surface crosslinking agent are used in combination, the surface crosslinking agents are each used in an amount preferably ranging from 0.001 parts by weight to 10 parts by weight, and more preferably from 0.01 parts by weight to 5 parts by weight, based on 100 parts by weight of the water absorbent resin particles.

In this case, a hydrophilic organic solvent can be used in an amount preferably in a range of 0 part by weight to 10 parts by weight, more preferably in a range of 0 part by weight to 5 parts by weight, based on 100 parts by weight of the water absorbent resin particles. In adding a crosslinking agent solution to the water absorbent resin particles, water-insoluble fine particle powder or a surfactant can be added as well in an amount not adversely affecting the effect of the present invention, for example, preferably in a range of 0 part by weight to 10 parts by weight, more preferably in a range of 0 part by weight to 5 parts by weight, and still more preferably in a range of 0 part by weight to 1 part by weight. Examples of a usable surfactant and a used amount of the surfactant are shown in U.S. Pat. No. 7,473,739, etc.

(Mixing)

In mixing the surface crosslinking agent with the water absorbent resin particles, a vertical or horizontal high-speed rotation stirring mixer is suitably used. The rotation rate of the mixer is preferably in a range of 100 rpm to 10000 rpm, and more preferably in a range of 300 rpm to 2000 rpm. Further, a residence time for which the water absorbent resin resides in the mixer is preferably within 180 seconds, more preferably in a range of 0.1 seconds to 60 seconds, and still more preferably in a range of 1 second to 30 seconds.

(Other surface crosslinking method)

In the present invention, it is possible to employ, instead of a method in which the surface crosslinking agent is used, a surface crosslinking method in which a radical polymerization initiator is used (U.S. Pat. No. 4,783,510, and International Publication No. 2006/062258), or a surface crosslinking method in which a monomer(s) is polymerized on a surface of water absorbent resin (U.S. Patent Application Publication Nos. 2005/048221 and 2009/0239966, and International Publication No. 2009/048160).

In the above surface crosslinking method, a preferable example of the radical polymerization initiator to be used is persulfate, a preferable example of the monomer(s) to be used as necessary is acrylic acid (salt) or the above-described crosslinking agents, and a preferable example of a solvent to be used is water. The materials are added onto the surface of the water absorbent resin, and then by an active energy line (particularly ultraviolet ray) or heat, crosslinking polymerization is carried out or a crosslinking reaction by use of the radical polymerization initiator is caused on the surface of the water absorbent resin. The surface crosslinking is thus carried out.

(Ionic bonding surface crosslinking agent)

The method for producing a polyacrylic acid (salt)-based water absorbent resin powder in accordance with the present invention further includes an addition step, carried out concurrently or separately with the surface crosslinking step, of adding at least one of a multivalent metal salt, a cationic polymer, and inorganic microparticles. Preferably, the method for producing a polyacrylic acid (salt)-based water absorbent resin powder in accordance with the present invention further includes an addition step of adding at least one of a multivalent metal salt and inorganic microparticles. That is, the liquid permeability, the water absorbing speed, and others can be improved by solely using the inorganic surface crosslinking agent or by using the inorganic surface crosslinking agent in combination with the organic surface crosslinking agent. The inorganic surface crosslinking agent can be used concurrently or separately with the organic surface crosslinking agent. Examples of the inorganic surface crosslinking agent to be used encompass divalent or greater, preferably trivalent or tetravalent metal salt (organic salt or inorganic salt), and hydroxide. Examples of a usable polyvalent metal include aluminum and zirconium, and the like, and the polyvalent metal is also exemplified by aluminum lactate and aluminum sulfate. An aqueous solution containing aluminum sulfate is preferably employed. The inorganic surface crosslinking agent is used concurrently or separately with the organic surface crosslinking agent. The surface crosslinking by use of the polyvalent metals is disclosed in International Publication Nos. 2007/121037, 2008/09843, and 2008/09842, U.S. Pat. Nos. 7,157,141, 6,605,673, and 6,620,889, and U.S. Patent Application Publication Nos. 2005/0288182, 2005/0070671, 2007/0106013, and 2006/0073969.

The liquid permeability and others can be improved by concurrent use or separate use of a cationic polymer particularly having weight average molecular weight of approximately 5,000 to 1,000,000. Preferable examples of the cationic polymer to be used include a vinyl amine polymer and the like (U.S. Pat. No. 7,098,284, International Publication Nos. 2006/082188, 2006/082189, 2006/082197, 2006/111402, 2006/111403, 2006/111404, and others).

Similarly, the inorganic microparticles can be added. Preferable examples of the inorganic microparticles include silicon dioxide and the like (U.S. Pat. No. 7,638,570 and others).

A preferable production method of the present invention is the method for producing a water absorbent resin including the addition step of adding at least one of the multivalent metal salt, the cationic polymer, and the inorganic microparticles. Such additives are preferably added concurrently or separately with the covalent bonding surface crosslinking agent. This makes it possible to further attain the object (improvement in liquid permeability, preferably in both liquid permeability and water absorbing speed) of the present invention.

(Physical properties after surface crosslinking)

It is preferable in the present invention that, with a reaction temperature, a reaction time, and others appropriately adjusted, the surface crosslinking be carried out so that water absorption capacity under load (AAP) of a water absorbent resin powder after the surface crosslinking is not less than 20 [g/g] (more preferably not less than 22 [g/g], still more preferably not less than 24 [g/g], and most preferably not less than 24.5 [g/g], and an upper limit of the AAP is preferably not more than 35 [g/g], more preferably not more than 30 [g/g], and still more preferably not more than 28 [g/g]) and so that water absorption capacity without load (CRC) after the surface crosslinking is not less than 10 [g/g] (more preferably not less than 20 [g/g], still more preferably not less than 25 [g/g], most preferably not less than 27 [g/g], and an upper limit of the CRC is preferably not more than 50 [g/g], more preferably not more than 45 [g/g], and still more preferably not more than 42 [g/g]).

(3-6) Other steps (fine powder recycling step and other steps)

Besides those steps described above, an evaporated monomer recycling step, a granulation step, a fine powder removal step, a fine powder recycling step, and/or the like can be provided, if necessary. Further, in order to attain a stability effect of color tone with the lapse of time, prevention of a gel deterioration, or the like, it is possible to use the following additive(s) in some or all of the steps, if necessary. That is, a water-soluble or water-insoluble polymer, a lubricant, a chelating agent, a deodorant, an antimicrobial agent, water, a surfactant, water-insoluble fine particles, anti-oxidant, a reducing agent, and/or the like can be added to and mixed with the water absorbent resin in an amount of preferably 0 wt % to 30 wt %, and more preferably 0.01 wt % to 10 wt %. Such an additive can also be used as a surface treatment agent.

The production method in accordance with the present invention can include the fine powder recycling step. The fine powder recycling step is a step of separating fine powder (particularly fine powder containing not less than 70 wt % of fine particles each having a particle diameter of not more than 150 μm) generated in the drying step, and further in the pulverization step and in the classification step (if the pulverization step and the classification step are carried out), and then recycling, in the polymerization step or in the drying step, the fine powder as it is or after being hydrated. The methods disclosed in U.S. Patent Application Publication No. 2006/247351, U.S. Pat. No. 6,228,930, and others can be applied to the fine powder recycling step of the present invention.

Furthermore, according to specific purposes, the water absorbent resin can contain an oxidant, an anti-oxidant, water, a polyvalent metal compound, a water-insoluble inorganic or organic powder such as silica or metal soap, a deodorant, an antimicrobial agent, polymer polyamine, pulps, thermoplastic fiber, and/or the like in an amount of 0 wt % to 3 wt %, and preferably 0 wt % to 1 wt %.

[4] Physical properties of polyacrylic acid (salt)-based water absorbent resin powder (4-1) AAP (Absorption Against Pressure)

In order to prevent leakage from disposable diapers, the water absorbent resin powder obtainable by the present invention has AAP under load of 4.8 kPa (water absorption capacity under load) preferably of not less than 17 [g/g], more preferably of not less than 20 [g/g], still more preferably of not less than 22 [g/g], further still more preferably of not less than 23 [g/g], and most preferably of not less than 24 [g/g] by, for example, the above-described polymerization. An upper limit of the AAP is not limited to a specific one. However, from the viewpoint of a balance with the other physical properties, the upper limit is preferably not more than 35 [g/g], more preferably not more than 30 [g/g], and still more preferably not more than 28 [g/g]. The AAP can be improved (adjusted) by the surface crosslinking after the particle size control. Note that a value of the AAP may vary depending on what step is carried out after the surface crosslinking step.

By carrying out the surface crosslinking so that the AAP is in the above range, it is possible to obtain a novel water absorbent resin of the present invention, and improve the liquid permeability (SFC) while keeping the water absorbing speed (FSR).

(4-2) SFC (Saline Flow Conductivity)

In order to prevent leakage from disposable diapers, saline flow conductivity (SFC) of the water absorbent resin powder obtainable by the present invention can be improved by the production method of the present invention, particularly by the surface crosslinking after the gel grinding, preferably after the particle size control of the present invention. The flow conductivity (SFC) for a 0.69 wt % sodium chloride aqueous solution (liquid permeability of a liquid against pressure) is preferably not less than 10 $[\times 10^{-7} \cdot cm^3 \cdot s \cdot g^{-1}]$, more preferably not less than 20 $[\times 10^{-7} \cdot cm^3 \cdot s \cdot g^{-1}]$, still more preferably not less than 30 $[\times 10^{-7} \cdot cm^3 \cdot s \cdot g^{-1}]$, further still more preferably not less than 50 $[\times 10^{-7} \cdot cm^3 \cdot s \cdot g^{-1}]$, particularly preferably not less than 70 $[\times 10^{-7} \cdot cm^3 \cdot s \cdot g^{-1}]$, and most preferably not less than 100 $[\times 10^{-7} \cdot cm^3 \cdot s \cdot g^{-1}]$ by, for example, surface crosslinking carried out so that the AAP is in the above range. The SFC is a well-known measurement method, and can be defined by, for example, the method described in U.S. Pat. No. 5,562,646. The present invention, which is more remarkably effective in attaining improvement in liquid permeability, particularly improvement in SFC, especially in attaining SFC in the above range, particularly SFC of not less than 10 $[\times 10^{-7} \cdot cm^3 \cdot s \cdot g^{-1}]$, is suitably applicable to a method for producing a water absorbent resin having such a high liquid permeability.

(4-3) CRC (water absorption capacity without load)

The water absorbent resin powder obtainable by the present invention has a CRC (water absorption capacity without load) preferably of not less than 10 [g/g], more preferably of not less than 20 [g/g], still more preferably of not less than 25 [g/g], and particularly preferably of not less than 27 [g/g]. An upper limit of the CRC is not limited to a specific one. However, from the viewpoint of the balance with the other physical properties, the upper limit is preferably not more than 50 [g/g], more preferably not more than 45 [g/g], still more preferably not more than 42 [g/g], and most preferably not more than 32 [g/g]. The CRC can be appropriately controlled by an amount of crosslinking agent during the polymerization and by the surface crosslinking after the polymerization (secondary crosslinking).

(4-4) Ext (Water Soluble Component)

In order to prevent stickiness or the like discomfort of disposable diapers in use due to leakage of liquid, the water absorbent resin powder obtainable by the present invention has Ext (a water soluble component) preferably of not more than 35 wt %, more preferably of not more than 25 wt %, still more preferably of not more than 15 wt %, and particularly preferably of not more than 10 wt %. The Ext can be appropriately controlled by an amount of crosslinking agent during the polymerization, and increase in amount of water soluble component during the gel grinding carried out after the polymerization.

(4-5) Residual Monomers

From the viewpoint of safety, the water absorbent resin powder obtainable by the present invention are controlled to have residual monomers normally of not more than 500 ppm, preferably of 0 ppm to 400 ppm, more preferably of 0 ppm to 300 ppm, and particularly preferably of 0 ppm to 200 ppm, by, for example, the above-described polymerization. The residual monomers can be appropriately controlled by, for example, a polymerization initiator during the polymerization and drying conditions after the polymerization.

(4-6) FSR (water absorbing speed)

In order to prevent leakage from disposable diapers, the water absorbent resin powder obtainable by the present invention has FSR (water absorbing speed) normally of not less than 0.2 [g/(g·s)], preferably of not less than 0.25 [g/(g·s)], more preferably of not less than 0.30 [g/(g·s)], still more preferably of not less than 0.35 [g/(g·s)], particularly preferably of not less than 0.40 [g/(g·s)], and most preferably of not less than 0.45 [g/(g·s)] by, for example, the above-described polymerization. An upper limit of the FSR is not more than 1.00 [g/(g·s)]. A method for measuring the FSR can be defined by International Publication No. 2009/016055. The FSR can be adjusted by the producing method of the present invention and by the particle size control carried out after drying.

The present invention, which is more remarkably effective in attaining improvement in water absorbing speed, particularly improvement in FSR, especially in attaining FSR in the above range, particularly FSR of not less than 0.30 [g/(g·s)], is suitably applicable to a method for producing a water absorbent resin having such a high water absorbing speed.

(4-7) Thermal conductivity

In order to improve a heat retaining property of disposable diapers, the water absorbent resin powder obtainable by the present invention has a thermal conductivity preferably of not more than 125 [mW/(m·K)], more preferably of not more than 120 [mW/(m·K)], and still more preferably of not more than 116 [mW/(m·K)]. Though depending on the type of measurement device, a lower limit of the thermal conductivity is generally 20 [mW/(m·K)].

(4-8) Ratio of particles smaller than 150 μm after impact resistance test

In order to improve a heat retaining property, handleability in fabricating disposable diapers, and liquid permeability, the water absorbent resin powder obtainable by the present invention after an impact resistance test contains particles smaller than 150 μm preferably in a ratio of 0 mass % to 4.5 mass %, more preferably in a ratio of 0 mass % to 4.0 mass %, still more preferably in a ratio of 0 mass % to 3.5 mass %, particularly preferably in a ratio of 0 mass % to 3.0 mass %, and most preferably in a ratio of 0 mass % to 2.5 mass %.

The impact resistance test will be described in detail later.

(4-9) Internal gas bubbles ratio

The water absorbent resin powder obtainable by the present invention has an internal gas bubbles ratio preferably of 0% to 3.7%, more preferably of 0.6% to 3.5%, still more preferably of 1.0% to 3.3%, and particularly preferably of 1.4% to 3.1%, the internal gas bubbles ratio being specified by the following equation:

(internal gas bubbles ratio)[%]={(true density)−(apparent density)}/(true density)×100.

The internal gas bubbles ratio falling within the above range facilitates improvement in both heat retaining property and liquid permeability.

(4-10) Mass average particle diameter D50, logarithmic standard deviation (σζ) of particle size distribution The water absorbent resin powder obtainable by the present invention has a mass average particle diameter D50 preferably of 250 μm to 500 μm, more preferably of 300 μm to 500 μm, still more preferably of 350 μm to 460 μm, from the viewpoint of improvement in physical properties.

Further, it is preferable that the water absorbent resin powder obtainable by the present invention contain a smaller amount of fine particles (particles smaller than 150 μm) that pass through a sieve having a mesh size of 150 μm (JIS standard sieve). Specifically, the amount of such fine particles normally ranges preferably from 0 mass % to 4.5 mass %, more preferably from 0 mass % to 4.0 mass %, still more preferably from 0 mass % to 3.5 mass %, particularly preferably from 0 mass % to 3.0 mass %, and most preferably from 0 mass % to 2.5 mass %, based on the whole water absorbent resin powder.

It is also preferable that the water absorbent resin powder obtainable by the present invention contain a smaller amount of large particles that do not pass through a sieve having a mesh size of not less than 850 μm (or not less than 710 μm) (JIS standard sieve). Specifically, the amount of such large particles normally ranges preferably from 0 mass % to 5 mass %, more preferably from 0 mass % to 3 mass %, and still more preferably from 0 mass % to 1 mass %, based on the whole water absorbent resin particles. Further, in accordance with the present invention, a ratio of particles whose particle diameter is not less than 150 μm and less than 850 μm based on the whole water absorbent resin particles, and further a ratio of particles whose particle diameter is not less than 150 μm and less than 710 μm based on the whole water absorbent resin particles, are adjusted to preferably not less than 95 mass %, and more preferably not less than 98 mass % (an upper limit is 100 mass %).

Further, from the viewpoint of improvement in heat retaining property, the water absorbent resin powder contains, in a ratio preferably of not more than 36 mass %, more preferably of not more than 34 mass %, and still more preferably of not more than 32 mass %, particles that pass through a sieve having a mesh size of 710 μm and do not pass through a sieve having a mesh size of 500 μm.

Still further, water absorbent resin powder obtainable by the present invention has a logarithmic standard deviation (σζ) of the particle size distribution preferably of 0.20 to 0.50, more preferably of 0.25 to 0.50, still more preferably of 0.25 to 0.45, and particularly preferably of 0.30 to 0.40.

The particle size and the logarithmic standard deviation (σζ) of the particle size distribution are measured by the method described in the specification of European Patent No. 1594556. An additional standard sieve (mesh size) can be appropriately used for particle size measurement, depending on a particle size of a target to be measured. The particle size before the surface crosslinking is applied preferably to the water absorbent resin particles which have been surface-crosslinked, and further to an end product.

(4-11) Surface tension

The water absorbent resin powder obtainable by the present invention has a surface tension preferably of not less than 60.0 [mN/m], more preferably of not less than 65.0 [mN/m], still more preferably of not less than 67.0[mN/m], further still more preferably of not less than 69.0 [mN/m], particularly preferably of not less than 70.0 [mN/m], and most preferably of not less than 72.0 [mN/m], from the viewpoint of reducing an amount of return of a liquid from disposable diapers.

(4-12) Multivalent metal salt, inorganic microparticles

The water absorbent resin powder obtainable by the present invention, in order to improve its performance such as liquid permeability, preferably contains at least one of the aforementioned multivalent metal salt and inorganic microparticles. The at least one of the aforementioned multivalent metal salt and inorganic microparticles is/are contained in an amount preferably of 0.01 mass % to 1 mass % and more preferably of 0.02 mass % to 0.5 mass %.

[5] Application of polyacrylic acid (salt)-based water absorbent resin powder

An application of the water absorbent resin powder obtainable by the production method in accordance with the present invention is not limited to a specific one. However, the water absorbent resin powder is preferably used for absorbent articles such as disposable diapers, sanitary napkins, and incontinence pads. The water absorbent resin powder shows an excellent ability in a case where it is used in high-concentration diapers (disposable diapers each of which contains a large amount of water absorbent resin) having problems such as odor derived from a material, and coloring, particularly in a case where it is used in an upper layer part of an absorbent body of the absorbent article.

The absorbent article includes an absorbent body which can optionally contain other absorbent material(s) (fibrous material such as pulp fiber). The absorbent body has a water absorbent resin content (core concentration, i.e. water absorbent resin powder content based on a total amount of the water absorbent resin powder and the fibrous material) preferably in a range of 30 wt % to 100 wt %, more preferably in a range of 40 wt % to 100 wt %, still more preferably in a range of 50 wt % to 100 wt %, further still more preferably in a range of 60 wt % to 100 wt %, particularly preferably in a range of 70 wt % to 100 wt %, and most preferably in a range of 75 wt % to 95 wt %. For example, in a case where the water absorbent resin powder obtainable by the production method in accordance with the present invention is used at the above core concentration particularly in the upper layer part of the absorbent body, liquid is efficiently distributed in the absorbent body, and an amount of the liquid to be absorbed by the entire absorbent article is increased because the absorbent body has an excellent diffusivity of absorbed liquid such as urine thanks to a high liquid permeability of the absorbent body. It is further possible to provide the absorbent article in which the absorbent body keeps white color giving an impression of cleanness. Still further, such an absorbent article has an excellent heat retaining property and thus realizes a high degree of wear comfort in any environment.

EXAMPLES

The following discusses the present invention with reference to Examples. It should be noted that the present invention is not limited to the Examples. Unless otherwise stated, physical properties specified in claims or Examples of the present invention were obtained by EDANA and other measurement methods under conditions where a temperature was a room temperature (20° C. to 25° C.) and humidity was 50 RH %. For electric devices used in Examples and Comparative Examples, power sources of 200 V or 100 V and 60 Hz were used, unless otherwise stated. For convenience, "liter" may be referred to as "L" and "weight %" may be referred to as "wt %".

(a) CRC and gel CRC

CRC (water absorption capacity without load) was measured according to ERT441.2-02. Specifically, 0.200 g of a water absorbent resin was weighed and uniformly placed in an unwoven bag (60 mm×60 mm) and the bag was heat-sealed. Then, the bag was immersed in 1000 mL of a 0.9 wt % sodium chloride aqueous solution whose temperature was adjusted to 25° C.±3° C. After 30 minutes, the bag was pulled out and dewatered by use of a centrifugal separator (centrifuge manufactured by KOKUSAN Co., Ltd., type H-122) at 250 G for 3 minutes. Thereafter, a weight W1 [g] of the bag was measured. A bag containing no water absorbent resin was subjected to the same operation, and a weight W2 [g] of the bag was measured. CRC (water absorption capacity without load) was calculated based on the following Equation (3):

$$\text{CRC [g/g]} = \{(W1-W2)/(\text{weight of water absorbent resin})\} - 1 \quad \text{Equation (3)}$$

Meanwhile, gel CRC was obtained through the same operation as above except that 0.4 g of a hydrogel was used and a free swelling time was 24 hours. Furthermore, a resin solid content of the hydrogel was measured separately so as to obtain a weight of a water absorbent resin in 0.4 g of the hydrogel. Gel CRC was calculated based on Equation (4) below. Each sample was measured five times, and an average of values obtained by the measurement was employed.

$$\text{Gel CRC[g/g]} = \{(mwi-mb)-msi\times(Wn/100)\}/\{msi\times(Wn/100)\}. \quad \text{Equation (4)}$$

where msi is a weight [g] of the hydrogel before measurement;

mb is a weight [g] of Blank (unwoven bag only) which has freely swollen and been dewatered;

mwi is a weight [g] of the hydrogel which has freely swollen and been dewatered; and Wn is a solid content [wt %] of the hydrogel.

(b) Ext and gel Ext

Ext (water soluble component) was measured according to ERT470.2-02. Specifically, 1.000 g of a water absorbent resin and 200 mL of a 0.90 wt % sodium chloride aqueous solution were placed in a 250 mL plastic container with a lid, and stirred with a cylindrical stirrer of 3.5 cm in length and 6 mm in diameter at 400 rpm for 16 hours, so that a water soluble component in the water absorbent resin was extracted. The extracted solution was filtered by use of a sheet of filter paper (Advantec Toyo Kaisha, Ltd., Product name: JIS P 3801, No. 2, thickness 0.26 mm, retained particle diameter 5 μm), and 50.0 g of a filtrate thus obtained was employed as a measurement solution.

Subsequently, the measurement solution was titrated with a 0.1N—NaOH aqueous solution until the measurement solution had pH of 10, and then titrated with a 0.1N—HCl aqueous solution until the measurement solution had pH of 2.7. Then, titers ([NaOH] mL, [HCl] mL) were obtained. Furthermore, the same operation was carried out only with respect to a 0.90 wt % sodium chloride aqueous solution, and blank titers ([bNaOH] mL, [bHCl] mL) were obtained. In the case of the water absorbent resin of the present invention, from an average molecular weight of the monomers of the water absorbent resin and the titer obtained as a result of the above operation, Ext (water soluble component) was calculated based on the following Equation (5):

$$\text{Ext [wt \%]} = 0.1\times(\text{average molecular weight of monomers})\times 200\times 100\times([\text{HCl}]-[b\text{HCl}])/1000/1.000/50.0 \quad \text{Equation (5)}$$

Meanwhile, measurement of gel Ext was carried out in the same manner as the measurement of Ext except that 5.0 g of a hydrogel cut into pieces of approximately 1 mm to 5 mm square by scissors was used and a stirring time was 24 hours. Furthermore, a resin solid content of the hydrogel was measured separately, the weight of the water absorbent resin of 5.0 g of the hydrogel was obtained, and the gel Ext was calculated based on the following Equation (6):

$$\text{Gel Ext[wt \%]} = \{(V_{HCl.s}-V_{HCl.b})\times C_{HCl}\times Mw\times F_{dil}\times 100\}/\{ms\times(Wn/100)\times 1000\}. \quad \text{Equation (6)}$$

where $V_{HCl.s}$ is an amount [mL] of HCl which is required for changing pH of a filtrate containing a dissolved polymer from 10 to 2.7;

$V_{HCl.b}$ is an amount [mL] of HCl which is required for changing pH of Blank (0.9 wt % sodium chloride aqueous solution) from 10 to 2.7;

$C_{HCl}$ is a concentration [mol/L] of an HCl solution;

Mw is an average molecular weight [g/mol] of monomer units in an acrylic acid (salt) polymer (e.g., Mw is 88.1 [g/mol] in a case where a neutralization ratio is 73 mol %);

$F_{dil}$ is a dilution ratio of a filtrate containing a dissolved polymer;

ms is a weight [g] of the hydrogel before measurement; and

Wn is a solid content [wt %] of the hydrogel.

(c) Weight average molecular weight of water soluble component

A weight average molecular weight of a water soluble component is obtained by measuring, with GPC, a weight average molecular weight of a polymer dissolved in the operations to measure the aforementioned Ext and gel Ext. The following describes the measurement with GPC.

In the measurement with GPC, TDA302 (Registered Trademark) manufactured by VISCOTECH CO., LTD. was used. This device includes a size exclusion chromatography, a refractive index detector, a light diffusion detector, and a capillary viscometer. The measurement device and the measurement conditions are as described below.

Pump/autosampler: GPCmax manufactured by VISCOTECH CO., LTD.

Guard column: SHODEX GF-7B

Column: two TOSOH GMPWXL connected in series

Detector: TDA302 manufactured by VISCOTECH CO., LTD. (temperature in the system was maintained at 30° C.)

Solvent: aqueous solution of 60 mM sodium dihydrogen phosphate dehydrate and 20 mM disodium hydrogen phosphate dodecahydrate Flow rate: 0.5 mL/min Pouring amount: 100 μL The device was calibrated by using polyoxyethylene glycol (weight average molecular weight (Mw) 22396, differential refractive index (dn/dc)=0.132, solvent refractive index 1.33) as a standard sample.

In a case where a material to be measured was a water absorbent resin obtained by polymerizing monomers containing 99 mol % or more acrylic acid (salt), measurement was carried out assuming that a differential refractive index (dn/dc) of a polymer to be analyzed was 0.12. In a case where a material to be measured was a copolymerized water absorbent resin whose monomer content other than acrylic acid (salt) was 1 mol % or more, measurement was carried out by use of a measured differential refractive index (dn/dc) in a solvent which index is unique to the macromolecules of the copolymerized water absorbent resin. Collection of data of a refractive index, a light scattering intensity, and a viscosity and analysis thereof were carried out by use of Viscotek OmniSEC 3.1 (Registered Trademark) software. A weight average molecular weight (Mw) was calculated based on data obtained from the refractive index and the light scattering intensity.

(d) Weight average particle diameter (D50) and logarithmic standard deviation (σζ) of particle size distribution A weight average particle diameter (D50) of a water absorbent resin and a logarithmic standard deviation (σζ) of a particle size distribution of the water absorbent resin were measured according to the measurement method described in European Patent No. 1594556. Meanwhile, a weight average particle diameter (D50) of a hydrogel and a logarithmic standard deviation (σζ) of particle size distribution of the hydrogel were measured according to the method below.

Specifically, 20 g of a hydrogel (solid content: α wt %) at a temperature of 20° C. to 25° C. was added to 500 g of a 20 wt % sodium chloride aqueous solution containing of 0.08 wt % EMAL 20C (surfactant, manufactured by Kao Corporation) (this aqueous solution is hereinafter referred to as "EMAL aqueous solution") to obtain a dispersion liquid. The dispersion liquid was stirred with a stirrer chip of 50 mm in length and 7 mm in diameter at 300 rpm for 60 minutes (an approximately 1.14 L polypropylene container having a cylindrical shape of 21 cm in height and 8 cm in diameter was used).

After the stirring, the dispersion liquid was poured onto a central part of a JIS standard sieve provided on a rotary table (diameter: 21 cm, mesh size of sieve, 8 mm/4 mm/2 mm/1 mm/0.60 mm/0.30 mm/0.15 mm/0.075 mm). All the hydrogel was washed out onto the sieve by use of 100 g of the EMAR aqueous solution. Then, in order that a water pouring range (50 $cm^2$) covered the whole sieve, 6000 g of the EMAR aqueous solution was evenly poured from a shower (pores: 72, liquid amount: 6.0 [L/min]), positioned 30 cm above the sieve, onto the sieve provided on the rotary table, which was being rotated with a hand (20 rpm). The hydrogel was thus classified. The hydrogel on the first-stage sieve which hydrogel was obtained as a result of the classification was dewatered for approximately 2 minutes, and then weighed. The hydrogels on the second-stage sieve and subsequent-stage sieves, which hydrogels were obtained as a result of the classification through the same operation, were dewatered, and the hydrogel remaining on each of the sieves was weighed.

According to the weight of the hydrogel remaining on each of the sieves, a wt % ratio of the hydrogel was calculated based on Equation (7) below. A mesh size of the sieve after the dewatering was found based on Equation (8) below, and a particle size distribution of the hydrogel was plotted on a logarithmic probability paper. A particle diameter whose cumulative sieve % R of the plot was equivalent to 50 wt % was regarded as a weight average particle diameter (D50) of the hydrogel. Furthermore, particle diameters when cumulative sieve % R=84.1% (referred to as X1) and cumulative sieve % R=15.9% (referred to as X2) were obtained from the above plot, and a logarithmic standard deviation (σζ) was obtained based on Equation (9) below. σζ having a smaller value means a narrower particle size distribution.

$X[\%]=(w/W)\times100$ Equation (7)

$R(\alpha)\,[mm]=(20/w)^{1/3}\times r$ Equation (8)

where

X is a wt % [%] of the hydrogel remaining on each of the sieves after being classified and dewatered;

w is a weight [g] of the hydrogel remaining on each of the sieves after being classified and dewatered;

W is a total weight [g] of the hydrogels remaining on the sieves after being classified and dewatered;

R(α) is a mesh size [mm] of a sieve in terms of a hydrogel whose solid content is α wt %; and r is a mesh size [mm] of a sieve with which a hydrogel having swollen in a 20 wt % sodium chloride aqueous solution is classified.

$\sigma\zeta=0.5\times\ln(X2/X1)$ Equation (9)

where X1 is a particle diameter when R is 84.1%, and X2 is a particle diameter when R is 15.9%.

(e) Apparent density

An apparent density of the water absorbent resin from which water had been removed was measured by use of a dry densimeter (a volume of the water absorbent resin having a predetermined weight was dry-measured). The apparent density is a density calculated in consideration of gas bubbles (internal gas bubbles) present inside a resin.

Specifically, 6.0 g of the water absorbent resin was weighed and placed in an aluminum cup whose bottom surface had a diameter of approximately 5 cm. Then, the water absorbent resin was dried in a windless drier at 180° C. The water absorbent resin was left to stand still for 3 hours or more until the moisture content of the water absorbent resin was 1 wt % or less, so that the water absorbent resin was dried sufficiently. An apparent density (unit: [$g/cm^3$]) of 5.00 g of the dried water absorbent resin was measured by use of an automatic dry densimeter (Accu-PycII 1340TC-10CC, manufactured by Shimadzu Corporation, carrier gas: helium). The measurement was repeated until five or more identical measured values were obtained consecutively.

(f) True density

Internal gas bubbles (closed cells) present inside the water absorbent resin have a diameter normally in a range of 1 μm to 300 μm. In pulverization, portions close to the closed cells are pulverized preferentially. For this reason, when the water absorbent resin is pulverized until a particle diameter thereof is less than 45 μm, the resultant water absorbent resin has almost no closed cells. Therefore, in the present invention, a dried density of the water absorbent resin having been pulverized to have a size of less than 45 μm was evaluated as a true density.

Specifically, 15.0 g of the water absorbent resin and 400 g of columnar porcelain balls (diameter: 13 mm, length: 13 mm) were placed in a ball mill pot (manufactured by TERAOKA, model No. 90, internal dimension: 80 mm in diameter and 75 mm in height, external dimension: 90 mm in diameter and 110 mm in height), and then the ball mill pot was operated at 60 Hz for 2 hours, so that a water absorbent resin which would pass through a JIS standard sieve having a mesh size of 45 μm (a water absorbent resin whose particle diameter was less than 45 μm) was obtained. Then, 6.0 g of that water absorbent resin whose particle diameter was less than 45 μm was dried at 180° C. for 3 hours or more as in the case of [Apparent density] described earlier, and thereafter the dried density was measured. The measurement value thus obtained was regarded as the "true density" of the present invention.

(g) Internal gas bubbles ratio

By use of an apparent density (ρ1 [$g/cm^3$]) measured by the method described earlier in [Apparent density] and a true density (ρ2 [$g/cm^3$]) measured by the method described earlier in [True density], an internal gas bubbles ratio of the water absorbent resin was calculated based on the following Equation (10):

Internal gas bubbles ratio $[\%]=(\rho2-\rho1)/\rho2\times100$ Equation (10)

(h) Water absorbing speed (Free swell rate) FSR

A water absorbing speed "FSR" of the present invention is an abbreviation for Free Swell Rate, and indicates water absorbing speed (free swell rate). Specifically, "FSR" refers to a speed (unit: [g/(g·s)]) of 1 g at which a water absorbent resin absorbs 20 g of a 0.9 wt % sodium chloride aqueous solution.

The following specifically describes a method for measuring FSR.

1.00 g of the water absorbent resin was placed in a 25 mL glass beaker (32 mm to 34 mm in diameter and 50 mm in height). The water absorbent resin was placed in the beaker in such a manner that a top surface of the water absorbent resin in the beaker was level. If necessary, a surface of the water absorbent resin can be made level by taking action, e.g., by tapping the beaker carefully. Then, 20.0 g of the 0.90 wt % sodium chloride aqueous solution adjusted to have a temperature of 23° C.±0.2° C. was weighed in a 50 mL glass beaker. The weighed sodium chloride was poured carefully and swiftly into the 25 mL beaker in which the water absorbent resin was placed. Time measurement was started concurrently with a contact between the poured sodium chloride aqueous solution and the water absorbent resin. Assume that a top surface of the sodium chloride aqueous solution in the beaker to which the sodium chloride aqueous solution had been poured was visually observed at an angle of approximately 20°. In this case, when the top surface of the sodium chloride aqueous solution was replaced with a surface of the water absorbent resin which surface had absorbed the sodium chloride aqueous solution by absorption of the sodium chloride aqueous solution by the water absorbent resin the time measurement was ended (time ts [sec.]). FSR was calculated based on the following Equation (11):

$$FSR [g/(g \cdot s)] = 20.0/(ts [sec.] \times 1.00) \quad \text{Equation (11)}$$

(i) Impact resistance test

A water absorbent resin powder was damaged by the method "(Mechanical Damage Test)" described in U.S. Pat. No. 6,562,879 and its corresponding Japanese Patent Application Publication Tokukai No. 2000-302876 (page, 12, paragraph [0058]). Specifically, 30 g of the water absorbent resin powder and 10 g of glass beads (approximately 6 mm in ball diameter, soda-lime glass beads for filling for super-fractionation) were placed in a glass container (manufactured by Nihon Yamamura Glass Co., Ltd., mayonnaise bottle, product name: A-29). The glass container was fixed by being sandwiched between clamps provided in a disperser (manufactured by Toyo Seiki Seisaku-sho, Ltd., No. 488 test disperser). Vibrations at a rotation rate of 750 cpm were transmitted to the glass container at 100 V/60 Hz for 30 minutes. This causes the container fixed to the disperser to (i) tilt in each of a rightward direction and a leftward direction by 12.5° (25° in total) with respect to a surface of the disperser to which surface the clamps were attached, and (ii) vibrate in each of a backward direction and a forward direction by 8 mm (16 mm in total), so that an impact was made on the water absorbent resin powder in the container.

The impact is a force empirically set as a representative of an impact force that is applied to the water absorbent resin powder which is being produced. The impact can be widely used as damage during transportation after production of an absorbent body and damage during production of the absorbent body.

After the impact resistance test, 10 g of the water absorbent resin powder was classified by use of a JIS standard sieve having a mesh size of 150 μm (JISZ8801-1(2000)) or a sieve equivalent to the JIS standard sieve. The classification was carried out under the following condition. That is, the classification was carried out by use of a vibration classifier (IIDA SIEVE SHAKER, TYPE: ES-65, SER.No. 0501) for 5 minutes. After the classification, a ratio [mass %] of particles of less than 150 μm in particle diameter was calculated by use of a mass of the particles of less than 150 μm in particle diameter based on the following equation:

ratio [mass %] of particles of less than 150 μm in
  particle diameter after impact resistance test={
  (mass [g] of particles having passed through
  sieve having a mesh size of 150 μm)/(mass [g]
  of water absorbent resin powder)}×100

(j) Thermal conductivity

A thermal conductivity of the water absorbent resin powder from which water had been removed was measured by a hot-wire method. Specifically, 150 g of the water absorbent resin powder was dispersed in a stainless vat (of 29 cm in length, 29 cm in breadth, and 5 cm in height) and then left to stand still in a reduced-pressure drier (manufactured by AS ONE Corporation, ETTAS AVO-310NB) whose temperature was adjusted to 80° C. A pressure in the drier was reduced by a small oil-sealed rotary vacuum pump (manufactured by ULVAC KIKO Inc., GLD-136C) until the pressure in the drier was 100 Pa or less, so that the water absorbent resin powder was dried under the reduced pressure. This operation was repeated until a solid content of the water absorbent resin powder was 97%±0.5%.

A thermal conductivity of the dried water absorbent resin powder was measured by use of a thermal conductivity meter (manufactured by Kyoto Electronics Manufacturing Co., Ltd., Quick Thermal Conductivity Meter QTM500).

A powder container of the device has an internal space that has a quadrangular tubular shape having a length of 30 mm, a breadth of 100 mm, a height of 60 mm, and a thickness of 5 mm. A polyimide film of 25 μm in thickness was provided as a bottom surface, and a place 3.3 mm above the bottom surface is marked with a gauge indicative of 100 mL. A probe is unique to the device, and is configured such that a heater of 1.5 mm in width and 90 mm in length and a thermocouple are attached to a base material whose thermal conductivity is known. During the measurement, the heater and the thermocouple each contact a powder sample via the polyimide film serving as the bottom surface of the powder container. The device is operated from a power source of 100V and 50 Hz. Before the measurement, the device was calibrated by measuring three types of standard samples whose thermal conductivities are known (0.0362 [W/(m·K)], 0.238 [W/(m·K)], 1.416 [W/(m·K)]).

The water absorbent resin powder whose temperature was adjusted to 25° C. was slowly poured into the powder container from a rim of the container in such a manner that the water absorbent resin powder reached a scale mark at 100 mL of the powder container. A surface of the water absorbent resin powder was evened by use of a spatula or the like so that the surface aligned with the gauge, and an opening part in an upper part of the powder container was covered with aluminum foil so as to prevent a sample from scattering. A bulk specific gravity obtained from a mass of the water absorbent resin powder which had filled the powder container was set to be larger by 10 % ±2% than a bulk specify gravity obtained by EDANA. Thereafter, the power container filled with the water absorbent resin powder was brought into contact with the probe, and an electric current was applied, so that heating was started. A heating condition in this case was set so that a temperature at which the powder that continued to be heated was saturated was higher by 15° C.±1° C. than a temperature of the powder that had not been heated. Temperatures of the heater were read by use of the thermocouple 30 seconds and 60 seconds after the application of the electric current, and a thermal conductivity was calculated based on Equation (12) below. The thermal conductivity thus obtained was rounded to be given to three significant figures.

$$\lambda = \{K \times R \times I^2 \times \ln(t2/t1)/(T2-T1)-H\} \times 1000 \qquad \text{Equation (12)}$$

where

λ is thermal conductivity [mW/(m·K)];

K and H are each probe constant;

R is thermal resistance per unit length of probe heater [Ω/m];

I is heating current [A];

t1 and t2 are each time [s] after application of electric current (t1=30, t2=60); and T1 and T2 are temperatures [° C.] at t1 and t2, respectively.

(k) Apparent heat loss amount

An apparent heat loss amount of the water absorbent resin powder in accordance with the present invention was measured as below.

Figure 8:
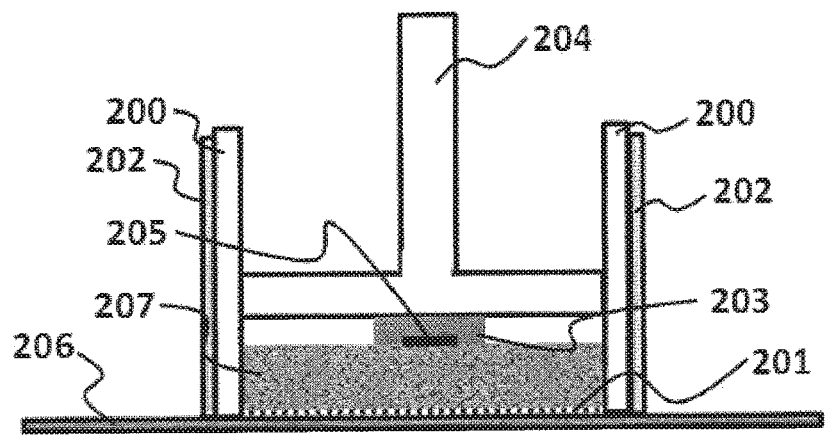
FIG. 8 is a cross-sectional view schematically illustrating a device in accordance with the present invention for use in measurement of an apparent heat loss amount.

According to the device illustrated in FIG. 8, a cylindrical acrylic resin cell (bottom area 28.3 cm²) 200 which has an inner diameter of 60 mm and a thickness of 5 mm and which has a bottom to which a woven stainless wire 201 of 400 meshes is attached and a side surface to which a heat insulating material 202 is attached is placed on a hot plate (manufactured by AS ONE Corporation, NEO HOTPLATE HI-1000) 206. In the cylindrical acrylic resin cell, a vinyl chloride resin piston 204 which has a diameter of 59 mm and a weight of 62 g is provided. A heat insulating material 203 having a length of 2 cm, a breadth of 2 cm, and a height of 1 cm is attached to a center of a bottom of the piston. A thermocouple 205 is provided on the heat insulating member. Over the woven wire 201, 30 g of the water absorbent resin powder was evenly dispersed, and the piston 204 was placed on the woven wire 201 so as not to compress the water absorbent resin powder. Then, the cylindrical acrylic resin cell was placed on the hot plate 206 which had been heated to 50° C., and the water absorbent resin powder 207 started to be heated. A powder temperature T1 [° C.] was measured 15 minutes after a powder temperature measured by the thermocouple 205 reached 24° C. An apparent heat loss amount Qs [J] was calculated based on the following Equation (13):

$$Qs\ [J] = K \times (50 - T1)/0.0133 \times 0.00283 \times 900 + (T1 - 23.5) \times 0.00283 \times 5 \times 900 \qquad \text{Equation (13)}$$

where K [W/(m·K)] is a thermal conductivity of the water absorbent resin powder and T1 [° C.] is a temperature obtained 15 minutes after the temperature of the water absorbent resin powder reached 24° C.

An apparent heat loss amount of 150 μm-passing particles (particles having passed through the sieve having a mesh size of 150 μm) of a water absorbent resin powder (17) obtained in Example 17 (described later) was measured by the above method, and the apparent heat loss amount was found to be 471 [J]. Since the apparent heat loss amount of the water absorbent resin powder (17) is 460 [J], it is found that more 150 μm-passing particles increase the apparent heat loss amount and consequently causes a deterioration in heat retaining property. This shows that the water absorbent resin powder in accordance with the present invention preferably has fewer 150 μm-passing particles from the viewpoint of an improvement in heat retaining property.

(1) Absorbent body heat loss amount

An absorbent body heat loss amount of the absorbent body in accordance with the present invention was measured as below.

Figure 9:
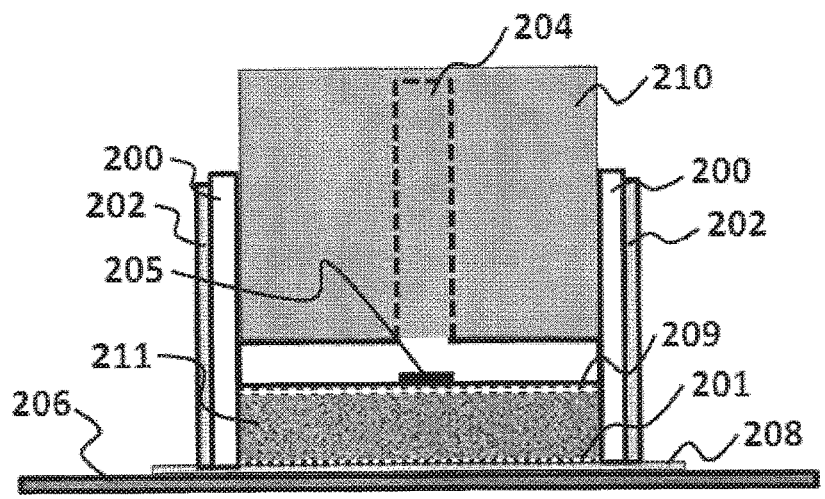
FIG. 9 is a cross-sectional view schematically illustrating a device in accordance with the present invention for use in measurement of an absorbent body heat loss amount.

According to the device illustrated in FIG. 9, a top sheet 208 of a disposable diaper and a cylindrical acrylic resin cell (bottom area 28.3 cm²) 200 which has an inner diameter of 60 mm and a thickness of 5 mm are placed in this order on a hot plate (manufactured by AS ONE Corporation, NEO HOTPLATE HI-1000) 206. The cylindrical acrylic resin cell has a bottom to which a woven stainless wire 201 of 400 meshes is attached and a side surface to which a heat insulating material 202 is attached. The cylindrical acrylic resin cell is arranged such that (i) a vinyl chloride resin piston 204 which has a diameter of 59 mm and a weight of 62 g and which has a thermocouple 205 provided at a center of a bottom thereof, and (ii) a weight 210 (of 1278 g in mass) for applying a load are provided therein. Onto the woven wire 201, 30 g of the absorbent body was introduced, and a back sheet 209 of a disposable diaper, the piston 204, and the weight 210 were placed on the absorbent body 211. Then, the cylindrical acrylic resin cell was placed on the top sheet 208 and the hot plate 206 which had been heated to 50° C., and the absorbent body started to be heated. An absorbent body temperature T2 [° C.] was measured 15 minutes after an absorbent body temperature measured by the thermocouple 205 reached 30° C. An absorbent body heat loss amount Qd [J] was calculated based on the following Equation (14):

$$Qd\ [J] = 30 \times 1 \times (T2-30) \qquad \text{Equation (14)}$$

Production Example 1

A hydrogel was produced according to Production Example 1 of WO 2011/126079.

As a device for producing a polyacrylic acid (salt)-based water absorbent resin powder, there was prepared a continuous production device for carrying out a polymerization step, a gel grinding step, a drying step, a pulverization step, a classification step, a surface crosslinking step, a cooling step, a particle sizing step, and a transportation step for linking the above individual steps. The continuous production device had a production capacity of approximately 3500 [kg/hr]. The above steps can each include a single line or two or more lines. In a case where the above steps each include two or more lines, the production capacity is shown as a sum of respective production amounts of the two or more lines. The continuous production device was used to continuously produce a polyacrylic acid (salt)-based water absorbent resin powder.

First, there was prepared a monomer aqueous solution (1) containing (i) 193.3 parts by weight of acrylic acid, (ii) 64.4 parts by weight of a 48 wt % sodium hydroxide aqueous solution, (iii) 1.26 parts by weight of polyethylene glycol diacrylate (average n number: 9), (iv) 52 parts by weight of a 0.1 wt % pentasodium ethylenediamine tetra(methylene phosphonate) aqueous solution, and (v) 134 parts by weight of deionized water.

Subsequently, the monomer aqueous solution (1) whose temperature was adjusted to 40° C. was continuously fed by use of a metering pump, and then 97.1 parts by weight of a 48 wt % sodium hydroxide aqueous solution was continuously line-mixed with the monomer aqueous solution (1). In this case, a temperature of the monomer aqueous solution (1) was raised to 85° C. due to heat of neutralization.

Furthermore, 8.05 parts by weight of a 4 wt % sodium persulfate aqueous solution was continuously line-mixed with the monomer aqueous solution (1), and then a resultant solution was continuously fed to a continuous polymerization device having a planar polymerization belt with a dam at each end, so that the fed mixture had a thickness of approximately 7.5 mm. Thereafter, polymerization (polymerization time: 3 minutes) was carried out continuously, so that a hydrogel (1) in the shape of a belt was obtained. The belt-shaped hydrogel (1) had CRC of 28.1 [g/g], a resin solid content of 53.1 wt %, a water soluble component of 4.1 wt %, and a weight average molecular weight of the water soluble component of $21.8 \times 10^4$ [Da].

Thereafter, the belt-shaped hydrogel (1) was continuously cut at regular intervals in a width direction relative to a traveling direction of the polymerization belt so that a cut length was approximately 300 mm. A hydrogel (1) obtained by the cutting (herein also referred to as "cut hydrogel (1)") was thus obtained.

Production Example 2

The same operations as those of Production Example 1 were carried out except that a used amount of polyethylene glycol diacrylate (average n number: 9) was changed to 1.05 parts by weight, so that a belt-shaped hydrogel (2) and a cut hydrogel (2) were obtained. The belt-shaped hydrogel (2) had CRC of 28.6 [g/g], a resin solid content of 53.0 wt %, a water soluble component of 4.2 wt %, and a weight average molecular weight of the water soluble component of $26.2 \times 10^4$ [Da].

Thereafter, the belt-shaped hydrogel (2) was continuously cut at regular intervals in a width direction with respect to a traveling direction of the polymerization belt so that a cut length was approximately 300 mm. A hydrogel (2) obtained by the cutting (herein also referred to as "cut hydrogel (2)") was thus obtained.

Production Example 3

The same operations as those of Production Example 1 were carried out except that a used amount of polyethylene glycol diacrylate (average n number: 9) was changed to 0.84 parts by weight, so that a belt-shaped hydrogel (3) and a cut hydrogel (3) were obtained. The belt-shaped hydrogel (3) had CRC of 30.2 [g/g], a resin solid content of 53.0 wt %, a water soluble component of 4.9 wt %, and a weight average molecular weight of the water soluble component of $35.4 \times 10^4$ [Da].

Production Example 4

The same operations as those of Production Example 1 were carried out except that a used amount of polyethylene glycol diacrylate (average n number: 9) was changed to 0.31 parts by weight, so that a belt-shaped hydrogel (4) and a cut hydrogel (4) were obtained. The belt-shaped hydrogel (4) had CRC of 41.3 [g/g], a resin solid content of 52.8 wt %, a water soluble component of 8.0 wt %, and a weight average molecular weight of the water soluble component of $73.6 \times 10^4$ [Da].

Production Example 5

The same operations as those of Production Example 1 were carried out except that points below were added to and changed from those of Production Example 1.

Specifically, a used amount of polyethylene glycol diacrylate (average n number: 9) was changed to 1.05 parts by weight, and 52 parts by weight of the 0.1 wt % pentasodium ethylenediamine tetra(methylene phosphonate) aqueous solution was replaced with 0.026 parts by weight of a 45 wt % diethylenetriamine pentaacetic acid trisodium salt aqueous solution. Moreover, a used amount of deionized water was changed from 134 parts by weight to 185 parts by weight, and 0.20 parts by weight of a 10 wt % polyoxyethylene (20) sorbitane monostearate (manufactured by Kao Corporation) aqueous solution was added to the monomer aqueous solution. Furthermore, concurrently with the 4 wt % sodium persulfate aqueous solution, 0.122 parts by weight of nitrogen gas was introduced, via a part different from a part via which the 4 wt % sodium persulfate aqueous solution was introduced, and was continuously line-mixed with the monomer aqueous solution.

A belt-shaped hydrogel (5) was thus obtained. The belt-shaped hydrogel (5) had CRC of 27.2 [g/g], a resin solid content of 53.5 wt %, a water soluble component of 4.0 wt %, and a weight average molecular weight of the water soluble component of $27.8 \times 10^4$ [Da].

Thereafter, the belt-shaped hydrogel (5) was continuously cut at regular intervals in a width direction relative to a traveling direction of the polymerization belt so that a cut length was approximately 200 mm. A hydrogel (5) obtained by the cutting (herein also referred to as "cut hydrogel (5)") was thus obtained.

Table 1 shows a shape of a screw of the gel grinding device which screw was used in each of Examples and Comparative Examples. Table 2 shows a shape of a barrel of the gel grinding device which barrel was used in each of Examples and Comparative Examples. Note that the barrel used in each of Examples and Comparative Examples was set at a barrel set angle θ of 37°.

TABLE 1

| | <Shape of screw> | | | | | |
|---|---|---|---|---|---|---|
| Screw No. | External diameter of screw [mm] | Shaft diameter of screw [mm] | Flight thickness of screw [mm] | Number of windings of screw | Pitch length of first winding of screw [mm] | Cross sectional area B [mm²] |
| S53-422 | 53 | 21 | 1.75 | 4.5 | 22 | 374 |
| S86-445 | 86 | 41 | 5 | 4 | 59.1 | 1433 |
| S130-4710 | 130 | 74 | 10 | 4.7 | 48 | 4581 |
| S175-51017 | 175 | 105 | 17 | 5.5 | 75 | 9254 |

TABLE 2

<Shape of barrel>

| Barrel No. | Inner diameter N of barrel [mm] | Number of threads of barrel | Ridge height YH of barrel [mm] | Ridge width YF of barrel [mm] | Cross sectional area A [mm$^2$] | Barrel ridge height-to-inner diameter ratio YH/N | Barrel ridge width-to-inner diameter ratio YF/N |
|---|---|---|---|---|---|---|---|
| B58-833 | 58 | 8 | 2.8 | 2.8 | 2642 | 0.048 | 0.048 |
| B88-844 | 88 | 8 | 4 | 4 | 6082 | 0.045 | 0.045 |
| B88-848 | 88 | 8 | 4 | 8 | 6082 | 0.045 | 0.091 |
| B88-874 | 88 | 8 | 7 | 4 | 6082 | 0.080 | 0.045 |
| B88-448 | 88 | 4 | 4 | 8 | 6082 | 0.045 | 0.091 |
| B88-4416 | 88 | 4 | 4 | 16 | 6082 | 0.045 | 0.182 |
| B88-474 | 88 | 4 | 7 | 4 | 6082 | 0.080 | 0.045 |
| B88-4164 | 88 | 4 | 16 | 4 | 6082 | 0.182 | 0.045 |
| B88-478 | 88 | 4 | 7 | 8 | 6082 | 0.080 | 0.091 |
| B88-278 | 88 | 2 | 7 | 8 | 6082 | 0.080 | 0.091 |
| B88-178 | 88 | 1 | 7 | 8 | 6082 | 0.080 | 0.091 |
| B136-6810 | 136 | 6 | 8 | 10 | 14527 | 0.059 | 0.074 |
| B181-71520 | 181 | 7 | 15 | 20 | 25730 | 0.083 | 0.110 |

Comparative Example 1

The cut hydrogel (1) obtained in Production Example 1 was fed to the gel grinding device in accordance with the present invention and subjected to gel grinding. As the screw and the barrel of the gel grinding device, screw No. S53-422 shown in Table 1 and barrel No. B58-833 shown in Table 2, respectively, were used. Furthermore, the gel grinding device was provided with a porous plate of 68 mm in diameter, 7.5 mm in die pore diameter, and 8 mm in die thickness. Table 3 shows a YH/N value of the gel grinding device and a YF/N value of the gel grinding device.

The cut hydrogel (1) was fed at 360 [g/min] (60 g of the gel was introduced every 10 seconds) while a rotation rate of a rotating shaft of the screw provided in the gel grinding device was set at 172 rpm. A comparative particulate hydrogel (1) was thus obtained. In this case, gel grinding energy (2) (GGE (2)) was 20.5 [J/g], and a treatment amount-to-inner diameter ratio T/N$^3$ was 0.11 [g/hr/mm$^3$].

(Drying, pulverization, classification, surface crosslinking, etc.)

Subsequently, the comparative particulate hydrogel (1) was dispersed over a drying net of a hot air drier. A temperature of the comparative particulate hydrogel (1) in this case was 80° C. After the dispersion, the comparative particulate hydrogel (1) was dried at 190° C. for 30 minutes, so that a comparative dried polymer (1) was obtained. An average air velocity of hot air of the hot air drier was 1.0 [m/s] in a direction vertical to a plane of the drying net. The air velocity of the hot air was measured by use of Anemomaster 6162 which was a constant temperature thermal anemometer manufactured by Kanomax Japan Inc.

Then, a total amount of the comparative dried polymer (1) at approximately 30° C. (after cooling) obtained in the drying step was fed to a roll mill and pulverized (subjected to a pulverization step), and then classified by use of JIS standard sieves having respective mesh sizes of 710 μm and 150 μm, so that particles of more than 710 μm and particles of less than 150 μm were removed. Comparative water absorbent resin particles (1) which were ground to have an uneven shape were thus obtained.

Then, a (covalent bonding) surface crosslinking agent solution containing 0.3 parts by weight of ethylene carbonate, 0.6 parts by weight of propylene glycol, and 3.0 parts by weight of deionized water was evenly mixed with 100 parts by weight of the comparative water absorbent resin particles (1), and a resultant mixture was subjected to a heat treatment at 208° C. for approximately 40 minutes, so that surface-crosslinked water absorbent resin particles were obtained. Thereafter, the surface-crosslinked water absorbent resin particles were cooled down. Then, an (ionic bonding) surface crosslinking agent solution containing 1.17 parts by weight of a 27.5 wt % aluminum sulfate aqueous solution (8 wt % in terms of aluminum oxide), 0.196 parts by weight of a 60 wt % sodium lactate aqueous solution, and 0.029 parts by weight of propylene glycol was evenly mixed with the surface-crosslinked water absorbent resin particles.

Thereafter, resultant particles were crushed (subjected to a particle sizing step) until the resultant particles passed through the JIS standard sieve having a mesh size of 710 μm, so that comparative water absorbent resin particles (1) and a comparative water absorbent resin powder (1) were obtained. Physical properties of the comparative water absorbent resin powder (1) are shown in Table 3. Physical properties of the comparative water absorbent resin particles (1) and the other physical properties of the comparative water absorbent resin powder are shown in Table 6.

Comparative Example 2

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-844 shown in Table 2, respectively, were used. Furthermore, the gel grinding device was provided with a porous plate of 100 mm in diameter, 9.5 mm in die pore diameter, and 10 mm in die thickness. Table 3 shows a YH/N value of the gel grinding device and a YF/N value of the gel grinding device.

The cut hydrogel (2) was fed at 10.64 [kg/min] (266 g of the gel was introduced every 1.5 seconds) while a rotation rate of a rotating shaft of the screw provided in the gel grinding device was set at 172 rpm. Concurrently with this, hot water at 70° C. was fed at 300 [g/min] and water vapor was fed at 83 [g/min]. A comparative particulate hydrogel (2) was thus obtained. In this case, gel grinding energy (2)

(GGE (2)) was 9.5 [J/g], and a treatment amount-to-inner diameter ratio $T/N^3$ was 0.94 [g/hr/mm$^3$].

Then, the comparative particulate hydrogel (2) thus obtained was subjected to the same operations (drying, pulverization, classification, surface crosslinking, etc.) as those of Comparative Example 1, so that comparative water absorbent resin particles (2) and a comparative water absorbent resin powder (2) were obtained. Physical properties of the comparative water absorbent resin powder (2) are shown in Table 3. Physical properties of the comparative water absorbent resin particles (2) and the other physical properties of the comparative water absorbent resin powder (2) are shown in Table 6.

Example 1

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-874 shown in Table 2, respectively, were used. The same operations as those of Comparative Example 2 were carried out, so that a particulate hydrogel (1), water absorbent resin particles (1), and a water absorbent resin powder (1) were obtained. In this case, gel grinding energy (2) (GGE (2)) was 7.7 [J/g]. A YH/N value of the gel grinding device and a YF/N value of the gel grinding device, and physical properties of the water absorbent resin powder (1) are shown in Table 3. Physical properties of the water absorbent resin particles (1) and the other physical properties of the water absorbent resin powder (1) are shown in Table 6.

Example 2

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-474 shown in Table 2, respectively, were used. The same operations as those of Comparative Example 2 were carried out, so that a particulate hydrogel (2), water absorbent resin particles (2), and a water absorbent resin powder (2) were obtained. In this case, gel grinding energy (2) (GGE (2)) was 8.1 [J/g]. A YH/N value of the gel grinding device and a YF/N value of the gel grinding device, and physical properties of the water absorbent resin powder (2) are shown in Table 3. Physical properties of the water absorbent resin particles (2) and the other physical properties of the water absorbent resin powder (2) are shown in Table 6.

Example 3

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-4164 shown in Table 2, respectively, were used. The same operations as those of Comparative Example 2 were carried out, so that a particulate hydrogel (3), water absorbent resin particles (3), and a water absorbent resin powder (3) were obtained. In this case, gel grinding energy (2) (GGE (2)) was 2.9 [J/g]. A YH/N value of the gel grinding device and a YF/N value of the gel grinding device, and physical properties of the water absorbent resin powder (3) are shown in Table 3. Physical properties of the water absorbent resin particles (3) and the other physical properties of the water absorbent resin powder (3) are shown in Table 6.

Example 4

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-848 shown in Table 2, respectively, were used. The same operations as those of Comparative Example 2 were carried out, so that a particulate hydrogel (4), water absorbent resin particles (4), and a water absorbent resin powder (4) were obtained. In this case, gel grinding energy (2) (GGE (2)) was 10.2 [J/g]. A YH/N value of the gel grinding device and a YF/N value of the gel grinding device, and physical properties of the water absorbent resin powder (4) are shown in Table 3. Physical properties of the water absorbent resin particles (4) and the other physical properties of the water absorbent resin powder (4) are shown in Table 6.

Example 5

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-448 shown in Table 2, respectively, were used. The same operations as those of Comparative Example 2 were carried out, so that a particulate hydrogel (5), water absorbent resin particles (5), and a water absorbent resin powder (5) were obtained. In this case, gel grinding energy (2) (GGE (2)) was 10.7 [J/g]. A YH/N value of the gel grinding device and a YF/N value of the gel grinding device, and physical properties of the water absorbent resin powder (5) are shown in Table 3. Physical properties of the water absorbent resin particles (5) and the other physical properties of the water absorbent resin powder (5) are shown in Table 6.

Example 6

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-4416 shown in Table 2, respectively, were used. The same operations as those of Comparative Example 2 were carried out, so that a particulate hydrogel (6), water absorbent resin particles (6), and a water absorbent resin powder (6) were obtained. In this case, gel grinding energy (2) (GGE (2)) was 12.4 [J/g]. A YH/N value of the gel grinding device and a YF/N value of the gel grinding device, and physical properties of the water absorbent resin powder (6) are shown in Table 3. Physical properties of the water absorbent resin particles (6) and the other physical properties of the water absorbent resin powder (6) are shown in Table 6.

Example 7

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-478 shown in Table 2, respectively, were used. The same operations as those of Comparative Example 2 were carried out, so that a particulate hydrogel (7), water absorbent resin particles (7), and a water absorbent resin powder (7) were obtained. In this case, gel grinding energy (2) (GGE (2)) was 8.8 [J/g]. A YH/N value of the gel grinding device and a YF/N value of the gel grinding device, and physical properties of the water absorbent resin powder (7) are shown in Table 3. Physical properties of the water absorbent resin particles (7) and the other physical properties of the water absorbent resin powder (7) are shown in Table 6.

Example 8

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-278 shown in Table 2, respectively, were used. The same operations as those of Comparative Example 2 were carried out, so that a particulate hydrogel (8), water absorbent resin particles (8), and a water absorbent resin powder (8) were obtained. In this case, gel grinding energy (2) (GGE (2)) was 9.7 [J/g]. A YH/N value of the gel grinding device and a YF/N value of the gel grinding device, and physical properties of the water absorbent resin powder (8) are shown in Table 3. Physical properties of the water absorbent resin particles (8) and the other physical properties of the water absorbent resin powder (8) are shown in Table 6.

Example 9

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-178 shown in Table 2, respectively, were used. The same operations as those of Comparative Example 2 were carried out, so that a particulate hydrogel (9), water absorbent resin particles (9), and a water absorbent resin powder (9) were obtained. In this case, gel grinding energy (2) (GGE (2)) was 11.7 [J/g]. A YH/N value of the gel grinding device and a YF/N value of the gel grinding device, and physical properties of the water absorbent resin powder (9) are shown in Table 3. Physical properties of the water absorbent resin particles (9) and the other physical properties of the water absorbent resin powder (9) are shown in Table 6.

Example 10

The cut hydrogel (2) obtained in Production Example 2 was fed to the gel grinding device in accordance with the present invention and subjected to gel grinding. As the screw and the barrel of the gel grinding device, screw No. S130-4710 shown in Table 1 and barrel No. B136-6810 shown in Table 2, respectively, were used. Furthermore, the gel grinding device was provided with a porous plate of 160 mm in diameter, 16 mm in die pore diameter, and 14 mm in die thickness. Table 3 shows a YH/N value of the gel grinding device and a YF/N value of the gel grinding device.

The cut hydrogel (2) was fed at 7.84 [kg/min] (196 g of the gel was introduced every 1.5 seconds) while a rotation rate of a rotating shaft of the screw provided in the gel grinding device was set at 115 rpm. Concurrently with this, hot water at 70° C. was fed at 282 [g/min]. A particulate hydrogel (10) was thus obtained. In this case, gel grinding energy (2) (GGE (2)) was 17.5 [J/g], and a treatment amount-to-inner diameter ratio $T/N^3$ was 0.19 [g/hr/mm$^3$].

Then, the particulate hydrogel (10) thus obtained was subjected to the same operations (drying, pulverization, classification, surface crosslinking etc.) as those of Comparative Example 1, so that water absorbent resin particles (10) and a water absorbent resin powder (10) were obtained. Physical properties of the water absorbent resin powder (10) are shown in Table 3. Physical properties of the water absorbent resin particles (10) and the other physical properties of the water absorbent resin powder (10) are shown in Table 6.

Example 11

The cut hydrogel (2) obtained in Production Example 2 was fed to the gel grinding device in accordance with the present invention and subjected to gel grinding. As the screw and the barrel of the gel grinding device, screw No. S175-51017 shown in Table 1 and barrel No. B181-71520 shown in Table 2, respectively, were used. Furthermore, the gel grinding device was provided with a porous plate of 220 mm in diameter, 16 mm in die pore diameter, and 25 mm in die thickness. Table 3 shows a YH/N value of the gel grinding device and a YF/N value of the gel grinding device.

The cut hydrogel (2) was fed at 39.1 [kg/min] (978 g of the gel was introduced every 1.5 seconds) while a rotation rate of a rotating shaft of the screw provided in the gel grinding device was set at 150 rpm. Concurrently with this, hot water at 70° C. was fed at 1.4 [kg/min]. A particulate hydrogel (11) was thus obtained. In this case, gel grinding energy (2) (GGE (2)) was 15.1 [J/g], and a treatment amount-to-inner diameter ratio $T/N^3$ was 0.40 [g/hr/mm$^3$].

Then, the particulate hydrogel (11) thus obtained was subjected to the same operations (drying, pulverization, classification, surface crosslinking etc.) as those of Comparative Example 1, so that water absorbent resin particles (11) and a water absorbent resin powder (11) were obtained. Physical properties of the water absorbent resin powder (11) are shown in Table 3. Physical properties of the water absorbent resin particles (11) and the other physical properties of the water absorbent resin powder (11) are shown in Table 6.

Comparative Example 3

The cut hydrogel (3) obtained in Production Example 3 was fed to the gel grinding device in accordance with the present invention and subjected to gel grinding. As the screw and the barrel of the gel grinding device, screw No. S86-445 shown in Table 1 and barrel No. B88-844 shown in Table 2, respectively, were used. The same operations as those of Comparative Example 2 were carried out, so that a comparative particulate hydrogel (3), comparative water absorbent resin particles (3), and a comparative water absorbent resin powder (3) were obtained. In this case, gel grinding energy (2) (GGE (2)) was 10.1 [J/g]. A YH/N value of the gel grinding device and a YF/N value of the gel grinding device, and physical properties of the comparative water absorbent resin powder (3) are shown in Table 4. Physical properties of the comparative water absorbent resin particles (3) and the other physical properties of the comparative water absorbent resin powder (3) are shown in Table 6.

Example 12

The cut hydrogel (3) obtained in Production Example 3 was fed to the gel grinding device in accordance with the present invention and subjected to gel grinding. As the screw and the barrel of the gel grinding device, screw No. S86-445 shown in Table 1 and barrel No. B88-478 shown in Table 2, respectively, were used. The same operations as those of Comparative Example 2 were carried out, so that a particulate hydrogel (12), water absorbent resin particles (12), and a water absorbent resin powder (12) were obtained. In this case, gel grinding energy (2) (GGE (2)) was 9.4 [J/g]. A YH/N value of the gel grinding device and a YF/N value of the gel grinding device, and physical properties of the water absorbent resin powder (12) are shown in Table 4. Physical properties of the water absorbent resin particles (12) and the other physical properties of the water absorbent resin powder (12) are shown in Table 6.

Comparative Example 4

The cut hydrogel (5) obtained in Production Example 5 was fed to the gel grinding device in accordance with the present invention and subjected to gel grinding. As the screw and the barrel of the gel grinding device, screw No. S86-445 shown in Table 1 and barrel No. B88-844 shown in Table 2, respectively, were used. The same operations as those of Comparative Example 2 were carried out, so that a comparative particulate hydrogel (4), comparative water absorbent resin particles (4), and a comparative water absorbent resin powder (4) were obtained. In this case, gel grinding energy (2) (GGE (2)) was 10.4 [J/g]. A YH/N value of the gel grinding device and a YF/N value of the gel grinding device, and physical properties of the comparative water absorbent resin powder (4) are shown in Table 5. Physical properties of the comparative water absorbent resin particles (4) and the other physical properties of the comparative water absorbent resin powder (4) are shown in Table 6.

Example 13

The cut hydrogel (5) obtained in Production Example 5 was fed to the gel grinding device in accordance with the present invention and subjected to gel grinding. As the screw and the barrel of the gel grinding device, screw No. S86-445 shown in Table 1 and barrel No. B88-478 shown in Table 2, respectively, were used. The same operations as those of Comparative Example 2 were carried out, so that a particulate hydrogel (13), water absorbent resin particles (13), and a water absorbent resin powder (13) were obtained. In this case, gel grinding energy (2) (GGE (2)) was 9.8 [J/g]. A YH/N value of the gel grinding device and a YF/N value of the gel grinding device, and physical properties of the water absorbent resin powder (13) are shown in Table 5. Physical properties of the water absorbent resin particles (13) and the other physical properties of the water absorbent resin powder (13) are shown in Table 6.

Example 14

The same operations as those of Example 1 were carried out except that an introduction amount (treatment amount) of the gel was changed from 10.64 [kg/min] to 17.2 [kg/min] (430 g of the gel was introduced every 1.5 seconds), so that a particulate hydrogel (14), water absorbent resin particles (14), and a water absorbent resin powder (14) were obtained. In this case, gel grinding energy (2) (GGE (2)) was 4.4 [J/g], and a treatment amount-to-inner diameter ratio $T/N^3$ was 1.51 [g/hr/mm$^3$]. A YH/N value of the gel grinding device and a YF/N value of the gel grinding device, and physical properties of the water absorbent resin powder (13) are shown in Table 3. Physical properties of the water absorbent resin particles (13) and the other physical properties of the water absorbent resin powder (13) are shown in Table 6.

TABLE 3

| | | Screw No. | Barrel No. | Barrel ridge height-to-inner diameter ratio YH/N | Barrel ridge width-to-inner diameter ratio YF/N | CRC [g/g] | FSR [g/g/s] | SFC [1] |
|---|---|---|---|---|---|---|---|---|
| Comparative Example 1 | Comparative water absorbent resin powder (1) | S53-422 | B58-833 | 0.048 | 0.048 | 26.8 | 0.35 | 98 |
| Comparative Example 2 | Comparative water absorbent resin powder (2) | S86-445 | B88-844 | 0.045 | 0.045 | 27.4 | 0.27 | 110 |
| Example 1 | Water absorbent resin powder (1) | S86-445 | B88-874 | 0.080 | 0.045 | 27.6 | 0.27 | 120 |
| Example 2 | Water absorbent resin powder (2) | S86-445 | B88-474 | 0.080 | 0.045 | 27.7 | 0.28 | 121 |

TABLE 3-continued

| | | Screw No. | Barrel No. | Barrel ridge height-to-inner diameter ratio YH/N | Barrel ridge width-to-inner diameter ratio YF/N | CRC [g/g] | FSR [g/g/s] | SFC [1)] |
|---|---|---|---|---|---|---|---|---|
| Example 3 | Water absorbent resin powder (3) | S86-445 | B88-4164 | 0.182 | 0.045 | 27.8 | 0.27 | 120 |
| Example 4 | Water absorbent resin powder (4) | S86-445 | B88-848 | 0.045 | 0.091 | 27.6 | 0.31 | 120 |
| Example 5 | Water absorbent resin powder (5) | S86-445 | B88-448 | 0.045 | 0.091 | 27.7 | 0.33 | 118 |
| Example 6 | Water absorbent resin powder (6) | S86-445 | B88-4416 | 0.045 | 0.182 | 27.7 | 0.34 | 119 |
| Example 7 | Water absorbent resin powder (7) | S86-445 | B88-478 | 0.080 | 0.091 | 28.0 | 0.34 | 123 |
| Example 8 | Water absorbent resin powder (8) | S86-445 | B88-278 | 0.080 | 0.091 | 28.0 | 0.35 | 120 |
| Example 9 | Water absorbent resin powder (9) | S86-445 | B88-178 | 0.080 | 0.091 | 28.0 | 0.36 | 121 |
| Example 10 | Water absorbent resin powder (10) | S130-4710 | B136-6810 | 0.059 | 0.074 | 28.0 | 0.34 | 123 |
| Example 11 | Water absorbent resin powder (11) | S175-51017 | B181-71520 | 0.083 | 0.110 | 28.1 | 0.34 | 123 |
| Example 14 | Water absorbent resin powder (14) | S86-445 | B88-874 | 0.080 | 0.045 | 27.6 | 0.27 | 116 |

1) [$10^{-7} \cdot cm^3 \cdot s/g$]

TABLE 4

| | | Screw No. | Barrel No. | Barrel ridge height-to-inner diameter ratio YH/N | Barrel ridge width-to-inner diameter ratio YF/N | CRC [g/g] | FSR [g/g/s] | SFC [1)] |
|---|---|---|---|---|---|---|---|---|
| Comparative Example 3 | Comparative water absorbent resin powder (3) | S86-445 | B88-844 | 0.045 | 0.045 | 30.0 | 0.22 | 50 |
| Example 12 | Water absorbent resin powder (12) | S86-445 | B88-478 | 0.080 | 0.091 | 30.6 | 0.26 | 53 |

1) [$10^{-7} \cdot cm^3 \cdot s/g$]

TABLE 5

| | | Screw No. | Barrel No. | Barrel ridge height-to-inner diameter ratio YH/N | Barrel ridge width-to-inner diameter ratio YF/N | CRC [g/g] | FSR [g/g/s] | SFC [1] |
|---|---|---|---|---|---|---|---|---|
| Comparative Example 4 | Comparative water absorbent resin powder (4) | S86-445 | B88-844 | 0.045 | 0.045 | 27.1 | 0.39 | 135 |
| Example 13 | Water absorbent resin powder (13) | S86-445 | B88-478 | 0.080 | 0.091 | 27.8 | 0.46 | 146 |

1) $[10^{-7} \cdot cm^3 \cdot s/g]$

TABLE 6

| | Water absorbent resin particles | | | | |
|---|---|---|---|---|---|
| | CRC [g/g] | Water soluble component [wt %] | Weight average particle diameter (D50) [μm] | Logarithmic standard deviation of particle size distribution (σζ) | 150 μm-passing particles [wt %] |
| Comparative Example 1 | 31.8 | 7.4 | 362 | 0.34 | 0.6 |
| Comparative Example 2 | 32.9 | 8.3 | 365 | 0.33 | 0.4 |
| Example 1 | 33.0 | 8.1 | 361 | 0.32 | 0.5 |
| Example 2 | 33.2 | 8.1 | 362 | 0.31 | 0.5 |
| Example 3 | 33.5 | 8.0 | 365 | 0.34 | 0.5 |
| Example 4 | 33.4 | 8.3 | 364 | 0.33 | 0.3 |
| Example 5 | 33.3 | 8.3 | 361 | 0.34 | 0.5 |
| Example 6 | 33.6 | 8.5 | 361 | 0.33 | 0.4 |
| Example 7 | 33.4 | 8.2 | 363 | 0.32 | 0.3 |
| Example 8 | 33.3 | 8.3 | 364 | 0.33 | 0.5 |
| Example 9 | 33.0 | 8.4 | 365 | 0.33 | 0.4 |
| Example 10 | 30.8 | 8.6 | 382 | 0.34 | 0.5 |
| Example 11 | 32.0 | 8.5 | 381 | 0.34 | 0.5 |
| Comparative Example 3 | 37.0 | 12.1 | 456 | 0.41 | 0.5 |
| Example 12 | 36.8 | 12.2 | 456 | 0.41 | 0.5 |
| Comparative Example 4 | 32.1 | 7.9 | 451 | 0.40 | 0.5 |
| Example 13 | 32.0 | 7.8 | 450 | 0.40 | 0.5 |
| Example 14 | 33.5 | 8.2 | 360 | 0.33 | 0.4 |

| | Water absorbent resin powder | | | |
|---|---|---|---|---|
| | Water soluble component [wt %] | Weight average particle diameter (D50) [μm] | Logarithmic standard deviation of particle size distribution (σζ) | 150 μm-passing particles [wt %] |
| Comparative Example 1 | 7.2 | 365 | 0.34 | 0.4 |
| Comparative Example 2 | 8.1 | 366 | 0.33 | 0.4 |
| Example 1 | 7.9 | 361 | 0.32 | 0.4 |
| Example 2 | 8.0 | 363 | 0.31 | 0.4 |
| Example 3 | 7.7 | 366 | 0.34 | 0.4 |
| Example 4 | 8.0 | 366 | 0.33 | 0.3 |
| Example 5 | 8.0 | 366 | 0.34 | 0.4 |
| Example 6 | 7.8 | 365 | 0.33 | 0.4 |
| Example 7 | 8.0 | 367 | 0.32 | 0.3 |
| Example 8 | 8.0 | 365 | 0.33 | 0.4 |
| Example 9 | 8.0 | 365 | 0.33 | 0.4 |
| Example 10 | 8.0 | 386 | 0.34 | 0.4 |
| Example 11 | 8.1 | 385 | 0.34 | 0.4 |
| Comparative Example 3 | 11.9 | 458 | 0.41 | 0.4 |
| Example 12 | 11.8 | 457 | 0.41 | 0.4 |
| Comparative Example 4 | 7.8 | 455 | 0.41 | 0.4 |
| Example 13 | 7.7 | 456 | 0.41 | 0.4 |
| Example 14 | 8.0 | 362 | 0.33 | 0.4 |

(Conclusion)

It is found that the comparative water absorbent resin powder (1), which was produced in Comparative Example 1, is high in water absorbing speed (FSR) but low in liquid permeability (SFC) and thus has not improved in both liquid permeability (SFC) and water absorbing speed (FSR).

It is found that the water absorbent resin powders (1) through (3), which were produced in respective Examples 1 through 3, in each of which the gel grinding device in accordance with the present invention which gel grinding device included the barrel satisfying 0.05≤YH/N≤0.25 was used, have further improved in both liquid permeability (SFC) and water absorbing speed (FSR) as compared with the comparative water absorbent resin powder (2), which was produced in Comparative Example 2.

It is found that the water absorbent resin powders (4) through (6), which were produced in respective Examples 4 through 6, in each of which the gel grinding device in accordance with the present invention which gel grinding device included the barrel satisfying 0.05≤YF/N≤0.25 was used, have further improved in both liquid permeability (SFC) and water absorbing speed (FSR) as compared with the comparative water absorbent resin powder (2), which was produced in Comparative Example 2.

It is found that the water absorbent resin powders (7) through (11), which were produced in respective Examples 7 through 11, in each of which the gel grinding device in accordance with the present invention which gel grinding device included the barrel satisfying both 0.05≤YH/N≤0.25 and 0.05≤YF/N≤0.25 was used, have further remarkably improved in liquid permeability (SFC) as compared with the comparative water absorbent resin powder (2), which was produced in Comparative Example 2.

Note here that having further improved in liquid permeability (SFC) means (i) exhibiting higher SFC as compared with SFC of a water absorbent resin powder having equal CRC, and (ii) exhibiting higher CRC as compared with CRC of a water absorbent resin powder having equal SFC.

It is found that the water absorbent resin powder (12), which was produced in Example 12, in which the gel grinding device in accordance with the present invention which gel grinding device included the barrel satisfying both $0.05 \leq YH/N \leq 0.25$ and $0.05 \leq YF/N \leq 0.25$ was used, has further remarkably improved in both liquid permeability (SFC) and water absorbing speed (FSR) as compared with the comparative water absorbent resin powder (3), which was produced in Comparative Example 3. Similarly, it is found that the water absorbent resin powder (13), which was produced in Example 13, in which the gel grinding device in accordance with the present invention which gel grinding device included the barrel satisfying both $0.05 \leq YH/N \leq 0.25$ and $0.05 \leq YF/N \leq 0.25$ was used, has further remarkably improved in both liquid permeability (SFC) and water absorbing speed (FSR) as compared with the comparative water absorbent resin powder (4), which was produced in Comparative Example 4.

Example 15

The following operation was carried out with reference to Example 6 of International Publication No. WO2011/126079.

The cut hydrogel (3) obtained in Production Example 3 was fed to the gel grinding device in accordance with the present invention and subjected to gel grinding. As the screw and the barrel of the gel grinding device, screw No. S86-445 shown in Table 1 and barrel No. B88-478 shown in Table 2, respectively, were used. Furthermore, the gel grinding device was provided with a porous plate of 100 mm in diameter, 12.5 mm in die pore diameter, and 10 mm in die thickness.

The cut hydrogel (3) was fed at 10.64 [kg/min] (266 g of the gel was introduced every 1.5 seconds) while a rotation rate of a rotating shaft of the screw provided in the gel grinding device was set at 172 rpm. Concurrently with this, hot water at 70° C. was fed at 300 [g/min] and water vapor was fed at 83 [g/min]. A particulate hydrogel (15) was thus obtained.

(Drying, pulverization, classification, surface crosslinking, etc.)

Subsequently, the particulate hydrogel (15) was dispersed over a drying net of a hot air drier. A temperature of the particulate hydrogel (15) in this case was 80° C. After the dispersion, the particulate hydrogel (15) was dried at 190° C. for 30 minutes, so that a dried polymer (15) was obtained. An average air velocity of hot air of the hot air drier was 1.0 [m/s] in a direction vertical to a plane of the drying net. The air velocity of the hot air was measured by use of Anemomaster 6162 which was a constant temperature thermal anemometer manufactured by Kanomax Japan Inc.

Then, a total amount of the dried polymer (15) at approximately 30° C. (after cooling) obtained in the drying step was pulverized by being continuously fed to a three-stage roll mill, so that a pulverized polymer (15) was obtained. Roll gaps of the three-stage roll mill were 0.8 mm, 0.65 mm, and 0.48 mm, respectively, in this order from above. A degree of reduced pressure in the pulverization step was set at 0.29 kPa.

After the pulverization step, the pulverized polymer (15) (approximately 60° C.) thus obtained was continuously classified, in accordance with the method disclosed in the International Publication No. WO 2011/034147 A 1 and by use of a sieving device including metal sieving nets having respective mesh sizes of 710 µm and 175 µm, into particles (A) which had not passed through a sieve of 710 µm, particles (B) which had passed through the sieve of 710 µm but had not passed through a sieve of 175 µm, and particles (C) which had passed through the sieve of 175 µm. The particles (A) which had not passed through the sieve of 710 µm were fed to the three-stage roll mill, where the particles (A) were pulverized again. A degree of reduced pressure in the classification step was 0.11 kPa, and air having a dew point of 10° C. and a temperature of 75° C. passed through the sieving device at 2 [m³/hr]. The sieving device used in the classification was a pivoted circular sieving device (number of vibrations: 230 rpm, radial inclination (gradient): 11 mm, tangential inclination (gradient): 11 mm, eccentric amount: 35 mm, temperature of device: 55° C.). A base on which the sieving device was provided was grounded (subjected to removal of electricity) at a grounding resistance of 5Ω. Water absorbent resin particles (15) having a particle diameter ranging from 710 µm to 175 µm were thus continuously obtained.

Then, a (covalent bonding) surface crosslinking agent solution containing 0.3 parts by mass of ethylene carbonate, 0.6 parts by mass of propylene glycol, and 3.0 parts by mass of deionized water was evenly mixed with 100 parts by mass of the water absorbent resin particles (15), and a resultant mixture was subjected to a heat treatment at 208° C. for approximately 40 minutes, so that surface-crosslinked water absorbent resin particles were obtained. Thereafter, the surface-crosslinked water absorbent resin particles were cooled down. Then, an (ionic bonding) surface crosslinking agent solution containing 1.17 parts by mass of a 27.5 mass % aluminum sulfate aqueous solution (8 mass % in terms of aluminum oxide), 0.196 parts by mass of a 60 mass % sodium lactate aqueous solution, and 0.029 parts by mass of propylene glycol was evenly mixed with the surface-crosslinked water absorbent resin particles.

Thereafter, resultant particles were crushed (subjected to a particle sizing step) until the resultant particles passed through the JIS standard sieve having a mesh size of 710 µm, so that a water absorbent resin powder (15) was obtained. The water absorbent resin powder (15) had 35.6 mass % of 500 µm-non-passing particles (a ratio of particles which had not passed through a sieve having a mesh size of 500 µm). The water absorbent resin powder (15) had a surface tension of 72.1 [mN/m]. Physical properties of the water absorbent resin powder (15) are shown in Table 7. Physical properties of the water absorbent resin particles (15) are shown in Table 8. The other physical properties of the water absorbent resin powder (15) are shown in Table 9.

Example 16

The same operations as those of Example 15 were carried out except that points below were added to and changed from those of Example 15.

The same operations as those of Example 15 were carried out except that conditions under which the heat treatment was carried out were changed from "at 208° C. for approximately 40 minutes" to "at 208° C. for approximately 30 minutes," so that water absorbent resin particles (16), and a water absorbent resin powder (16) were obtained. The water absorbent resin powder (16) had 34.8 mass % of 500 µm-non-passing particles. The water absorbent resin powder (16) had a surface tension of 72.0 [mN/m]. Physical properties of the water absorbent resin powder (16) are shown in Table 7. Physical properties of the water absorbent resin particles (16) are shown in Table 8. The other physical properties of the water absorbent resin powder (16) are shown in Table 9.

Example 17

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-478 shown in Table 2, respectively, were used. Furthermore, the gel grinding device was provided with a porous plate of 100 mm in diameter, 9.5 mm in die pore diameter, and 10 mm in die thickness. The same operations as those of Example 15 were carried out, so that a particulate hydrogel (17), water absorbent resin particles (17), and a water absorbent resin powder (17) were obtained. Particle sizes of the water absorbent resin powder (17) were such that the water absorbent resin powder (17) had 0 mass % of 710 μm-non-passing particles, 3.8 mass % of 600 μm-non-passing particles, 14.9 mass % of 500 μm-non-passing particles, 54.0 mass % of 300 μm-non-passing particles, 27.0 mass % of 150 μm-non-passing particles, and 0.3 mass % of 150 μm-passing particles (particles having passed through the sieve having a mesh size of 150 μm). The water absorbent resin powder (17) had a surface tension of 72.1 [mN/m]. Physical properties of the water absorbent resin powder (17) are shown in Table 7. Physical properties of the water absorbent resin particles (17) are shown in Table 8. The other physical properties of the water absorbent resin powder (17) are shown in Table 9.

Example 18

The cut hydrogel (2) obtained in Production Example 2 was fed to the gel grinding device in accordance with the present invention and subjected to gel grinding. As the screw and the barrel of the gel grinding device, screw No. S86-445 shown in Table 1 and barrel No. B88-178 shown in Table 2, respectively, were used. The same operations as those of Example 17 were carried out, so that a particulate hydrogel (18), water absorbent resin particles (18), and a water absorbent resin powder (18) were obtained. The water absorbent resin powder (18) had 19.2 mass % of 500 μm-non-passing particles. The water absorbent resin powder (18) had a surface tension of 72.2 [mN/m]. Physical properties of the water absorbent resin powder (18) are shown in Table 7. Physical properties of the water absorbent resin particles (18) are shown in Table 8. The other physical properties of the water absorbent resin powder (18) are shown in Table 9.

Example 19

The cut hydrogel (5) obtained in Production Example 5 was fed to the gel grinding device in accordance with the present invention and subjected to gel grinding. As the screw and the barrel of the gel grinding device, screw No. S86-445 shown in Table 1 and barrel No. B88-478 shown in Table 2, respectively, were used. The same operations as those of Example 17 were carried out, so that a particulate hydrogel (19), water absorbent resin particles (19), and a water absorbent resin powder (19) were obtained. The water absorbent resin powder (19) had 35.5 mass % of 500 μm-non-passing particles. The water absorbent resin powder (19) had a surface tension of 72.5 [mN/m]. Physical properties of the water absorbent resin powder (19) are shown in Table 7. Physical properties of the water absorbent resin particles (19) are shown in Table 8. The other physical properties of the water absorbent resin powder (19) are shown in Table 9.

Comparative Example 5

The cut hydrogel (3) obtained in Production Example 3 was fed to the gel grinding device in accordance with the present invention and subjected to gel grinding. As the screw and the barrel of the gel grinding device, screw No. S86-445 shown in Table 1 and barrel No. B88-844 shown in Table 2, respectively, were used. The same operations as those of Example 17 were carried out, so that a comparative particulate hydrogel (5), comparative water absorbent resin particles (5), and a comparative water absorbent resin powder (5) were obtained. Physical properties of the comparative water absorbent resin powder (5) are shown in Table 7. Physical properties of the comparative water absorbent resin particles (5) are shown in Table 8. The other physical properties of the water absorbent resin powder (5) are shown in Table 9.

Comparative Examples 6 through 8

(i) A water absorbent resin powder taken out from a disposable diaper (manufactured by Procter & Gamble Japan, product name: "Pampers Sarasara Care Pants") purchased in Japan in May 2013 (referred to as a comparative water absorbent resin powder (6)), (ii) a water absorbent resin powder taken out from a disposable diaper (manufactured by Procter & Gamble, product name: "Pampers Supersec") purchased in Brazil in July 2010 (referred to as a comparative water absorbent resin powder (7)), and (iii) a water absorbent resin powder taken out from a disposable diaper (manufactured by HENGAN, product name: "Anerle Cho-nou-kyuu") purchased in China in May 2012 (referred to as a comparative water absorbent resin powder (8)) were each subjected to measurement of a thermal conductivity, an apparent heat loss amount, CRC, AAP, SFC, an internal gas bubbles ratio, a ratio of particles of less than 150 μm after an impact resistance test. Results of the measurement are shown in Table 7. The other physical properties of the comparative water absorbent resin powders (6) through (8) are shown in Table 9.

Example 20

With 30 g of the water absorbent resin powder (18) obtained in Example 18, 1.5 g of pulp was evenly mixed, so that an absorbent body 1 was obtained. An absorbent body heat loss amount of the absorbent body 1 was measured by use of the device illustrated in FIG. 9. A result of the measurement is shown in Table 10. Note, however, that as the top sheet and the back sheet, a top sheet and a back sheet which had been taken out from product name: Mamy Poko tape type, size L manufactured by Unicharm Corporation (purchased in Japan in February 2014) were used. The top sheet is made of unwoven cloth and paper, and is positioned so as to be closest to a wearer. The back sheet is a water-impermeable material that is positioned so as to be opposite from the top sheet across an absorbent body provided between the top sheet and the back sheet.

Comparative Example 9

The same operations as those of Example 20 were carried out except that 30 g of the comparative water absorbent resin powder (5) obtained in Comparative Example 5 was used, so that a comparative absorbent body 1 was obtained. An absorbent body heat loss amount of the comparative absorbent body 1 was measured. A result of the measurement is shown in Table 10.

TABLE 7

| | | Thermal conductivity [mW/(m · K)] | Apparent heat loss amount [J] | CRC [g/g] | AAP [g/g] | SFC [1] | Internal gas bubbles ratio [%] | Ratio of particles of less than 150 μm after impact resistance test [wt %] |
|---|---|---|---|---|---|---|---|---|
| Example 15 | Water absorbent resin powder (15) | 122 | 464 | 30.0 | 25.2 | 55 | 2.7 | 2.6 |
| Example 16 | Water absorbent resin powder (16) | 122 | 468 | 31.7 | 24.8 | 34 | 2.7 | 2.5 |
| Example 17 | Water absorbent resin powder (17) | 120 | 460 | 28.0 | 24.3 | 123 | 2.8 | 2.5 |
| Example 18 | Water absorbent resin powder (18) | 119 | 461 | 28.0 | 24.0 | 121 | 3.0 | 2.9 |
| Example 19 | Water absorbent resin powder (19) | 110 | 443 | 27.8 | 24.6 | 146 | 3.5 | 3.0 |
| Comparative Example 5 | Comparative water absorbent resin powder (5) | 129 | 481 | 30.0 | 23.8 | 50 | 2.0 | 3.2 |
| Comparative Example 6 | Comparative water absorbent resin powder (6) | 129 | 475 | 32.1 | 21.3 | 19 | 1.6 | 5.8 |
| Comparative Example 7 | Comparative water absorbent resin powder (7) | 130 | 487 | 24.4 | 21.7 | 89 | 0.9 | 5.7 |
| Comparative Example 8 | Comparative water absorbent resin powder (8) | 120 | 464 | 31.3 | 17.3 | 2 | 3.8 | 6.7 |

1) [$10^{-7} \cdot cm^3 \cdot s/g$]

TABLE 8

| | Water absorbent resin particles | | | | |
|---|---|---|---|---|---|
| | CRC [g/g] | Water soluble component [wt %] | Weight average particle diameter (D50) [μm] | Logarithmic standard deviation of particle size distribution (σζ) | 150 μm-passing particles [wt %] |
| Example 15 | 36.7 | 12 | 450 | 0.41 | 0.5 |
| Example 16 | 36.7 | 12 | 450 | 0.41 | 0.5 |
| Example 17 | 33.4 | 8.2 | 363 | 0.32 | 0.3 |
| Example 18 | 33.0 | 8.4 | 365 | 0.33 | 0.4 |
| Example 19 | 32.0 | 7.8 | 450 | 0.40 | 0.5 |
| Comparative Example 5 | 37.0 | 12.1 | 456 | 0.41 | 0.5 |

TABLE 9

| | Water absorbent resin powder | | | |
|---|---|---|---|---|
| | Water soluble component [wt %] | Weight average particle diameter (D50) [μm] | Logarithmic standard deviation of particle size distribution (σζ) | 150 μm-passing particles [wt %] |
| Example 15 | 11.7 | 447 | 0.41 | 0.6 |
| Example 16 | 11.9 | 454 | 0.41 | 0.5 |
| Example 17 | 8.0 | 367 | 0.32 | 0.3 |
| Example 18 | 8.0 | 365 | 0.33 | 0.4 |
| Example 19 | 7.7 | 456 | 0.41 | 0.4 |
| Comparative Example 5 | 11.9 | 458 | 0.41 | 0.4 |
| Comparative Example 6 | 16.2 | 392 | 0.42 | 2.8 |
| Comparative Example 7 | 10.9 | 348 | 0.41 | 3.1 |
| Comparative Example 8 | 5.9 | 351 | 0.39 | 4.3 |

TABLE 10

| | | Absorbent body heat loss amount [J] |
|---|---|---|
| Example 20 | Water absorbent resin powder (18) | 117 |
| Comparative Example 9 | Comparative water absorbent resin powder (5) | 144 |

(Conclusion)

As shown in Table 7, it is found that the water absorbent resin powder in accordance with the present invention not only is excellent in liquid permeability (SFC) and water absorption performance (CRC, AAP), but also has fewer particles of less than 150 μm after the impact resistance test, has a proper internal gas bubbles ratio, and has a small thermal conductivity and consequently has a small apparent heat loss amount. Even after production of a disposable diaper, such a water absorbent resin powder has a high heat retaining property and has a small absorbent body heat loss amount as shown in Table 10.

INDUSTRIAL APPLICABILITY

A gel grinding device in accordance with the present invention, a method for producing a polyacrylic acid (salt)-based water absorbent resin powder in accordance with the present invention, and a water absorbent resin powder are useful to sanitary materials such as a disposable diaper, a sanitary napkin, and a blood absorbent for medical use. Further, the gel grinding device, the method, and the water absorbent resin powder can also be variously used for a pet urine absorbent, a urine gelatinizer of a portable toilet, an agent for preserving freshness of vegetables and fruits etc., a drip absorbent for meats and fishes, a refrigerant, a disposable body warmer, a battery gelatinizer, a water retention agent for plants, soil, etc., a condensation preventing agent, a waterproofing agent, a packing agent, artificial snow, etc.

REFERENCE SIGNS LIST

11 Screw
12 Porous plate
13 Barrel
14 Feed opening
15 Hopper
16 Extrusion opening
17 Rotary blade
18 Ring
19 Return preventing member
20 Base
21 Motor and speed reducer
22 Rotating shaft
23 Flight section
100 Gel grinding device
200 Cylindrical acrylic resin cell
201 Woven stainless wire
202 Heat insulating material
203 Heat insulating material
204 Vinyl chloride resin piston
205 Thermocouple
206 Hot plate
207 Water absorbent resin powder
208 Top sheet
209 Back sheet
210 Weight
211 Absorbent body

The invention claimed is:

1. A method for producing a polyacrylic acid (salt)-based water absorbent resin powder, comprising:
   a polymerization step of polymerizing an acrylic acid (salt)-based monomer aqueous solution to form a polyacrylic acid (salt)-based hydrogel-like crosslinked polymer having a resin solid content of 10 wt % to 80 wt %;
   a gel grinding step, carried out during or after the polymerization, of carrying out gel grinding with respect to the hydrogel-like crosslinked polymer to form a particulate polyacrylic acid (salt)-based hydrogel-like crosslinked polymer; and
   a drying step carried out after the gel grinding,
   in the gel grinding step, the hydrogel-like crosslinked polymer being ground by use of a gel grinding device comprising:
   a screw;
   a feed opening;
   an extrusion opening;
   a porous plate; and
   a barrel,
   the barrel including at least one return preventing member provided on an inner surface of the barrel, and
   the barrel satisfying at least one of the following (1) and (2):
   (1) $0.05 \leq YH/N \leq 0.25$; and
   (2) $0.05 \leq YF/N \leq 0.25$
   where YH is a height of the at least one return preventing member which height is obtained by cutting the barrel in a direction vertical to a direction in which a gel of the water absorbent resin is extruded; YF is a width of a top surface of the at least one return preventing member, the width being along a direction vertical to a direction in which the at least one return preventing member extends; and N is a diameter of an inner part of the barrel which diameter does not include the at least one return preventing member.

2. The method as set forth in claim 1, wherein $T/N^3$ ranges from 0.05 to 2.0 where T is an amount [g/hr] in which the gel grinding device treats a hydrogel per hour and $T/N^3$ is a treatment amount-to-inner diameter ratio [g/hr/mm$^3$] that is a treatment amount per unit time of the gel grinding device.

3. The method as set forth in claim 1, wherein the particulate polyacrylic acid (salt)-based hydrogel-like crosslinked polymer which is obtained in the gel grinding step is dried under a condition where a through-flow belt-type dryer is used, a drying temperature is 150° C. to 250° C., and hot air blows in a vertical direction (an up-and-down direction) at an air velocity of 0.8 [m/s] to 2.5 [m/s].

4. The method as set forth in claim 1, wherein the barrel of the gel grinding device has a temperature of 40° C. to 120° C. while the gel grinding step is being carried out.

* * * * *